United States Patent
Wallace et al.

(10) Patent No.: US 11,812,980 B2
(45) Date of Patent: Nov. 14, 2023

(54) INVERTING THROMBECTOMY APPARATUSES HAVING ENHANCED TRACKING

(71) Applicant: STRYKER CORPORATION, Fremont, CA (US)

(72) Inventors: Michael P. Wallace, Pleasanton, CA (US); Robert Garabedian, Mountain View, CA (US); Roy Leguidleguid, Union City, CA (US); E. Skott Greenhalgh, Gladwyne, PA (US)

(73) Assignee: STRYKER CORPORATION, Fremont, CA (US)

( * ) Notice: Subject to any disclaimer, the term of this patent is extended or adjusted under 35 U.S.C. 154(b) by 276 days.

(21) Appl. No.: 17/169,334

(22) Filed: Feb. 5, 2021

(65) Prior Publication Data

US 2021/0186543 A1 Jun. 24, 2021

Related U.S. Application Data

(63) Continuation of application No. 16/183,149, filed on Nov. 7, 2018, now Pat. No. 10,912,576.

(Continued)

(51) Int. Cl.
*A61B 17/22* (2006.01)
*A61M 25/00* (2006.01)
(Continued)

(52) U.S. Cl.
CPC ...... *A61B 17/22031* (2013.01); *A61B 17/221* (2013.01); *A61B 17/320725* (2013.01);
(Continued)

(58) Field of Classification Search
CPC ............ A61B 17/22031; A61B 17/221; A61B 17/320725; A61B 2017/00867;
(Continued)

(56) References Cited

U.S. PATENT DOCUMENTS

| | | | |
|---|---|---|---|
| 3,515,137 A | 6/1970 | Santomieri | |
| 3,655,474 A * | 4/1972 | Constantine | B32B 37/06 156/196 |

(Continued)

FOREIGN PATENT DOCUMENTS

| | | |
|---|---|---|
| AU | 2015210338 | 8/2015 |
| CN | 201079423 | 7/2008 |

(Continued)

OTHER PUBLICATIONS

Foreign OA for JP Patent Appln. No. 2019-507078 dated Feb. 3, 2021.

(Continued)

*Primary Examiner* — Jocelin C Tanner
(74) *Attorney, Agent, or Firm* — Seager, Tufte & Wickhem, LLP

(57) ABSTRACT

Mechanical thrombectomy apparatuses, and particularly knitted rolling tube mechanical thrombectomy apparatuses configured to have improved tracking for delivery through tortious vessels are described herein. Also described herein are methods of removing clots using a mechanical thrombectomy apparatuses in which the clot is larger than the tractor portion of the mechanical thrombectomy apparatus.

18 Claims, 52 Drawing Sheets

Related U.S. Application Data

(60) Provisional application No. 62/664,822, filed on Apr. 30, 2018, provisional application No. 62/583,803, filed on Nov. 9, 2017.

(51) Int. Cl.

| | | |
|---|---|---|
| *A61B 17/221* | (2006.01) | |
| *A61B 17/3207* | (2006.01) | |
| *A61M 25/01* | (2006.01) | |
| *A61B 17/00* | (2006.01) | |
| *A61B 17/34* | (2006.01) | |

(52) U.S. Cl.
CPC .... *A61M 25/0074* (2013.01); *A61M 25/0119* (2013.01); *A61B 2017/00867* (2013.01); *A61B 2017/2215* (2013.01); *A61B 2017/22034* (2013.01); *A61B 2017/22038* (2013.01); *A61B 2017/22079* (2013.01); *A61B 2017/3435* (2013.01)

(58) Field of Classification Search
CPC ........... A61B 2017/22034; A61B 2017/22038; A61B 2017/22079; A61B 2017/2215; A61B 2017/3435; A61M 25/0074; A61M 25/0119
See application file for complete search history.

(56) References Cited

U.S. PATENT DOCUMENTS

| | | | |
|---|---|---|---|
| 4,222,380 A | 9/1980 | Terayama | |
| 4,243,040 A | 1/1981 | Beecher | |
| 4,324,262 A | 4/1982 | Hall | |
| 4,469,100 A | 9/1984 | Hardwick | |
| 4,604,094 A | 8/1986 | Shook | |
| 4,646,736 A | 3/1987 | Auth | |
| 4,863,440 A | 9/1989 | Chin | |
| 4,946,440 A | 8/1990 | Hall | |
| 5,011,488 A | 4/1991 | Ginsburg | |
| 5,329,923 A | 7/1994 | Lundquist | |
| 5,364,345 A | 11/1994 | Lowery et al. | |
| 5,389,100 A | 2/1995 | Bacich et al. | |
| 5,662,703 A | 9/1997 | Yurek et al. | |
| 5,662,713 A * | 9/1997 | Andersen | A61F 2/958 |
| | | | 128/898 |
| 5,971,938 A | 10/1999 | Hart et al. | |
| 6,156,055 A | 12/2000 | Ravenscroft | |
| 6,221,006 B1 | 4/2001 | Dubrul et al. | |
| 6,238,412 B1 | 5/2001 | Dubrul et al. | |
| 6,245,078 B1 | 6/2001 | Ouchi | |
| 6,258,115 B1 | 7/2001 | Dubrul | |
| 6,544,278 B1 | 4/2003 | Vrba et al. | |
| 6,569,181 B1 * | 5/2003 | Burns | A61F 2/95 |
| | | | 606/198 |
| 6,620,179 B2 | 9/2003 | Brook et al. | |
| 6,635,068 B1 | 10/2003 | Dubrul et al. | |
| 6,635,070 B2 | 10/2003 | Leeflang et al. | |
| 6,830,561 B2 | 12/2004 | Jansen et al. | |
| 6,846,029 B1 | 1/2005 | Ragner et al. | |
| 6,942,682 B2 | 9/2005 | Vrba et al. | |
| 7,621,870 B2 | 11/2009 | Berrada et al. | |
| 7,780,696 B2 | 8/2010 | Daniel et al. | |
| 8,057,496 B2 | 11/2011 | Fischer, Jr. | |
| 8,070,769 B2 | 12/2011 | Broome | |
| 8,092,486 B2 | 1/2012 | Berrada et al. | |
| 8,657,867 B2 | 2/2014 | Dorn et al. | |
| 8,721,714 B2 | 5/2014 | Kelley | |
| 8,784,442 B2 | 7/2014 | Jones et al. | |
| 8,795,305 B2 | 8/2014 | Martin et al. | |
| 8,956,384 B2 | 2/2015 | Berrada et al. | |
| 9,028,401 B1 | 5/2015 | Bacich et al. | |
| 9,125,683 B2 | 9/2015 | Farhangnia et al. | |
| 9,126,016 B2 | 9/2015 | Fulton | |
| 9,155,552 B2 | 10/2015 | Ulm, III | |
| 9,173,668 B2 | 11/2015 | Ulm, III | |
| 9,186,487 B2 | 11/2015 | Dubrul et al. | |
| 9,358,037 B2 | 1/2016 | Farhangnia et al. | |
| 9,259,237 B2 | 2/2016 | Quick et al. | |
| 9,351,747 B2 | 5/2016 | Kugler et al. | |
| 9,463,035 B1 * | 10/2016 | Greenhalgh | A61B 10/04 |
| 9,643,035 B2 | 5/2017 | Mastenbroek | |
| 9,717,514 B2 | 8/2017 | Martin et al. | |
| 9,848,975 B2 | 12/2017 | Hauser | |
| 9,849,014 B2 | 12/2017 | Kusleika | |
| 9,962,178 B2 | 5/2018 | Greenhalgh et al. | |
| 10,010,335 B2 | 7/2018 | Greenhalgh et al. | |
| 10,016,266 B2 | 7/2018 | Hauser | |
| 10,028,759 B2 | 7/2018 | Wallace et al. | |
| 10,130,385 B2 | 11/2018 | Farhangnia et al. | |
| 10,271,864 B2 | 4/2019 | Greenhalgh et al. | |
| 10,327,883 B2 | 6/2019 | Yachia | |
| 2001/0003307 A1 * | 6/2001 | Sivacoe | B08B 9/0553 |
| | | | 165/95 |
| 2002/0032455 A1 | 3/2002 | Boock et al. | |
| 2002/0035373 A1 | 3/2002 | Carlson et al. | |
| 2002/0173819 A1 | 11/2002 | Leeflang et al. | |
| 2003/0083693 A1 | 5/2003 | Daniel et al. | |
| 2003/0135258 A1 | 7/2003 | Andreas et al. | |
| 2003/0153873 A1 | 8/2003 | Luther et al. | |
| 2003/0168068 A1 | 9/2003 | Poole et al. | |
| 2003/0176884 A1 | 9/2003 | Berrada et al. | |
| 2003/0208224 A1 | 11/2003 | Broome | |
| 2004/0098033 A1 | 5/2004 | Leeflang et al. | |
| 2004/0199202 A1 | 10/2004 | Dubrul et al. | |
| 2005/0085826 A1 | 4/2005 | Nair et al. | |
| 2005/0085849 A1 | 4/2005 | Sepetka et al. | |
| 2005/0119668 A1 | 6/2005 | Teague et al. | |
| 2005/0177132 A1 | 8/2005 | Lentz et al. | |
| 2005/0187570 A1 | 8/2005 | Nguyen et al. | |
| 2005/0245876 A1 | 11/2005 | Khosravi et al. | |
| 2005/0283166 A1 | 12/2005 | Greenhalgh | |
| 2005/0283186 A1 | 12/2005 | Berrada et al. | |
| 2006/0042786 A1 | 3/2006 | West | |
| 2006/0089533 A1 | 4/2006 | Ziegler et al. | |
| 2006/0100662 A1 | 5/2006 | Daniel et al. | |
| 2006/0173525 A1 | 8/2006 | Behl et al. | |
| 2006/0195137 A1 | 8/2006 | Sepetka et al. | |
| 2006/0200221 A1 | 9/2006 | Malewicz | |
| 2006/0276874 A1 | 12/2006 | Wilson et al. | |
| 2006/0293696 A1 | 12/2006 | Fahey et al. | |
| 2007/0112374 A1 | 5/2007 | Paul, Jr. et al. | |
| 2007/0123798 A1 | 5/2007 | Rahamimov | |
| 2007/0149996 A1 | 6/2007 | Coughlin | |
| 2007/0213765 A1 | 9/2007 | Adams et al. | |
| 2008/0183136 A1 | 7/2008 | Lenker et al. | |
| 2009/0076417 A1 | 3/2009 | Jones | |
| 2010/0030256 A1 | 2/2010 | Dubrul et al. | |
| 2010/0042136 A1 | 2/2010 | Berrada et al. | |
| 2010/0087844 A1 | 4/2010 | Fischer, Jr. | |
| 2010/0137846 A1 | 6/2010 | Desai et al. | |
| 2010/0190156 A1 | 7/2010 | Van Wordragen et al. | |
| 2010/0249815 A1 | 9/2010 | Jantzen et al. | |
| 2011/0034987 A1 | 2/2011 | Kennedy | |
| 2011/0118817 A1 | 5/2011 | Gunderson et al. | |
| 2011/0160763 A1 | 6/2011 | Ferrera et al. | |
| 2011/0265681 A1 | 11/2011 | Allen et al. | |
| 2011/0288529 A1 | 11/2011 | Fulton | |
| 2011/0288572 A1 | 11/2011 | Martin | |
| 2012/0059309 A1 | 3/2012 | Di Palma et al. | |
| 2012/0083824 A1 | 4/2012 | Berrada et al. | |
| 2012/0083868 A1 | 4/2012 | Shrivastava | |
| 2012/0165859 A1 | 6/2012 | Eckhouse et al. | |
| 2012/0271105 A1 | 10/2012 | Nakamura et al. | |
| 2013/0046332 A1 | 2/2013 | Jones et al. | |
| 2013/0096571 A1 | 4/2013 | Massicotte et al. | |
| 2013/0116721 A1 | 5/2013 | Takagi et al. | |
| 2013/0226196 A1 | 8/2013 | Smith | |
| 2013/0317589 A1 | 11/2013 | Martin et al. | |
| 2013/0345739 A1 | 12/2013 | Brady et al. | |
| 2014/0005712 A1 | 1/2014 | Martin et al. | |
| 2014/0005717 A1 | 1/2014 | Martin et al. | |
| 2014/0046133 A1 | 2/2014 | Nakamura et al. | |
| 2014/0155980 A1 | 6/2014 | Turjman | |

(56) References Cited

U.S. PATENT DOCUMENTS

| | | |
|---|---|---|
| 2014/0257253 A1 | 9/2014 | Jemison |
| 2014/0276403 A1 | 9/2014 | Follmer et al. |
| 2014/0330286 A1 | 11/2014 | Wallace |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1* | 1/2015 | Lund-Clausen ..... A61B 17/221 606/127 |
| 2015/0005792 A1 | 1/2015 | Ahn |
| 2015/0018859 A1 | 1/2015 | Quick et al. |
| 2015/0018860 A1 | 1/2015 | Quick et al. |
| 2015/0088190 A1 | 3/2015 | Jensen |
| 2015/0112376 A1 | 4/2015 | Molaei et al. |
| 2015/0164523 A1 | 6/2015 | Brady et al. |
| 2015/0164666 A1 | 6/2015 | Johnson et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0351775 A1 | 12/2015 | Fulton, III |
| 2015/0359547 A1 | 12/2015 | Vale et al. |
| 2016/0022293 A1 | 1/2016 | Dubrul et al. |
| 2016/0058458 A1 | 3/2016 | Hansen et al. |
| 2016/0058540 A1 | 3/2016 | Don Michael |
| 2016/0074627 A1 | 3/2016 | Cottone |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0206371 A1 | 7/2016 | Elgaard et al. |
| 2016/0228134 A1 | 8/2016 | Martin et al. |
| 2016/0242799 A1 | 8/2016 | Bonneau et al. |
| 2016/0256179 A1 | 9/2016 | Walish et al. |
| 2017/0035445 A1 | 2/2017 | Nguyen et al. |
| 2017/0042571 A1 | 2/2017 | Levi |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0112513 A1 | 4/2017 | Marchand et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0348014 A1 | 12/2017 | Wallace et al. |
| 2018/0042624 A1 | 2/2018 | Greenhalgh et al. |
| 2018/0042626 A1 | 2/2018 | Greenhalgh et al. |
| 2018/0049766 A1 | 2/2018 | Nolan et al. |
| 2018/0070968 A1 | 3/2018 | Wallace et al. |
| 2018/0236205 A1 | 8/2018 | Krautkremer et al. |
| 2019/0046219 A1 | 2/2019 | Marchand et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0033614 A1 | 11/2019 | Greenhalgh et al. |
| 2019/0336148 A1 | 11/2019 | Greenhalgh et al. |

FOREIGN PATENT DOCUMENTS

| | | |
|---|---|---|
| CN | 102186427 | 9/2011 |
| CN | 102933161 | 2/2013 |
| CN | 102988096 | 3/2013 |
| CN | 103764049 | 4/2014 |
| CN | 103889347 | 6/2014 |
| CN | 104000635 | 8/2014 |
| CN | 104042304 | 9/2014 |
| CN | 104068910 | 10/2014 |
| CN | 104523320 | 4/2015 |
| CN | 104582608 | 4/2015 |
| CN | 108348319 | 7/2018 |
| CN | 111281482 | 6/2020 |
| EP | 1254634 | 11/2002 |
| GB | 1588072 | 4/1981 |
| GB | 2498349 | 7/2013 |
| JP | 2003-38500 | 2/2003 |
| JP | 2003-135604 | 5/2003 |
| JP | 2016-41275 | 3/2016 |
| WO | WO 00/32118 | 6/2000 |
| WO | WO 0202162 | 1/2002 |
| WO | WO 2005096963 | 10/2005 |
| WO | WO 2008/088371 | 7/2008 |
| WO | WO 2009086482 | 7/2009 |
| WO | WO 2012009675 | 1/2012 |
| WO | WO 2012049652 | 4/2012 |
| WO | WO 2012162437 | 11/2012 |
| WO | WO 2015189354 | 12/2015 |
| WO | WO 2017058280 | 4/2017 |
| WO | WO 2017189535 | 11/2017 |
| WO | WO 2017189550 | 11/2017 |
| WO | WO 2017189591 | 11/2017 |
| WO | WO 2017189615 | 11/2017 |
| WO | WO 2017210487 | 12/2017 |
| WO | WO 2018049317 | 3/2018 |
| WO | WO 2019010318 | 1/2019 |
| WO | WO 2019094456 | 5/2019 |
| WO | WO 2019222117 | 11/2019 |

OTHER PUBLICATIONS

Foreign OA for JP Patent Appln. No. 2019-507075 dated Feb. 1, 2021.
Notice of Allowance for U.S. Appl. No. 16/397,089 dated Feb. 18, 2021.
Foreign OA for JP Patent Appln. No. 2018-562633 dated Mar. 4, 2021.
Foreign Notice of Reasons of Rejection for JP Patent Appln. No. 2019-513286 dated Jul. 26, 2021 (with English translation).
Foreign Exam Report for EP Patent Appln. No. 19773654.9 dated Aug. 24, 2021.
Foreign OA for JP Patent Appln. No. 2020-093260 dated Apr. 20, 2021.
Non-Final Office Action for U.S. Appl. No. 16/566,393 dated May 11, 2021.
Amendment Response to NFOA for U.S. Appl. No. 16/566,393 dated Aug. 11, 2021.
Non-Final Office Action for U.S. Appl. No. 16/594,259 dated Aug. 31, 2021.
Foreign OA for CN Patent Appln. No. 201780067034.4 dated Sep. 3, 2021.
Foreign Search Report for CN Patent Appln. No. 201780067034.4 dated Aug. 30, 2021.
Response to OA for EP Patent Appln. No. 19773654.9 dated Dec. 22, 2021 with Amended Claims and Description.
Extended European Search Report for EP Patent Appln. No. 21192438.6 dated Nov. 23, 2021.
Foreign Notice of Rejection for JP Patent Appln. No. 2020-093260 dated Dec. 21, 2021.
Foreign Communication Under Rule 71(3) for EP Patent Appln. No. 18807524.6 dated Jul. 1, 2022.
Foreign Communication Pursuant to Article 94(3) for EP Patent Appln. No. 17772186.7 dated Jun. 17, 2022.
Foreign OA for JP Patent Appln. No. 2019-513286 dated May 10, 2022.
Foreign OA for JP Patent Appln. No. 2019-571360 dated Jun. 9, 2022.
Amendment Response to NFOA for U.S. Appl. No. 16/707,045 dated Jul. 11, 2022.
Extended European Search Report for EP Patent Appln. No. 22162955.3 dated Sep. 5, 2022.
Foreign Notice of Rejection for JP Patent Appln. No. 2020-093260 dated Aug. 2, 2022.
Final Office Action for U.S. Appl. No. 16/707,045 dated Jul. 22, 2022.

(56) References Cited

OTHER PUBLICATIONS

Foreign Response for EP Patent Appln. No. 21192438.6 dated Jul. 18, 2022.
Foreign Response for JP Patent Appln. No. 2021-72088 dated Jul. 4, 2022.
Notice of Rejection for JP Patent Appln. No. 2020-523723 dated Aug. 8, 2022 with English translation.
Notice of Allowance for U.S. Appl. No. 16/790,744 dated Jun. 17, 2022.
Notice of Allowance for U.S. Appl. No. 16/731,649 dated Jul. 20, 2022.
Non-Final Office Action for U.S. Appl. No. 15/496,570, dated Aug. 9, 2017.
PCT International Search Report and Written Opinion for International Appln. No. PCT/US2017/029440, Applicant Stryker Corporation, dated Jul. 7, 2017.
PCT Invitation to Pay Additional Fees for International Appln. No. PCT/US2017/029366, Applicant Stryker Corporation, dated Jul. 7, 2017.
PCT International Search Report and Written Opinion for International Appln. No. PCT/US2017/029472, Applicant Stryker Corporation, dated Jul. 7, 2017.
PCT International Search Report and Written Opinion for International Appln. No. PCT/US2017/035543, Applicant Stryker Corporation, dated Aug. 14, 2017.
PCT International Search Report and Written Opinion for International Appln. No. PCT/US2017/029366, Applicant Stryker Corporation, dated Aug. 29, 2017.
PCT Invitation to Pay Additional Fees for International Appln. No. PCT/US2017/029345, Applicant Stryker Corporation, dated Oct. 17, 2017.
Non-Final Office Action for U.S. Appl. No. 15/496,786, dated Nov. 1, 2017.
PCT International Search Report and Written Opinion for International Appln. No. PCT/US2017/050933, Applicant Stryker Corporation, forms PCT/ISA/210, 220, and 237, dated Nov. 10, 2017 (16 pages).
Response to Non-Final Office Action for U.S. Appl. No. 14/496,786, filed Feb. 1, 2018.
Non-final office action dated Feb. 1, 2018 for U.S. Appl. No. 15/496,668.
Response to Restriction for U.S. Appl. No. 15/496,668, filed Feb. 21, 2018.
International search report and written opinion dated Feb. 28, 2018 for PCT/US2017/029345, Applicant Stryker Corporation 26 pages.
Notice of Allowance dated Mar. 22, 2018 for U.S. Appl. No. 15/496,668.
Notice of Allowance dated Apr. 19, 2018 for U.S. Appl. No. 15/496,570.
Notice of Allowance dated Apr. 19, 2018 for U.S. Appl. No. 15/496,786.
Non-Final Office Action dated Sep. 5, 2018 for U.S. Appl. No. 15/291,015.
Extended European Search Report dated Aug. 22, 2018 for European patent appln No. 16852212.6.
Extended European Search Report dated Oct. 5, 2018 for European patent appln No. 18174891.4.
Invitation to Pay Additional Fees for International Patent Appln. No. PCT/US2018/040937 dated Sep. 26, 2018.
Response to Non-Final Office Action for U.S. Appl. No. 15/291,015, filed Sep. 5, 2018.
International search report and written opinion dated Nov. 14, 2018 for PCT/US2018/040937, Applicant Stryker Corporation 16 pages.
Notice of Allowance dated Dec. 11, 2018 for U.S. Appl. No. 15/291,015.
Invitation to Pay Additional Fees for International Patent Appln. No. PCT/US2018/059607 dated Jan. 31, 2019.
Japanese Office action dated Mar. 19, 2019 for Japanese Application No. 2018-535810 (with English Language translation).

International Search Report and Written Opinion dated Mar. 28, 2019 for International Appln. No. PCT/US2018/059607.
Notice of Allowance dated Apr. 10, 2019 for U.S. Appl. No. 15/611,546.
Response to Extended European Search Report for EP Patent Appln. No. 16852212.6 dated Mar. 15, 2019.
European Patent Office Communication Rule 161(1) and 162 dated Feb. 5, 2019 for EP Patent Appln. No. 17729703.3.
European Patent Office Communication Rule 161(1) and 162 EPC for EP Patent Appln. No. 17737084.8 dated Dec. 18, 2018.
European Patent Office Communication Rule 161(1) and 162 for EP Patent Appln. No. 17722277.5 dated Dec. 13, 2018.
European Patent Office Communication Rule 161(1) and 162 dated Dec. 13, 2018 for EP Patent Appln. No. 17722290.8.
European Patent Office Communication Rule 161(1) and 162 dated Dec. 13, 2018 for EP Patent Appln. No. 17721036.6.
Response to Extended European Search Report for EP Patent Appln. No. 18174891.4 dated May 28, 2019.
Restriction Requirement dated Jun. 28, 2019 for U.S. Appl. No. 15/700,685.
International Search Report and Written Opinion dated May 6, 2016 for PCT/US2016/017982.
Response to European Patent Office Communication Rule 161(1) and 162 EPC filed Jun. 11, 2019, for EP Patent Appln. No. 17737084.8.
Response to European Patent Office Communication Rule 161(1) and 162 filed Jun. 4, 2019 for EP Patent Appln. No. 17722277.5.
Response to European Patent Office Communication Rule 161(1) and 162 filed Jun. 4, 2019 for EP Patent Appln. No. 17722290.8.
Response to European Patent Office Communication 161(1) and 162 filed Jun. 11, 2019 for EP Patent Appln. No. 17721036.6.
European Patent Office Communication Rule 161(1) and 162 dated Apr. 23, 2019 for EP Patent Appln. No. 17772186.7.
Response to Non-Final Office Action filed Nov. 8, 2017 for U.S. Appl. No. 15/496,570.
Response to Non-Final Office Action filed Feb. 1, 2018 for U.S. Appl. No. 15/496,786.
Restriction Requirement dated Apr. 11, 2019 for U.S. Appl. No. 15/497,092.
Response to Restriction Requirement filed Jun. 11, 2019 for U.S. Appl. No. 15/497,092.
Ex Parte Quayle office action dated Jul. 16, 2019 for U.S. Appl. No. 15/497,092.
Response to Rule 161(1) and 162 EPC filed on Jul. 23, 2019 for EP application No. 17729703.3.
PCT International Search Report and Written Opinion for International Patent Appln. No. PCT/US2019/032601, Applicant Stryker Corporation, dated Jul. 23, 2019 (12 pages).
Response to Restriction Requirement filed Jul. 25, 2019 for U.S. Appl. No. 15/700,685.
Response to Ex Parte Quayle office action filed Jul. 25, 2019 for U.S. Appl. No. 15/497,092.
Office action dated Jun. 5, 2019 for Chinese application No. 2019053101871820, including partial English language translation provided by the foreign associate.
Wikipedia; Embolectomy; retrieved from the internet: https://en.wikipedia.org/wiki/Embolectomy; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.
Boston Scientific; Fetch(TM) 2 Aspiration Catheter (product information); retrieved from the internet: http://www.bostonscientific.com/en-US/products/thrombectomy-systems/fetch2-aspiration-catheter.html; 5 pgs.; retrieved/printed: Mar. 24, 2016.

(56) References Cited

OTHER PUBLICATIONS

Penumbra, Inc.; Indigo® System (product information); retrieved from the internet: http://www.penumbrainc.com/peripherallpercutaneous-thromboembolectomy/indigo-system; 2 pgs.; retrieved/printed: Mar. 24, 2016.
Youtube; Merci Retrieval System X Series Animation; uploaded Mar. 16, 2009 (product information); retrieved from the internet: https://www.youtube.com/watch?v=MGX7deuFkhc; 3 pgs.; retrieved/printed: Mar. 24, 2016.
Covidien; Solitaire(TM) AS Neurovascular Remodeling Device (product information); retrieved from the internet: http://www.ev3.net/neuro/intl/remodeling-devices/solitaire-ab.htm; © 2015; 2 pgs.; retrieved/printed: Mar. 24, 2016.
Notice of Allowance for U.S. Appl. No. 15/043,996 dated Jun. 9, 2016.
Ex Parte Quayle office action dated Aug. 2, 2019 for U.S. Appl. No. 15/497,092.
Non Final Office Action dated Aug. 23, 2019 for U.S. Appl. No. 15/700,685.
Non Final Office Action dated Sep. 3, 2019 for U.S. Appl. No. 15/794,939.
Rule 71(3) Allowance for EP Patent Appln. No. 18174891.4 dated Jul. 30, 2019.
Response to Ex Parte Quayle office action filed Sep. 17, 2019 for U.S. Appl. No. 15/497,092.
Office action response filed on Sep. 26, 2019 for Chinese Patent Application No. 2016800567527, no translation received.
Non-Final Office Action dated Oct. 4, 2019 for U.S. Appl. No. 15/795,097.
Response to Restriction filed Oct. 4, 2019 for U.S. Appl. No. 15/795,097.
Notice of Allowance dated Sep. 27, 2019 for U.S. Appl. No. 15/497,092.
Extended European Search Report dated Oct. 8, 2019 for European Patent Application No. 19191925.7.
Office action dated Oct. 7, 2019 for European Patent Application No. 17729703.3.
Office action dated Oct. 7, 2019 for European Patent Application No. 17737084.8.
Response to European Patent Office Communication Rule 161(1) and 162 filed Oct. 17, 2019 for EP Patent Appln. No. 17772186.7.
Invitation to Pay Additional Fees for International Patent Appln. No. PCT/US2019/050467 dated Oct. 25, 2019.
International Search Report and Written Opinion for International Patent Appln. No. PCT/US2019/050410 dated Oct. 25, 2019.
Notice of Allowance dated Oct. 24, 2019 for U.S. Appl. No. 15/611,546.
Response to Non Final Office Action filed Nov. 8, 2019 for U.S. Appl. No. 15/700,685.
Notice of Allowance dated Nov. 6, 2019 for U.S. Appl. No. 15/795,097.
Rule 71(3) Allowance for EP Patent Appln. No. 17721036.6 dated Oct. 23, 2019.
Rule 71(3) Allowance for EP Patent Appln. No. 17722290.8 dated Nov. 11, 2019.
Notice of Allowance dated Nov. 21, 2019 for U.S. Appl. No. 15/700,685.
Amendment Response dated Dec. 3, 2019 for U.S. Appl. No. 15/794,939.
PCT International Search Report and Written Opinion for International Patent Appln. No. PCT/US2019/050467, Applicant Stryker Corporation, dated Dec. 18, 2019 (17 pages).
Non Final Office Action dated Dec. 27, 2019 for U.S. Appl. No. 16/594,256.
Final Office Action dated Mar. 2, 2020 for U.S. Appl. No. 15/794,939.
Notice of Allowance for U.S. Appl. No. 15/794,939 dated Mar. 31, 2020.
Amendment Response dated Mar. 27, 2020 for U.S. Appl. No. 16/594,256.
Non-Final Office Action for U.S. Appl. No. 16/096,031 dated May 8, 2020.
Non-Final Office Action for U.S. Appl. No. 16/183,162 dated May 13, 2020.
Non-Final Office Action for U.S. Appl. No. 16/169,334 dated May 8, 2020.
Non-Final Office Action for U.S. Appl. No. 16/183,171 dated May 13, 2020.
Foreign OA for Japanese Patent Application No. 2018-535810 dated Feb. 7, 2020.
Amendment Response to Non-Final Office Action for U.S. Appl. No. 16/183,171 dated Jul. 30, 2020.
Amendment Response to Non-Final Office Action for U.S. Appl. No. 16/183,162 dated Jul. 30, 2020.
Applicant Interview Summary for U.S. Appl. No. 16/096,031 dated Jul. 30, 2020.
Applicant Interview Summary for U.S. Appl. No. 16/169,334 dated Jul. 30, 2020.
Applicant Interview Summary for U.S. Appl. No. 16/183,133 dated Aug. 24, 2020.
Non-Final Office Action for U.S. Appl. No. 16/183,149 dated Aug. 18, 2020.
Extended European Search Report for EP Patent Appln. No. 20185092.2 dated Sep. 11, 2020.
EP Examination Report for EP Patent Appln. No. 18745794.0 dated Jul. 20, 2020.
Amendment Response to NFOA for U.S. Appl. No. 16/183,149 dated Sep. 25, 2020.
Notice of Allowance for U.S. Appl. No. 16/183,149 dated Oct. 9, 2020.
Foreign OA for CN Patent Appln. No. 2017800393642 dated Dec. 1, 2020.
Foreign OA for CN Patent Appln. No. 2017800393676 dated Dec. 2, 2020.
Foreign OA for CN Patent Appln. No. 2017800396566 dated Dec. 3, 2020.
Foreign OA for CN Patent Appln. No. 2017800343357 dated Jan. 6, 2021.
Foreign Response for EP Patent Appln. No. 18807524.6 dated Dec. 21, 2020.
PCT International Search Report and Written Opinion for International Appln. No. PCT/US2020/014854, dated Oct. 5, 2020 (13 pages).
PCT International Search Report and Written Opinion for International Appln. No. PCT/US2020/018655, dated Dec. 16, 2020 (22 pages).
PCT International Search Report and Written Opinion for International Appln. No. PCT/US2020/017684, dated Nov. 30, 2020 (19 pages).
Foreign OA for CN Patent Appln. No. 201880046302.9 dated Aug. 25, 2022 (with English translation).
Foreign OA for JP Patent Appln. No. 2021-125123 dated Aug. 23, 2022.
Non-Final Office Action for U.S. Appl. No. 16/707,045 dated Nov. 14, 2022.
Non-Final Office Action for U.S. Appl. No. 16/594,259 dated Nov. 9, 2022.
Notice of Allowance for U.S. Appl. No. 16/722,880 dated Oct. 5, 2022.
Non-Final Office Action for U.S. Appl. No. 16/790,741 dated Nov. 1, 2022.
Foreign OA for CN Patent Appln. No. 202010148570.0 dated Nov. 1, 2022.
Foreign Search Report for CN Patent Appln. No. 202010148570.0 dated Nov. 1, 2022.
Foreign Response for EP Patent Appln. No. 21211363.3 dated Mar. 17, 2022.
Foreign Exam Report for IN Patent Appln. No. 202147016629 dated Mar. 2, 2022.
Foreign OA for IN Patent Appln. No. 202147016649 dated Mar. 28, 2022.
Non-Final Office Action for U.S. Appl. No. 16/707,045 dated Apr. 11, 2022.

(56) References Cited

OTHER PUBLICATIONS

Foreign OA for CN Patent Appln. No. 2017800670344 dated Mar. 21, 2022 with English Translation.
Foreign OA for JP Patent Appln. No. 2021-072088 dated Apr. 5, 2022 with English translation.
Foreign OA for EP Patent Appln. No. 19726855.0 dated May 18, 2022.
Amendment Response to NFOA for U.S. Appl. No. 16/790,741 dated Nov. 21, 2022.
Amendment Response to NFOA for U.S. Appl. No. 16/594,259 dated Jan. 26, 2023.
Notice of Allowance for U.S. Appl. No. 16/790,741 dated Dec. 21, 2022.
Non-Final Office Action for U.S. Appl. No. 17/387,959 dated Jan. 19, 2023.
Foreign OA for CN Patent Appln. No. 201880072826.5 dated Oct. 12, 2022 (with English translation).
Foreign Search Report for CN Patent Appln. No. 201880072826.5 dated Oct. 12, 2022 (with English translation).
Final Office Action for U.S. Appl. No. 16/594,259 dated Mar. 1, 2023.

* cited by examiner

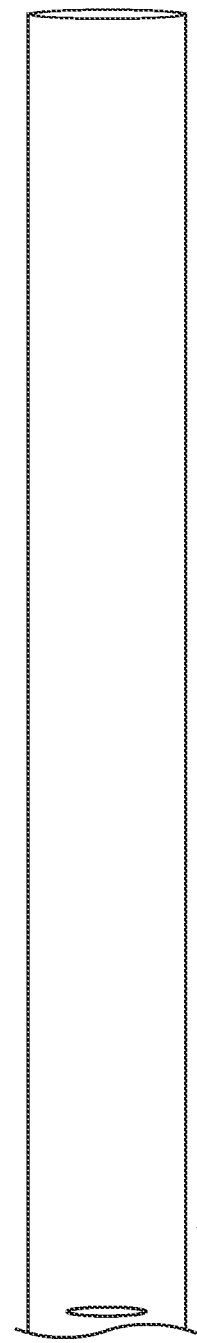
FIG. 1A
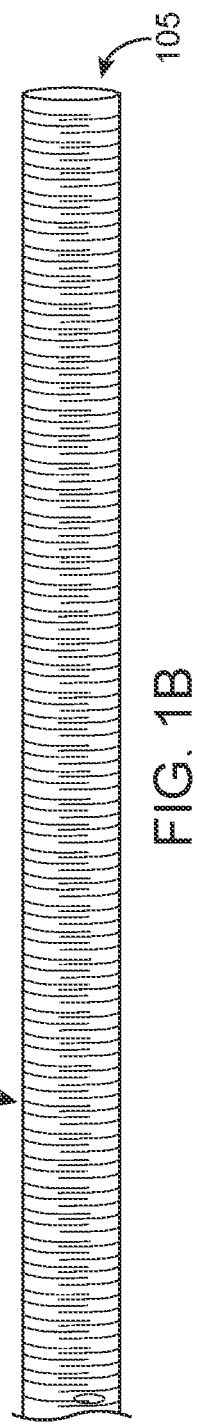
FIG. 1B
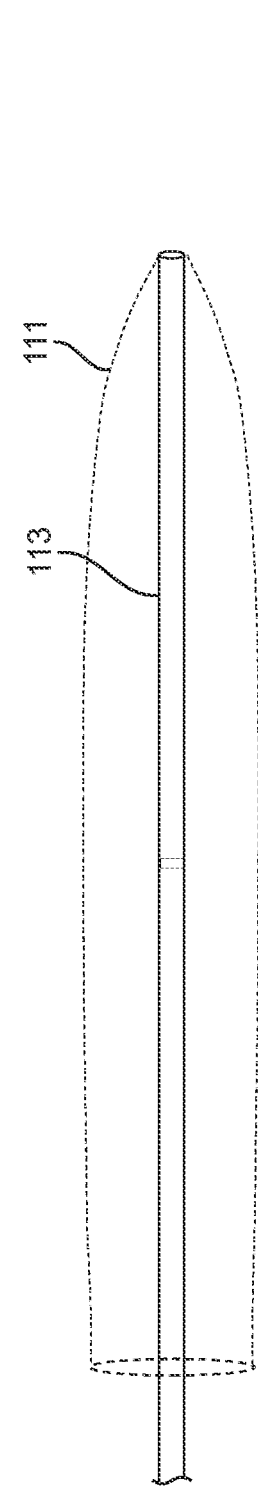
FIG. 1C1
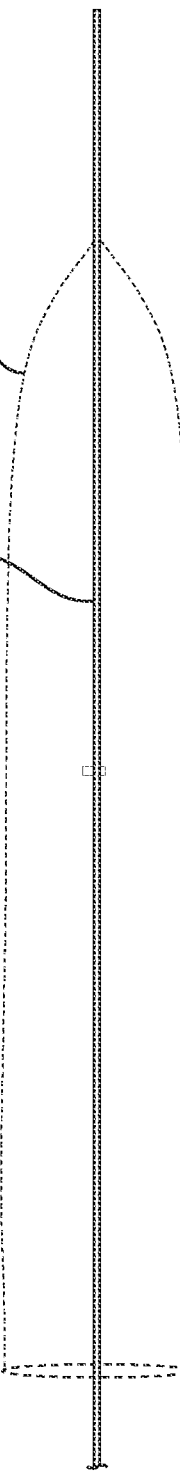
FIG. 1C2

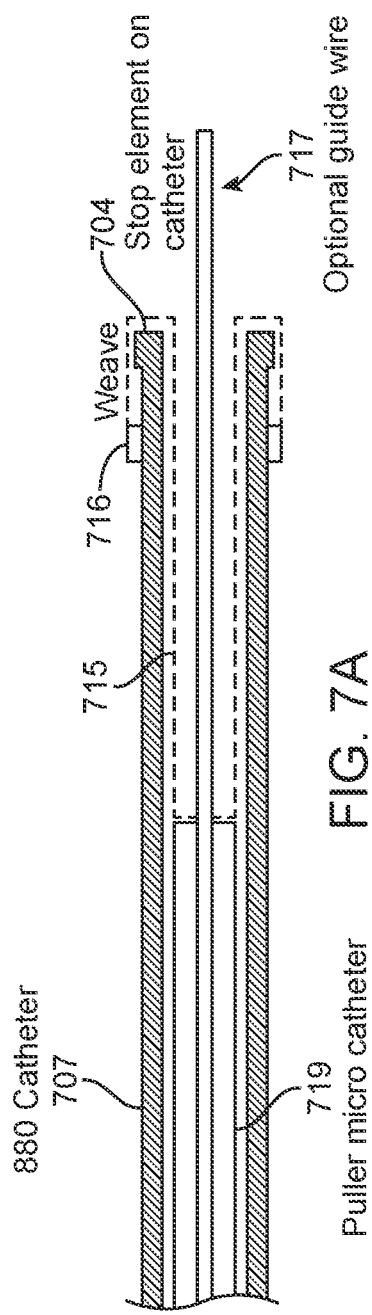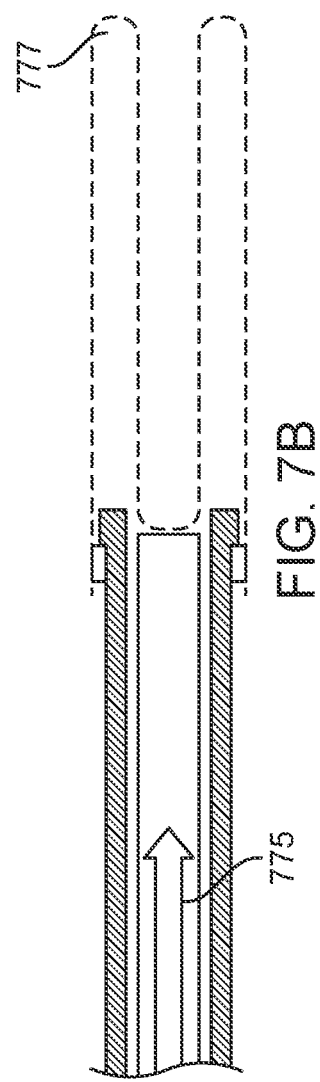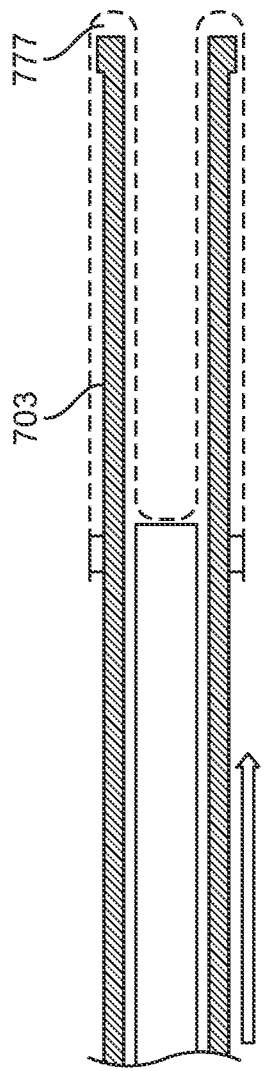

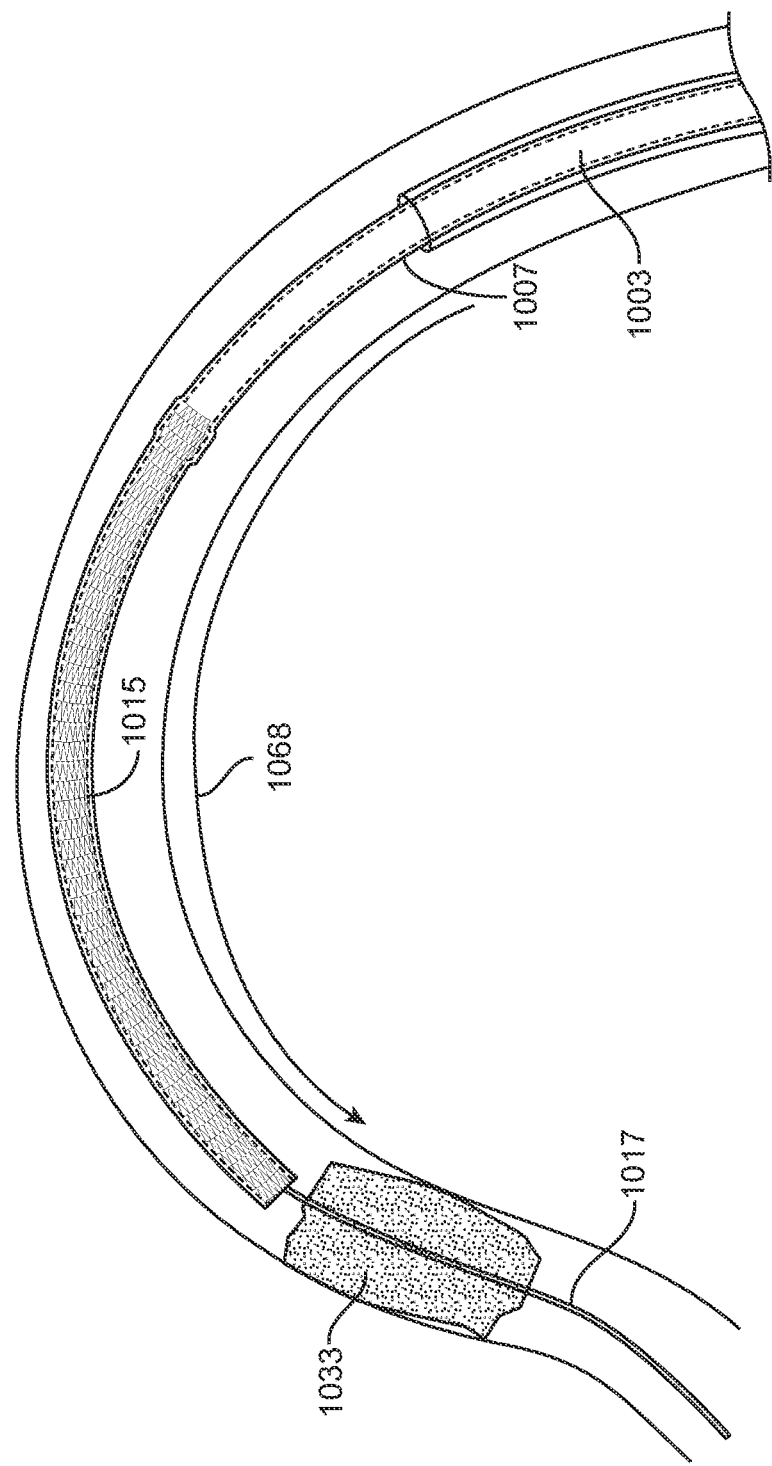

NiTi knit segment as a stop element

NiTi braid with exposed fingers

NiTi braid with exposed fingers
1403

Polymer stop
1401

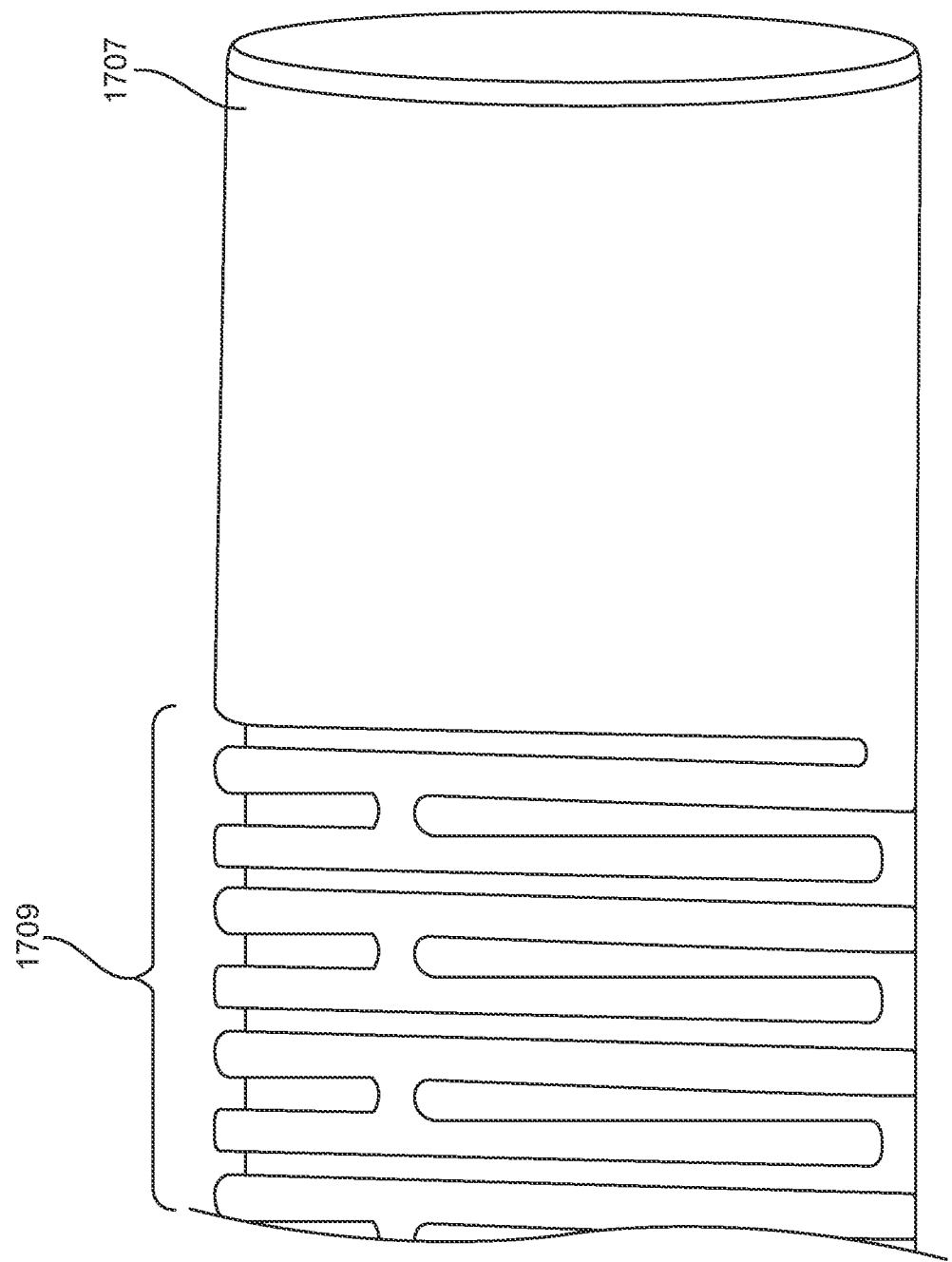

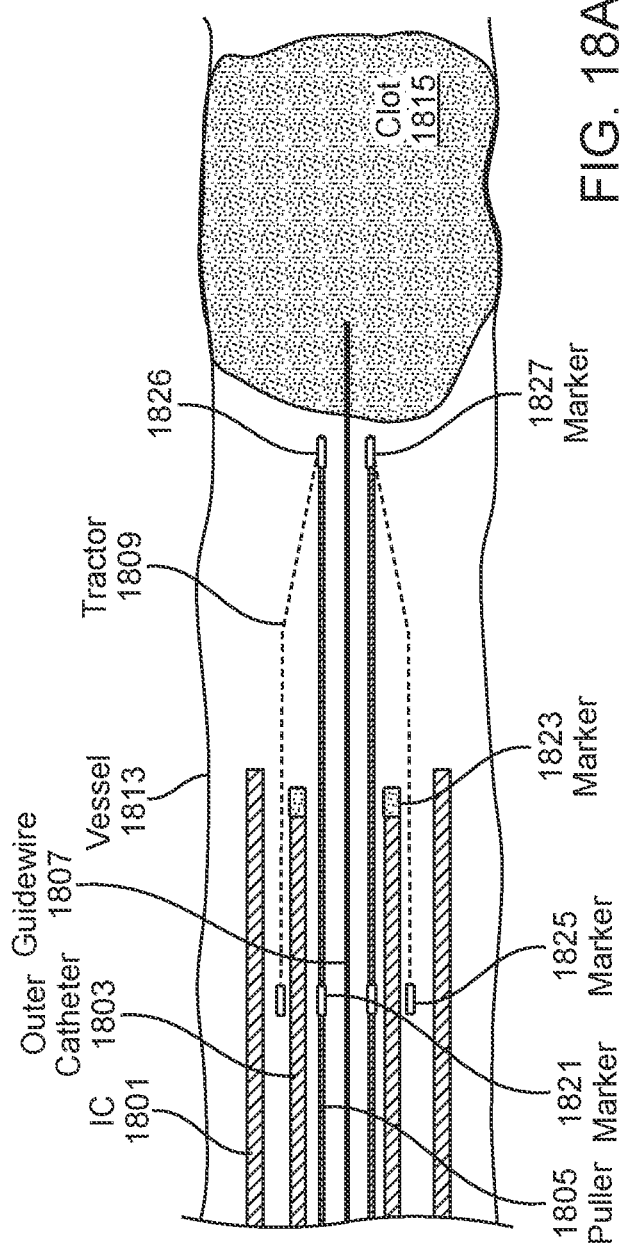
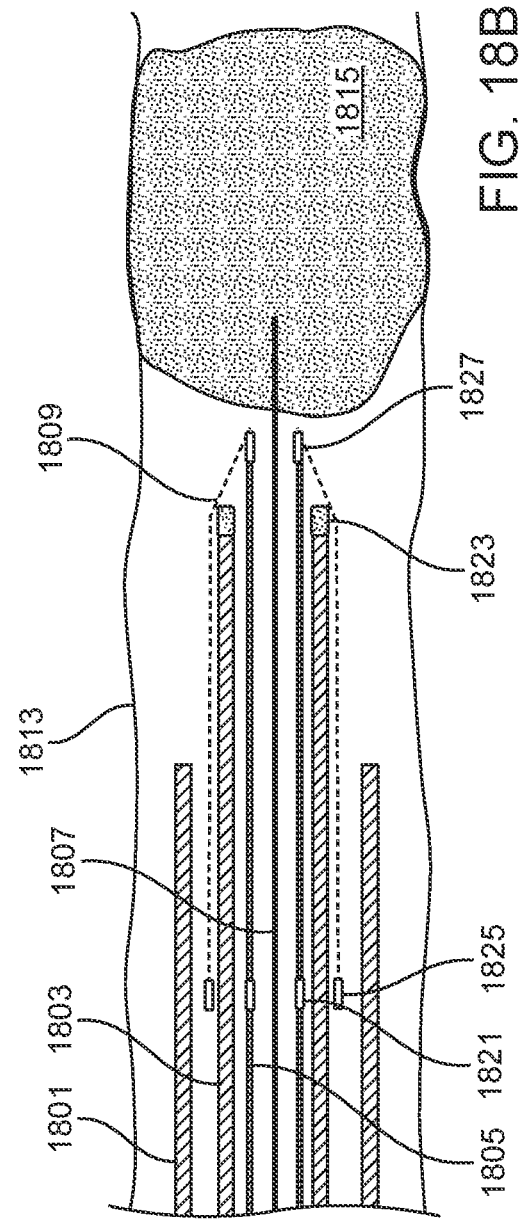

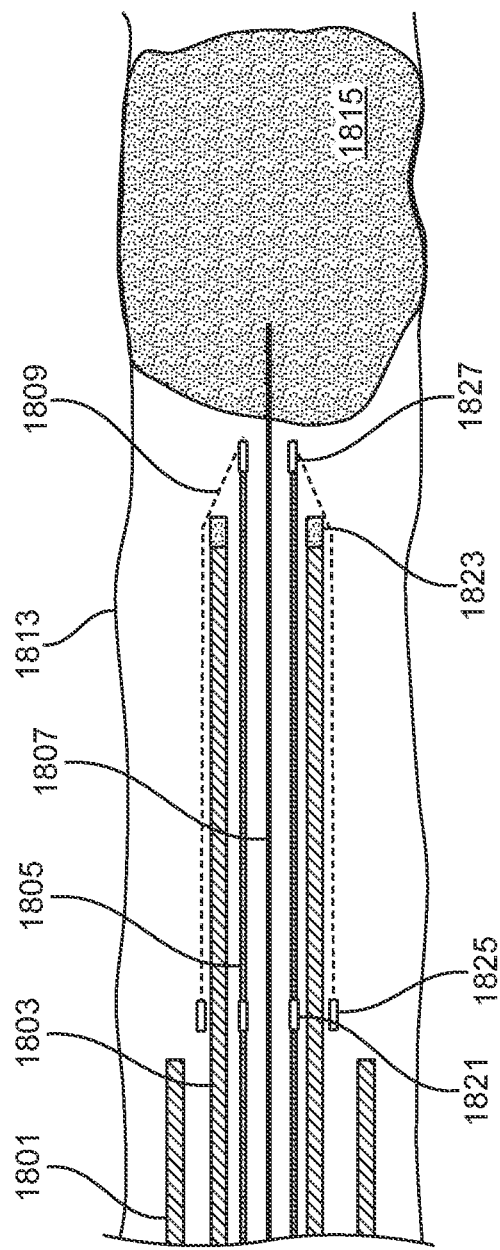
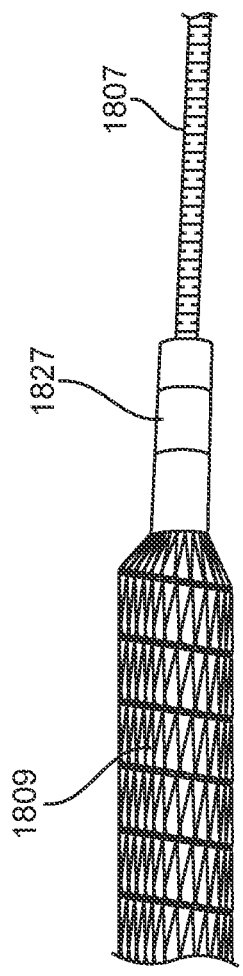
FIG. 18C
FIG. 18C1

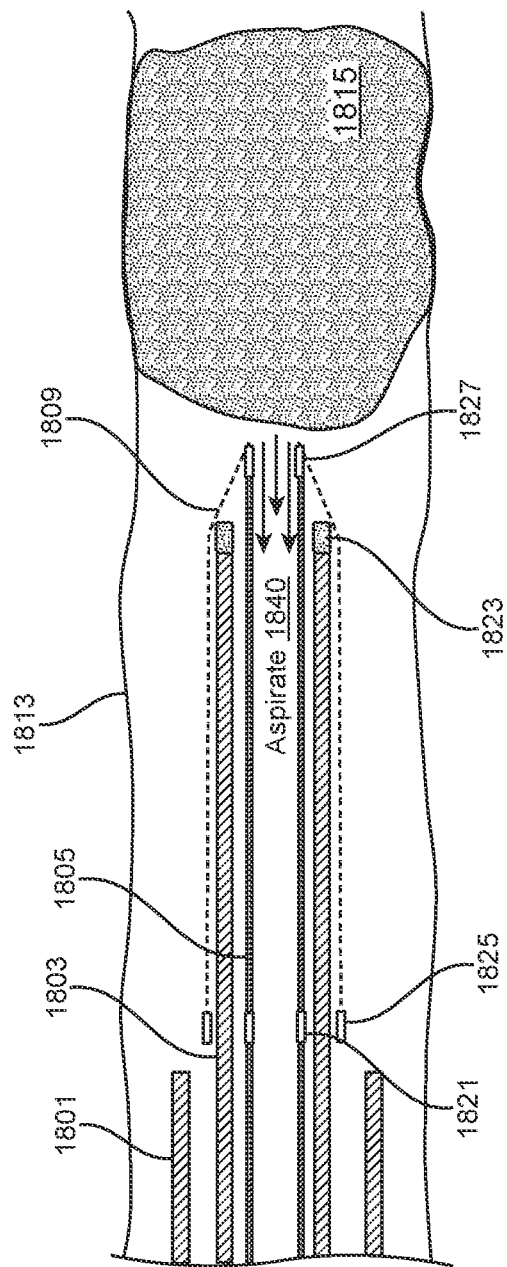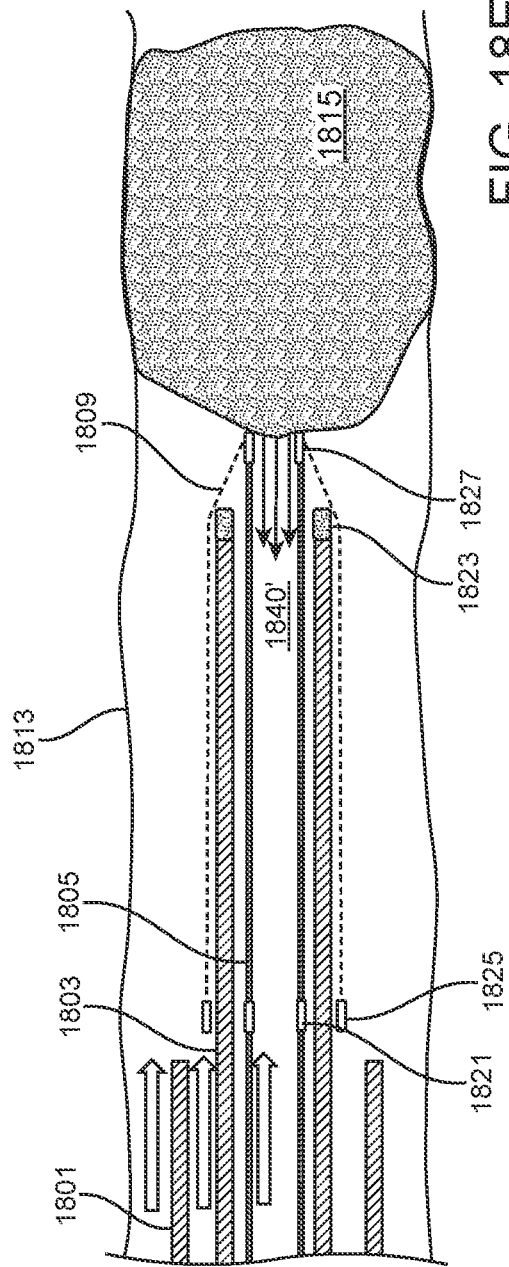

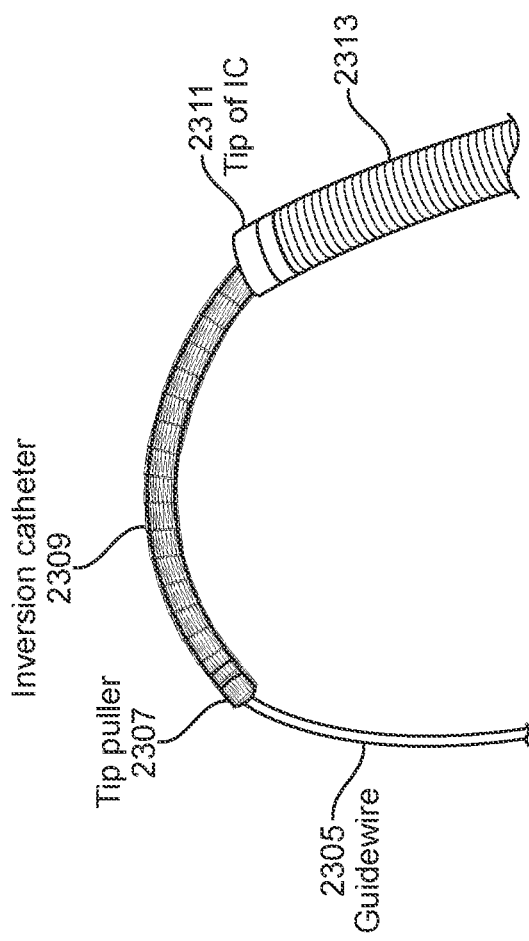
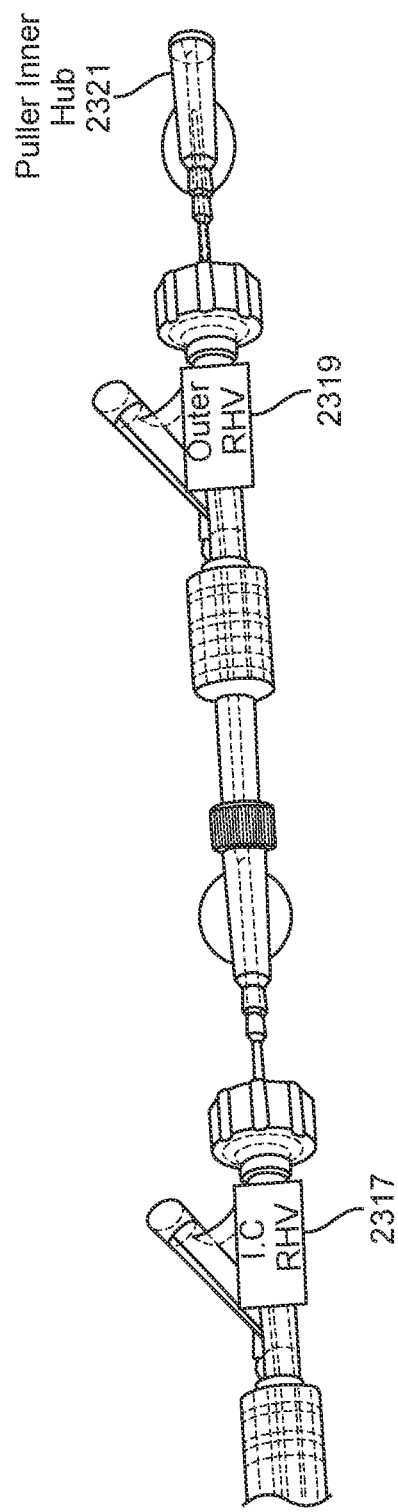
FIG. 23A
FIG. 23B

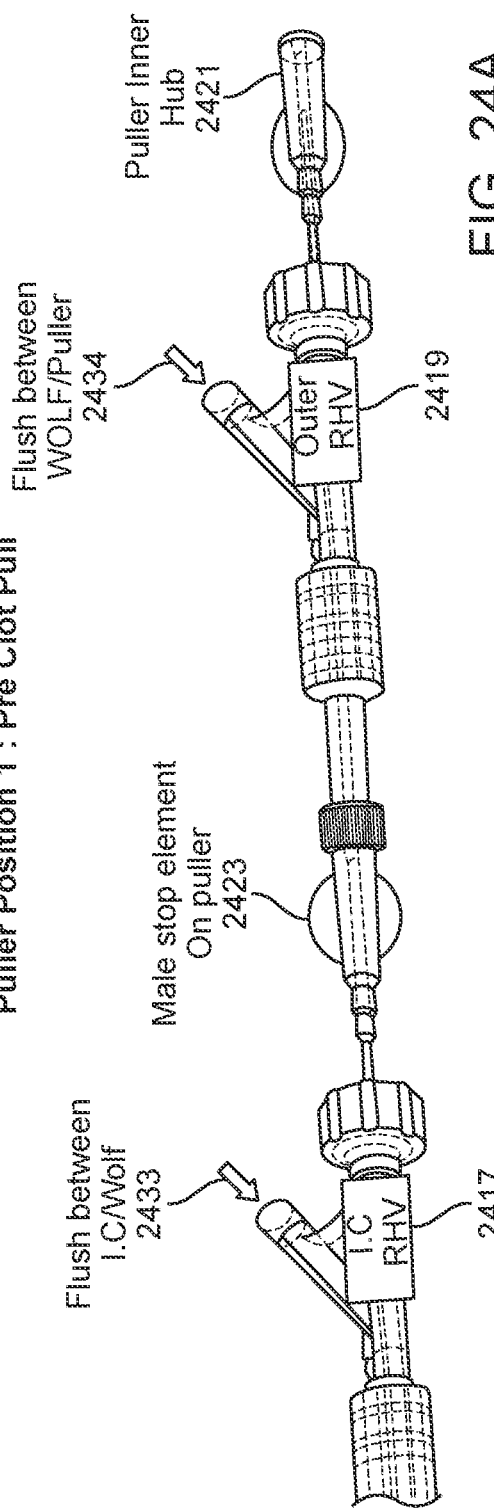
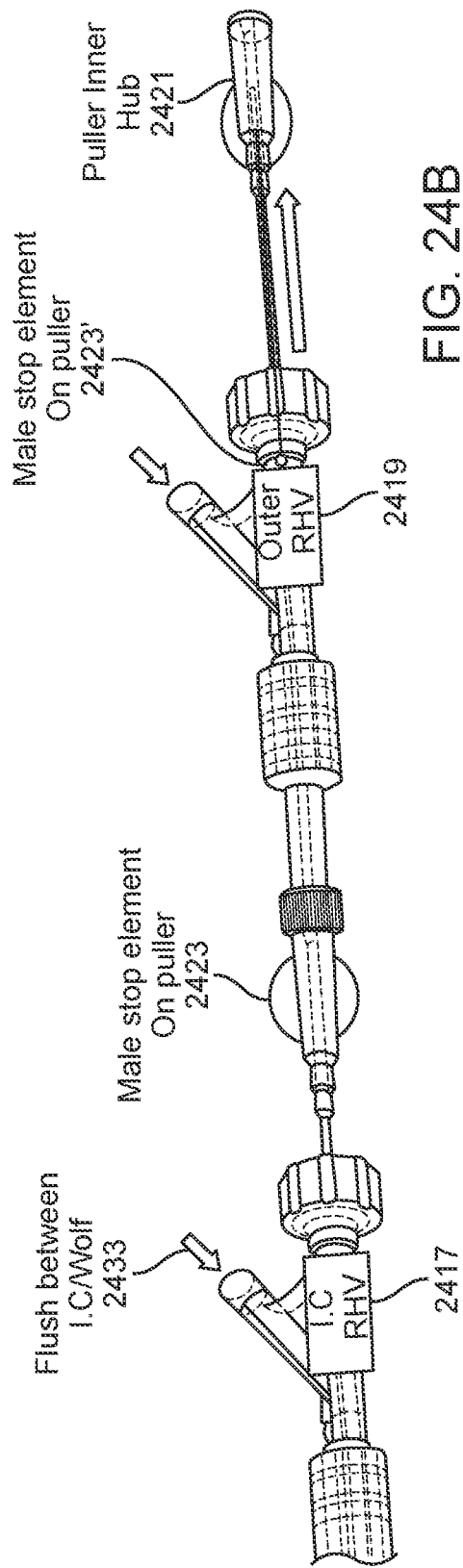

INVERTING THROMBECTOMY APPARATUSES HAVING ENHANCED TRACKING

RELATED APPLICATION DATA

This patent application is a continuation of U.S. Pat. No. 10,912,576, filed on Nov. 7, 2018, which claims priority to U.S. provisional patent application No. 62/583,803, filed on Nov. 9, 2017, entitled "INVERTING THROMBECTOMY APPARATUSES HAVING ENHANCED TRACKING"; and U.S. provisional patent application No. 62/664,822, filed on Apr. 30, 2018, entitled "INVERTING THROMBECTOMY APPARATUSES HAVING ENHANCED TRACKING".

This application is related to each of: U.S. Pat. No. 10,271,864, filed Oct. 11, 2016, entitled "Mechanical Thrombectomy Apparatuses and Methods"; U.S. Pat. No. 10,028,759, filed Apr. 25, 2017, entitled "Anti-Jamming and Macerating Thrombectomy Apparatuses and Methods"; U.S. Pat. No. 9,962,178, filed Apr. 25, 2017, entitled "Pre-loaded inverting tractor Thrombectomy Apparatuses and Methods"; U.S. Pat. No. 10,010,335, filed Apr. 25, 2017, entitled "Methods for Advancing Inverting Mechanical Thrombectomy Apparatuses in The Vasculature"; U.S. Pat. No. 10,512,478, filed Apr. 25, 2017, entitled "Clot-Engulfing Mechanical Thrombectomy Apparatuses and Methods of use"; and U.S. Pat. No. 10,517,624, filed Jun. 1, 2017, entitled "Inverting Thrombectomy Apparatuses And Methods." The foregoing patent applications are each herein incorporated by reference in their entirety.

FIELD

The apparatuses and methods described herein relate to mechanical removal of objects from within a body. In particular, described herein are mechanical thrombectomy apparatuses and methods.

BACKGROUND

Many vascular problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery. It is often desirable to remove tissue from the body in a minimally invasive manner as possible, so as not to damage other tissues. For example, removal of tissue, such as blood clots, from within a patient's vasculature may improve patient quality of life.

Mechanical thrombectomy devices may be particularly advantageous. There is a definite need for thrombectomy devices, and particularly a mechanical thrombectomy devices that can be easily and accurately delivered through the, often tortious, anatomy in the peripheral and central vasculature, then reliably deployed to remove clot material. Described herein are apparatuses (devices, systems and kit) and methods of using them that may address the needs and problems discussed above.

SUMMARY

Described herein are inverting tractor mechanical thrombectomy apparatuses (devices, systems, etc.) and methods of using and making them.

In particular, described herein are inverting tractor mechanical thrombectomy apparatuses that are configured to have improved tracking within even the most tortious vessels of the anatomy. These inverting tractor mechanical thrombectomy apparatuses may be referred to herein as mechanical thrombectomy apparatuses. The method and apparatuses described herein may include the use of a deliver catheter (e.g., "intermediate catheter") that is pre-loaded with the mechanical thrombectomy apparatus in a specific arrangement that provides enhances tracking, and methods of using them to reach, and remove, clot.

Also described herein are adaptations to mechanical thrombectomy apparatuses that allow them to remove particularly large clots without breaking or disrupting the clot, even if the rolling tractor portion of the mechanical thrombectomy apparatus is not able to pull additional clot into the apparatus.

Typically, the mechanical thrombectomy apparatuses described herein are inverting thrombectomy apparatuses (also referred to herein as inverting tractor thrombectomy apparatuses and inverting tube thrombectomy apparatuses) that include a flexible tube (e.g., tractor tube, tractor region, tractor portion, etc.) and an elongate inversion support catheter. The tractor tube generally comprises a flexible tube of material that inverts over itself as it rolls over a distal end opening of an elongate inversion support. The flexible tube may be formed of a knitted material, and may be configured (e.g., sized, oriented, etc.) to roll smoothly over the distal end opening of the elongate inversion support catheter. The flexible tube may be configured so that it is doubly biased, in order to prevent jamming and to grab and compress relatively large clots as it rolls and inverts into the elongate inversion support catheter at the distal end opening of the elongate inversion support catheter; the flexible tube may be biased so that it has an expanded (e.g., relaxed) un-inverted configuration having an outer diameter that is approximately the same or slightly larger than the inner diameter of the elongate inversion support catheter, which may be referred to as a second configuration of the flexible tube. The flexible tube may also be further biased so that it has an expanded (e.g., relaxed) inverted configuration (which may be referred to as a first configuration) having an inner and outer diameter that is larger than the outer diameter of the elongate inversion support catheter. The inner diameter in this first configuration may be greater than 1.2× (e.g., between 1.2× and 10×, between 1.2× and 8×, between 1.2× and 6×, between 1.2× and 5×, between 1.2× and 3×, etc.) the outer diameter of the inversion support catheter. Thus, when the flexible tube is placed in and over the distal end of the inversion support catheter, a first (inner) portion of the tractor tube is within the distal end of the elongate inversion support catheter in the un-inverted configuration and it is biased to expand towards (and in some configuration against) the inner diameter of the inversion support catheter; the region of the flexible tube that is inverted over the distal end opening of the inversion support catheter and extends proximally down the outside of the inversion support catheter is in an inverted configuration in which the inner diameter of the flexible tube is biased to be larger than the outer diameter of the inversion support catheter. This double-biased configuration may be a result of the weave pattern (e.g., knitting), and/or a shape setting of the material forming the tractor tube, which may be a shape memory material. As a result, the inverting portion of the flexible tube, where it rolls and inverts over itself at the distal end of the inversion support catheter may be prevented from collapsing on itself as the tractor tube is rolled and pulled into the inversion support catheter. In some variations this configuration may also result in a somewhat flattened (e.g., and in some cases "trumpet shaped") distal end face that is rolling over the distal end opening of the elongate inversion support catheter. The trumpet-shaped distal end may have a teardrop-shaped cross-section. In some variations, the distal end face of the flexible tube may be T-shaped.

Also described herein are variations in which the first configuration of the flexible tube on the outside of the inversion support catheter (which may be referred to herein as an elongate inversion support catheter) maybe flush or nearly flush with the outer diameter of the inversion support catheter, e.g., within 50%, 40%, 30%, 20%, etc. of the outer diameter of the inversion support catheter.

The flexible tube may be coupled to a puller that is within the lumen of the inversion support. The puller may be a wire, filament, rod or more preferably a catheter or tube (and may be referred to herein as a pull micro catheter or "PMC" for convenience). A guidewire may be passed through the flexible tube, and therefore through the inversion support and the tractor tube. As will be described herein, this may be used for positioning.

The inversion support catheter may be configured as a catheter having a distal end opening into which the tractor inverts. The flexible tube may invert and rolls back into itself and may be drawn into the inversion support in a conveyor-like motion; the outward-facing region rolls around to become an inward-facing region, e.g., within the lumen of the inversion support catheter. The rolling motion may thus draw a clot or other object within a vessel into the inversion support. The inversion support catheter may be shaped or configured to have a sufficient column strength to withstand the compressive pulling force of the flexible tube as it is drawn (and rolled, inverting) into the distal end of the inversion support catheter. The inversion support catheter may be slotted (e.g., may include a plurality of slots or openings) to provide increased flexibility as well as column strength. However, as will be described herein, many inversion support catheters may become less flexible (e.g., more rigid) when a compressive force is applied to the flexible tube, either as a result of pulling the flexible tube proximally, either from within the inversion support catheter, or from the outside of the inversion support catheter as the flexible tube brushes against the vessel and/or a delivery catheter when being driven distally towards a clot.

Thus, described herein are mechanical inverting thrombectomy apparatuses that are adapted to enhance tracking as the apparatus is positioned within the vessel by pushing it distally away from an insertion point into the body to the site of the thrombus. These apparatuses and methods may include pre-loading the apparatus within an intermediate catheter in a particular configuration allowing it to track more easily, as well as variations in which the flexible tube is held within the inversion support catheter and deployed near the clot. Finally, described herein are apparatus in which the flexible tube (e.g., mesh, weave, knit) to limit or prevent the application of a compressive force on the inversion support catheter that may otherwise reduce flexibility and maneuverability of the inversion support catheter.

Also described herein are methods and apparatuses for removing extensive clots, even when the flexible tube portion of the apparatus has been completely inverted, without breaking the clot and risking release of the clot back into the bloodstream where it could cause further harm.

For example, described herein are methods and apparatuses that use one or more vacuum sources that may be applied either or both when initially contacting a clot and/or when removing the clot after being completely or partially engulfed by the flexible tube (tractor) portion of the apparatuses described herein. These methods and apparatuses may be used with any of the apparatuses and methods described herein, for example, in above-incorporated U.S. application Ser. Nos. 15/291,015 and 15/496,570.

A method of removing a clot from a vessel may include: advancing an inverting tube apparatus through a vessel until a distal end of the inverting tube apparatus is proximate to a clot, wherein the inverting tube apparatus comprises an intermediate catheter, an inversion support catheter within a lumen of the intermediate catheter, a puller catheter within a lumen of the elongate support catheter, and a flexible tube having a first end coupled at a distal end region of the puller catheter, wherein flexible tube inverts over a distal end of the inversion support catheter and extends proximally between the intermediate catheter and the inversion support catheter; advancing the puller catheter distally so that a distal face of puller catheter extends distally from the inverting tube apparatus; applying a vacuum through the puller catheter to engage the clot with the distal face of the puller catheter; and pulling the puller catheter proximally to roll the flexible tube over a distal end of the inversion support catheter so that the flexible tube inverts over the distal end of the inversion support catheter captures the clot and pulls the clot proximally into the inversion support catheter.

The inverting tube apparatus (e.g., a mechanical thrombectomy apparatus) may be inserted through a vessel such as a blood vessel, artery, etc., until a distal end, or a distal-most end, of the inverting tube apparatus is proximate to a clot. The clot may be immediately adjacent to the end of the apparatus, or it may be within a few cm (e.g., within 1 cm, within 2 cm, within 3 cm, within 4 cm, etc.). This may be detected by visualization, such as fluoroscopy. Thus, the apparatuses described herein may include one or more markers for visualization. Contrast may be used to visualize the clot and/or may be released from the apparatus. The apparatus may be deployed in a pre-loaded/pre-assembled configuration, as will be described in more detail below.

In any of these methods described herein, the flexible tube may be knitted and/or the apparatus may be configured with the opening into the vacuum lumen (e.g., through the puller catheter) at the distal-most end of the device, so that the flexible tube extends behind (proximal) the distal-facing end of the puller catheter. For example, the method of removing a clot from a vessel may include: advancing an inverting tube apparatus through a vessel until a distal end of the inverting tube apparatus is proximate to a clot, wherein the inverting tube apparatus comprises an intermediate catheter, an inversion support catheter within a lumen of the intermediate catheter, a puller catheter within a lumen of the elongate support catheter, and a knitted tube having a first end coupled at a distal end region of the puller catheter, wherein knitted tube inverts over a distal end of the inversion support catheter and extends proximally between the intermediate catheter and the inversion support catheter, further wherein the knitted tube comprises a filament that is knitted to form a plurality of interlocking loop stitches; advancing the puller catheter distally so that a distal face of puller catheter extends distally from the inverting tube apparatus further than the knitted tube; applying a vacuum through the puller catheter to engage the clot with the distal face of the puller catheter; and pulling the puller catheter proximally to roll the knitted tube over a distal end of the inversion support catheter so that the knitted tube inverts over the distal end of the inversion support catheter, captures the clot, and pulls the clot proximally into the inversion support catheter.

Thus, in any of these variations, advancing the puller catheter distally may include advancing the puller catheter so that a distal face of puller catheter extends distally from the inverting tube apparatus further than the flexible tube. Advancing the inverting tube apparatus may comprise advancing over a guidewire passing through the puller catheter of the inverting tube apparatus. Advancing the puller catheter distally may further comprise advancing the elongate support catheter distally between the flexible tube and the puller catheter. Advancing the inverting tube apparatus comprises advancing the puller and flexible tube distally in the vessel, wherein the flexible tube extends proximally from the distal end region and further wherein the flexible tube comprises a knitted tube comprising a filament that is knitted to form a plurality of interlocking loop stitches.

Any of these methods may also include withdrawing the intermediate catheter proximally before or while advancing the puller catheter distally.

In general, applying the vacuum may include applying the vacuum through the puller catheter and around a guidewire within the puller catheter. When a guidewire is used, it may be threaded through the puller catheter; the vacuum may be applied with the guidewire present or it may be removed first. For example, the method may include removing a guidewire from out of the puller catheter prior to applying the vacuum.

The vacuum (suction) applied may also be used to help guide the therapy and operation of the apparatus. For example, any of these methods may include observing flow from the puller catheter when applying the vacuum to determine when the clot is engaged with the distal face of the puller catheter. The vacuum may be applied concurrently with advancing the puller catheter distally; once the clot is contacted (which may be detected, e.g., by monitoring the vacuum resistance and/or the flow through the puller catheter), the vacuum may be sustained, reduced, or turned off.

In some variations, vacuum may be applied through the intermediate catheter while withdrawing the puller catheter and puller proximally into the intermediate catheter.

Also described herein are methods and apparatus for removing longer/larger clots from a vessel. In particular, described herein are methods and apparatuses for removing clots that are longer than the flexible tube portion of the apparatus.

For example, described herein are methods of removing a large clot from a vessel, the method comprising: advancing an inverting tube apparatus through a vessel until a distal end of the inverting tube apparatus is proximate to a clot, wherein the inverting tube apparatus comprises an intermediate catheter, an inversion support catheter within a lumen of the intermediate catheter, a puller within a lumen of the inversion support catheter, and a flexible tube having a first end coupled at a distal end region of the puller and a second end that is free to move over an outer surface of the inversion support catheter, wherein the flexible tube extends proximally between the intermediate catheter and the inversion support catheter; pulling the puller proximally to roll the flexible tube over the distal end of the inversion support catheter so that the flexible tube inverts over a distal end of the inversion support catheter, captures the clot, and pulls the clot proximally into the inversion support catheter, wherein the second end reaches the distal end of the inversion support catheter while a portion of the clot extends distally from the inversion support catheter; and withdrawing, after the second end reaches the distal end of the inversion support catheter, the inversion support catheter and puller with the clot attached proximally into the intermediate catheter until the entire clot is within the intermediate catheter.

For example, a method of removing a clot from a vessel may include: advancing an inverting tube apparatus through a vessel until a distal end of the inverting tube apparatus is proximate to a clot, wherein the inverting tube apparatus comprises an intermediate catheter, an inversion support catheter within a lumen of the intermediate catheter, a puller within a lumen of the elongate support catheter, and a flexible tube having a first end coupled at a distal end region of the puller and a second end comprising a cuff that is less flexible that a region of the flexible tube adjacent to the cuff, wherein the flexible tube extends proximally between the intermediate catheter and the inversion support catheter; pulling the puller proximally to roll the flexible tube over the distal end of the inversion support catheter so that the flexible tube inverts over a distal end of the inversion support catheter, captures the clot, and pulls the clot proximally into the inversion support catheter; stopping pulling the puller from moving proximally when or before the cuff reaches the distal end of the inversion support catheter; moving the intermediate catheter distally past the cuff to invert the cuff over the distal end of the inversion support catheter; and withdrawing the inversion support catheter and puller with the clot attached proximally into the intermediate catheter.

A large clot may be a clot that is typically longer than the capacity of the apparatus to hold within the flexible tube. This is described in greater detail herein, but may be, e.g., a 12:1 ratio (where, for every 12 cm of, e.g., woven, flexible tube, 1 cm of length of clot may be contained within the woven flexible tube). In general, large clots may have a large diameter and/or a long length. Longer clots may include clots having a length that is about 0.5 m or longer (e.g., about 1 cm or longer, about 2 cm or longer, about 3 cm or longer, about 4 cm or longer, about 5 cm or longer, etc.).

In any of the methods described herein, the second end may reach the distal end of the inversion support catheter while a portion of the clot extends distally from the inversion support catheter so that at least a portion of the clot extends out of the flexible tube. The second end of the flexible tube may be prevented (stopped) from inverting over the end of the inversion support catheter, or it may be inverted and flipped (e.g., by advancing the intermediate catheter) in a non-traumatic way that prevents or limits the risk of breaking/tearing/disrupting the clot.

In any of these variations, suction may be applied through the inverting tube apparatus (e.g., through the intermediate catheter and/or the inversion support catheter) when withdrawing the inversion support catheter and puller with the clot attached proximally into the intermediate catheter.

The second end of the flexible tube may comprise a cuff that is less flexible that a region of the tube adjacent to the cuff. As will be described in more detail below, the cuff may be formed as a material attached to or applied onto/over the end of the flexible tube. For example, the second end of the flexible tube may comprise a cuff formed of a polymeric material applied onto/over the knitted tube. The cuff may be slit or cut (e.g., all or partially along its length) to provide some flexibility when pulling over or around the end of the tube. For example, the cuff may include longitudinal slits along its length. The cuff may have a durometer that is greater than the durometer of the flexible tube (e.g., knitted tube). The cuff, in some variations, is thicker than the flexible tube. In any of the variations described herein, the cuff may be radiopaque (e.g., by including a radiopaque material, such as platinum) on or within the cuff.

As mentioned, the apparatus may be configured so that the end (e.g., the second end) of the flexible tube may be prevented from inverting and rolling over the distal end of the inversion support catheter by simply pulling proximally on the puller. Thus, in any of these variations, the intermediate catheter may be configured to push the cuff over the distal end of the inversion support catheter when the intermediate catheter is advanced distally past the cuff As mentioned, any of these methods may include limiting the puller to stop the puller from moving proximally when or before the cuff reaches the distal end of the inversion support catheter. The limiting may be achieved by the cuff or other member (e.g., protrusion) engaging a stop (e.g., on the inversion support catheter) or the like. Any of these methods may include moving the intermediate catheter distally past the cuff to invert the cuff over the distal end of the inversion support catheter.

Specifically described herein are methods and apparatuses using flexible knitted tubes (tractors) as part of any of the mechanical thrombectomy apparatuses described herein. For example, the knitted flexible tubes may be configured to have stitch lengths that assist in capturing of clot within the vessel, even where the vessel has a larger inner diameter than the outer diameter of the flexible tube in an expanded configuration outside of the inversion support catheter. In particular, apparatuses in which the stich length is within a range of lengths that may be set by the dimension of the vessel (e.g., blood vessel, artery, peripheral vessel, etc.) and/or the outer diameter of the inversion support catheter. For example, a stitch length may be between about 0.5 mm and 10 mm and/or may be selected based on the dimension of the vessel into which the apparatus is to be operated to remove a clot.

For example, described herein are method of removing a clot from a vessel having an inner diameter (ID), the method comprising: advancing an inverting tube apparatus through the vessel until a distal end of the inverting tube apparatus is proximate to a clot, wherein the inverting tube apparatus comprises an intermediate catheter, an inversion support catheter within a lumen of the intermediate catheter, a puller within a lumen of the support catheter, and a knitted tube having a first end coupled at a distal end region of the puller and a second end, wherein the knitted tube extends between the intermediate catheter and the inversion support catheter; further wherein the knitted tube comprises a filament knitted to form a plurality of interlocking loop stitches, wherein each loop stitch has a stitch length that is between the difference of 25% of the ID and one half the outer diameter (OD) of the inversion support catheter and 65% of the ID and one half of the OD of the inversion support catheter; pulling the puller proximally to roll the knitted tube over the distal end of the inversion support catheter so that the knitted tube inverts over a distal end of the inversion support catheter driving the loop stitches outward, captures the clot, and pulls the clot proximally into the inversion support catheter.

Any of these methods may be used in particular with apparatuses in which the flexible tube is configured to remain relative snug on the inversion support catheter (e.g., within 50% (e.g., 40%, 30%, 25%, 20%, 15%, 10%, etc.) of the outer diameter of the inversion support catheter in the expanded (unconstrained) first configuration. In general, these apparatuses may expand at or near the distal-facing ends of the flexible tube, where the tube is inverting over itself, but may not be expanded at more proximal regions. This may form the T-shaped, Y-shaped, and/or trumpet-shaped distal end faces of the flexible tubes described herein. For example, in some variations, the knitted tube extends over the inversion support catheter with an inner diameter that is within 20% of the OD the inversion support catheter.

The second end of the knitted tube may comprise a cuff that is less flexible that a region of the knitted tube adjacent to the cuff, as described above and further herein. Alternatively, or additionally, the knitted tube may be shape-set to have a narrower region at the second end region (near the second end) of the flexible tube.

As mentioned above, in general, each loop stitch may have a stitch length that is between the difference of 25% of the ID and one half the outer diameter (OD) of the inversion support catheter and 65% of the ID and one half of the OD of the inversion support catheter. For example, each loop stitch may have a stitch length that is between the difference of 30% of the ID and one half the OD of the inversion support catheter and 60% of the ID and one half of the OD of the inversion support catheter (e.g., between the difference of 35% of the ID and one half the OD of the inversion support catheter and 50% of the ID and one half of the OD of the inversion support catheter, between the difference of 40% of the ID and one half the OD of the inversion support catheter and 45% of the ID and one half of the OD of the inversion support catheter, between the difference of 25% of the ID and one half the OD of the inversion support catheter and 45% of the ID and one half of the OD of the inversion support catheter, etc.). The stitch length may refer to the longitudinal (in the proximal-to-distal axis, which may curve or bend) of the knitted tube. The knitted tube may be formed of one or more filaments (or filament bundles) that are knitted into the tube to form interlocking links (loop stitches). The filament material may be relatively stiff, such as a wire, e.g., Nitinol wire, that when knitted has a material flexibility. The knit may be coated with a material (e.g., a lubricious material, etc.). Examples of knits are illustrated in, e.g., U.S. application Ser. No. 15/496,570, filed on Apr. 25, 2017 ("Anti-Jamming and Macerating Thrombectomy Apparatuses and methods"), previously incorporated by reference in its entirety.

For example, an inverting tube apparatus for removing a clot from a vessel may include: an intermediate catheter; an inversion support catheter within a lumen of the intermediate catheter; a puller within a lumen of the elongate support catheter; and a knitted tube extending over the inversion support catheter, the knitted tube having a first end coupled at a distal end region of the puller and a second end that is free, wherein the knitted tube is configure to be pulled proximally into the inversion support catheter by pulling the puller proximally so that the knitted tube rolls and inverts over a distal end of the inversion support catheter; further wherein the knitted tube comprises a filament knitted to form a plurality of interlocking loop stitches, wherein each loop stitch has a stitch length that is between 0.5 mm and 10 mm.

As mentioned, the knitted tube may extend over the inversion support catheter with an inner diameter that is within 20% (e.g., within about 10%, 15%, 20%, 25%, 30%, 40%, etc.) of the outer diameter of the inversion support catheter (e.g., relatively snugly to or against the inversion support catheter). The second end of the knitted tube may comprise a cuff that is less flexible that a region of the knitted tube adjacent to the cuff.

Any of the methods and apparatuses described herein may include an expanded flexible tube portion that expands outward less than the diameter of the vessel over much (e.g., greater than about 50%, about 60%, about 70%, about 75%, about 80%, about 90%, etc.) of its length while having an expanded second end region that has a much smaller diameter near this second end region (e.g., having a diameter that is within about 10%, 15%, 20%, 25%, 30%, 40%, etc. of the inversion support catheter. This configuration may allow even larger-diameter clots (e.g., from the peripheral vasculature) to be engulfed and safely removed with apparatuses having a much narrower diameter than the vessels in which the clots are located.

For example, described herein are inverting tube apparatus for removing a clot from a vessel, the apparatus comprising: an inversion support catheter; a puller within a lumen of the inversion support catheter; and a knitted tube extending over the inversion support catheter in a first configuration, the knitted tube having a first end coupled to a distal end region of the puller, and a second end that is free to move relative to the inserting support catheter, wherein the knitted tube is configure to be pulled proximally into the inversion support catheter by pulling the puller proximally so that the knitted tube rolls and inverts over a distal end of the inversion support catheter into a second configuration within the inversion support catheter; further wherein the knitted tube in the first configuration has an expanded outer diameter that is between 0.5 mm and 12 mm for a first region of the knitted tube that is adjacent to the first end, and the knitted tube in the second configuration has an inner diameter that is greater than 30% of an inner diameter of the inversion support catheter, and wherein a second region of the knitted tube adjacent to the second end has an expanded outer diameter that is less than the expanded outer diameter of the region of the knitted tube adjacent to the first end and within 20% of an outer diameter of the inversion support catheter.

As mentioned, the knitted tube in the first configuration may have an expanded outer diameter (unconstrained) that is between 0.5 mm and 12 mm; in some variations this expanded outer diameter is between 0.5 mm and 15 mm, e.g., between about 0.5 mm and about 14 mm, between about 0.5 mm and about 13 mm, between about 0.5 mm and about 11 mm, between about 0.5 mm and about 10 mm, between about 0.5 mm and about 9 mm, between about 0.5 mm and about 8 mm, between about 3 mm and about 15 mm, between about 4 mm and about 15 mm, between about 5 mm and about 15 mm, between about 3 mm and about 12 mm, between about 4 mm and about 12 mm, between about 5 mm and about 12 mm, between about 3 mm and about 10 mm, between about 4 mm and about 10 mm, between about 5 mm and about 10 mm, etc.

Any of the apparatuses described herein may include a cuff at the second end, wherein the cuff has a stiffness that is greater than a region of the knitted tube adjacent to the cuff. Alternatively, or additionally, any of these apparatuses may include a stop configured to limit the travel of the knitted tube so that the second end does not roll and invert over the distal end of the inversion support catheter.

The knitted tube may be shape set so that the first configuration has the outer diameter between, e.g., 0.5 mm and 10 mm for the region of the kitted tube adjacent to the first end, and the knitted tube in the second configuration has an inner diameter that is greater than, e.g., about 30% (e.g., about 40%, about 50%, about 60%, etc.) of the inner diameter of the inversion support catheter.

The first region of the kitted tube (having the larger expanded diameter) may be any appropriate length (e.g., at least about 0.5 cm, about 1 cm, about 2 cm, about 3 cm, about 4 cm, about 5 cm, about 6 cm, about 7 cm, about 8 cm, about 9 cm, about 10 cm, etc.). Similarly, the second region (having the narrower expanded diameter) may be any appropriate length (e.g., at least about 0.5 cm, about 1 cm, about 2 cm, about 3 cm, about 4 cm, about 5 cm, etc.).

The knitted tube may comprise a filament knitted to form a plurality of interlocking loop stitches, wherein each loop stitch has a stitch length that is between a predetermined range (e.g., between about 0.5 mm and 8 mm, about 0.5 to 10 mm, about 0.5 mm to 12 mm, about 0.5 mm to 14 mm, etc.). This may permit, for example, at a region of the knitted tube that is inverting from the first configuration to the second configuration, a sub-set of the plurality of loop stitches forming the knitted tube may extend proud from the long axis of the knitted tube by between 0.5 mm and 10 mm (e.g., between about 0.3 mm and about 8 mm, between about 0.5 mm and about 8 mm, between about 0.5 mm and about 7 mm, between about 0.5 mm and about 6 mm, greater than about 1 mm, greater than about 2 mm, greater than about 3 mm, greater than about 4 mm, greater than about 5 mm, etc.) as the knitted tube inverts.

Any of these apparatuses may include an intermediate catheter having a lumen as described herein. The inversion support catheter may be within the lumen of the intermediate support catheter and may be extended distally from the intermediate catheter to deploy the knitted tube so that the flexible tube may expand into the first configuration.

As mentioned, described herein are methods for removing a clot from a vessel a larger diameter (and therefore a larger clot diameter) than even the expanded flexible tube of the apparatus. For example, described herein are methods of removing a clot from a vessel having an inner diameter (ID) comprising: advancing an inverting tube apparatus through the vessel until a distal end of the inverting tube apparatus is proximate to a clot, wherein the inverting tube apparatus comprises an inversion support catheter, a puller within a lumen of the support catheter, and a knitted tube having a first end coupled to a distal end region of the puller, and a second end that is free to move relative to the inserting support catheter, wherein the knitted tube comprises a filament knitted to form a plurality of interlocking loop stitches, wherein each loop stitch has a stitch length; expanding the knitted tube to a first configuration along an outer surface of the inverting tube catheter to an outer diameter that between 10% and 80% of an inner diameter of the vessel for a first region of the knitted tube that is adjacent to the first end, wherein the knitted tube has a second configuration within the inverting tube catheter having an inner diameter that is greater than 30% of an inner diameter of the inversion support catheter, and wherein a second region of the knitted tube adjacent to the second end has an expanded outer diameter that is less than the expanded outer diameter of the first configuration; pulling the puller proximally within the inversion support catheter to roll the knitted tube over the distal end of the inversion support catheter so that the knitted tube inverts over a distal end of the inversion support catheter, driving the loop stitches outward from the kitted tube by between 0.5 and 10 mm; capturing the clot with the knitted tube; and pulling the clot proximally into the inversion support catheter.

These methods may also include sliding the second end along the length of the inversion support catheter when pulling the puller proximally, wherein the second end comprises a cuff having a stiffness that is greater than a region of the knitted tube adjacent to the cuff.

Any of these methods may include limiting travel of the knitted tube so that the second end does not roll and invert over the distal end of the inversion support catheter when pulling the puller proximally.

In general, advancing may comprise advancing over a guidewire.

Expanding of the flexible tube (e.g., knitted tube) may comprise exposing the knitted tube from out of an intermediate catheter, wherein the inversion support catheter is within a lumen of the intermediate support catheter.

BRIEF DESCRIPTION OF THE DRAWINGS

The features and aspects of the various embodiments of the disclosed inventions are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A illustrates one example of a delivery catheter ("intermediate catheter" or I.C.) that may be used with a mechanical thrombectomy apparatus as described herein.

FIGS. 1B-1C2 illustrate components of a mechanical (e.g., inverting tractor) thrombectomy apparatus; FIG. 1B shows an example of an elongate inversion support catheter that is configured to include a plurality of slots (shown here as transverse slots) arranged along the catheter in order to enhance flexibility of the elongate inversion support catheter while providing sufficient column strength to resist buckling as the tractor tube is drawn proximally to invert. The slot pattern of FIG. 1B is intended as a single example only. Other slot/cut-out patterns may be used. FIGS. 1C1 and 1C2 show a tractor tube inverted (e.g., in an inverted configuration) over a puller; in FIG. 1C1 the puller is a puller catheter (PMC) while in FIG. 1C2 the puller is a guidewire. The tractor tube is shown schematically and may be a knitted, woven, or braided material.

FIG. 2A shows the assembled apparatus in which the tractor tube is coupled to the puller and within the elongate inversion catheter with the tractor tube inverting over the distal end of the elongate inversion catheter. FIG. 2B shows the apparatus of FIG. 2A delivered within a vessel near a clot. FIG. 2C shows the operation of the apparatus to withdraw the clot by pulling proximally on the tractor tube from within the elongate inversion support catheter so that the tractor tube is pulled to roll over and evert from the inverted configuration on the outside of the distal end of the elongate inversion support catheter into the un-inverted configuration within the elongate inversion support catheter, pulling the clot with it.

FIGS. 7A-7C illustrate one example of an inverting tractor mechanical thrombectomy apparatus in which the apparatus is configured for delivery of the tractor tube within the elongate inversion support catheter so that it may later be deployed (as illustrated in FIGS. 7A-7C) to move the tractor tube portion so that it is inverted over the elongate inversion support catheter distal end.

FIGS. 10A-10D illustrate another example of a method of delivering and deploying an inverting tractor mechanical thrombectomy apparatus pre-loaded into an intermediate catheter such as the one shown in FIGS. 3A-3B.

In FIG. 12A the tractor tube has a distal end region that is non-compliant and configured so that it cannot invert over the distal end of the elongate inversion support catheter.

In FIG. 14 a polymer strop is shown. In FIG. 14B a Nitinol braid stop has exposed filaments ("fingers") that prevent proximal sliding of the tractor tube. FIG. 14C shows another example of a Nitinol braid stop has exposed filaments ("fingers") that prevent proximal sliding of the tractor tube. FIG. 14D shows a Nitinol knit segment configured as a stop to prevent proximal sliding of the tractor tube during delivery.

In FIG. 16A, a 48-end braid forms an annular garage for holding the end of the tractor tube so that it remains in a compressed configuration along the outer surface of the elongate inversion support catheter. In FIG. 16B, the apparatus includes a 10 mm long braided region (similar to that shown in FIG. 15A, housing the end of the knitted tractor tube and preventing it from extending proximally and applying compressive forces on the distal end of the elongate inversion support catheter.

FIG. 17 is an example of one variations of an elongate inversion support catheter having a high column strength in compression, but a high flexibility when not under compression. In FIG. 17, the elongate inversion support catheter includes a plurality of slots or cut-our regions arranged approximately transverse to the elongate length (e.g., long axis). Any of these devices may also include a marker (e.g., platinum, or other radiopaque material) allowing visualization of the distal end region of the elongate inversion support catheter.

FIGS. 18A-18J illustrate a method of removing a clot from a vessel as described herein, in which a vacuum (suction) may be applied through the puller to make and confirm initial contact with the clot. In FIG. 18A, the apparatus is distally advanced over a guidewire adjacent to the clot. The apparatus may initially be in a tracking configuration as shown and discussed, in which the outer (inversion support) catheter is retracted into the lumen of the intermediate catheter while the puller (puller catheter) with the attached flexible tube extending proximally from the distal end, is tracked over the guidewire. In FIG. 18B, the apparatus is changed to a clot-grabbing configuration in which the inversion support catheter is extended towards the distal end of the apparatus, though still proximal to the puller distal end. The intermediate catheter may also optionally be withdrawn proximally, as shown in FIG. 18C, which in some variations (not shown in FIG. 18A-18J) may allow the flexible tube to expand outwards. FIG. 18C1 shows an example of a prototype device corresponding to FIG. 18C. Once in position, suction may be applied through the puller catheter, as shown in FIG. 18D. This focal suction may be applied while advancing the apparatus distally to engage the clot, as shown in FIG. 18E. The guidewire may be left in place or optionally removed (as shown in FIGS. 18D-18E). Once engaged with the clot at the distal end of the puller, which may be detected by observing the flow and/or pressure through the puller from the suction, the puller may be drawn proximally and/or the inversion support catheter may be moved distally so that the flexible tube rolls over the distal end opening of the inversion support catheter. In FIG. 18F approximately 30% of the clot has been drawn into the inversion support catheter by rolling the flexible tube; in FIG. 18G, more, but not all (e.g., approximately 70%) of the clot has been ingested, though a substantial amount of clot remains outside of the inversion support catheter and flexible tube. The vacuum may be left on, or it may be turned off while pulling the puller proximally to engulf/grab the clot. Heavy arrows indicate movement of the components of the apparatus, such as the intermediate catheter, which may be advanced distally, the inversion support catheter, which may also be advanced distally, and the puller, which may be withdrawn proximally. These motions may be coordinated by the handle (not shown) and/or performed manually by the user. Once the flexible tube has reached the distal end of the inversion support catheter, it may stop or be stopped, to prevent it from rolling over the distal end. In FIG. 18A-18J the second end of the flexible tube includes a cuff that may prevent the flexible tube from rolling over the distal end when pulling proximally on the puller, as shown in FIG. 18H. In FIG. 18I, the intermediate catheter is shown advancing distally beyond the cuff and distal end of the intermediate support catheter, which inverts the cuff over and against the clot without breaking or disrupting the clot. A vacuum (suction) through the intermediate catheter is also shown being applied (by the small arrows). As shown in FIG. 18J, the flexible tube, puller and inversion support catheter are then drawn proximally into the intermediate catheter along with the un-engulfed portion of the clot, either by driving the intermediate catheter distally over them, and/or by pulling the inversion support catheter (which may be pulled with the puller) proximally.

In FIG. 22A, the cuff includes a plurality of slits that may engage with the intermediate catheter (IC) when it is driven distally past the cuff to drive the cuff to invert over the distal end of an inversion support catheter, as shown in FIG. 18I, controllable preventing inversion when pulling the puller, but allowing inversion without disrupting the clot when advancing the intermediate catheter, as illustrated in FIG. 22B, showing inversion of the cuff after driving the intermediate catheter distally.

FIGS. 23A-23B illustrate example of the proximal end of a mechanical thrombectomy apparatus, showing the components of the apparatus (e.g., guidewire, inner/inversion support catheter, puller, and intermediate catheter). FIG. 23B shows another example, of a proximal end of the mechanical thrombectomy apparatus showing manual controls, including vacuum attachment ports, for the different regions.

FIGS. 24A-24B illustrate another example of a set of proximal end controls for a mechanical thrombectomy apparatus. In FIG. 24A the apparatus control region is shown in a first puller position (prior to pulling the clot in). In FIG. 24B the apparatus control region is shown after pulling the clot (showing the puller hub extended proximally).

In FIG. 26A, similar to that shown in FIGS. 18A-18J, the apparatus include a flexible (e.g., knitted) tube that is attached at the first end to a puller catheter and is configured to expand within the inversion support catheter to an outer diameter that is greater than 40% (shown here, it's greater than 90%) of the inner diameter of the inversion support catheter, driving the region of the flexible tube within the inversion support catheter against the walls, even when unloaded by clot. The other region (un-inverted) of the flexible tube along the outer diameter of inversion support catheter is shown as snug with the inversion support catheter in the un-constrained configuration. This results in the Y-shaped distal profile, for the inverting flexible tube, which may help grab even larger diameter clots.

FIG. 26B illustrates another example of a mechanical thrombectomy apparatus in which the expanded outer profile of the flexible tube is expanded beyond the outer diameter of the inversion support catheter near the first end where it attaches to the puller, but the second end, that is freely sliding over the inversion support catheter, has a much smaller (nearly snug) expanded diameter. This region may also or alternatively include a cuff as described herein.

FIGS. 32A-32C illustrate cuffs having a tapered proximal end region. FIGS. 32D and 32E illustrate cuffs having angled proximal-facing sides. FIG. 32F is an example of a cuff having a proximal stent-like region.

DETAILED DESCRIPTION

In general, described herein are inverting tractor mechanical thrombectomy apparatus having a tractor tube, configured as an inverting flexible tractor tube that may be pulled proximally to invert over and into the distal end of an elongate inversion support catheter. An end of the tractor tube may be coupled to a puller (e.g., pull wire, pull catheter, etc.) to provide the proximal pulling force. In particular, described herein are apparatuses and methods of using them that improve or enhance tracking of the apparatus from a patient insertion side (e.g., a femoral region or elsewhere) though a tortious vessel, to a deployment site where the apparatus may be deployed to mechanically remove a clot by rolling the tractor tube into the elongate inversion support catheter and grabbing the clot.

Figure 13C:
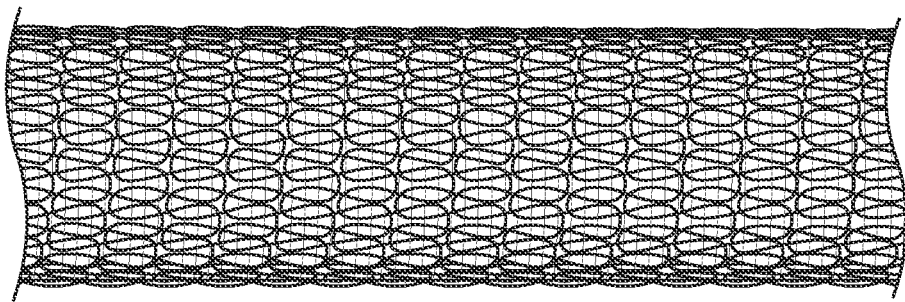
FIG. 13C illustrates an inverting tractor mechanical thrombectomy apparatus configured to hold the kitted tractor tube in a compressed state (in which the transversely arranged, or approximately transversely arranged loops forming the knit overlap over more than 20% or their longitudinal length).
Figure 13B:
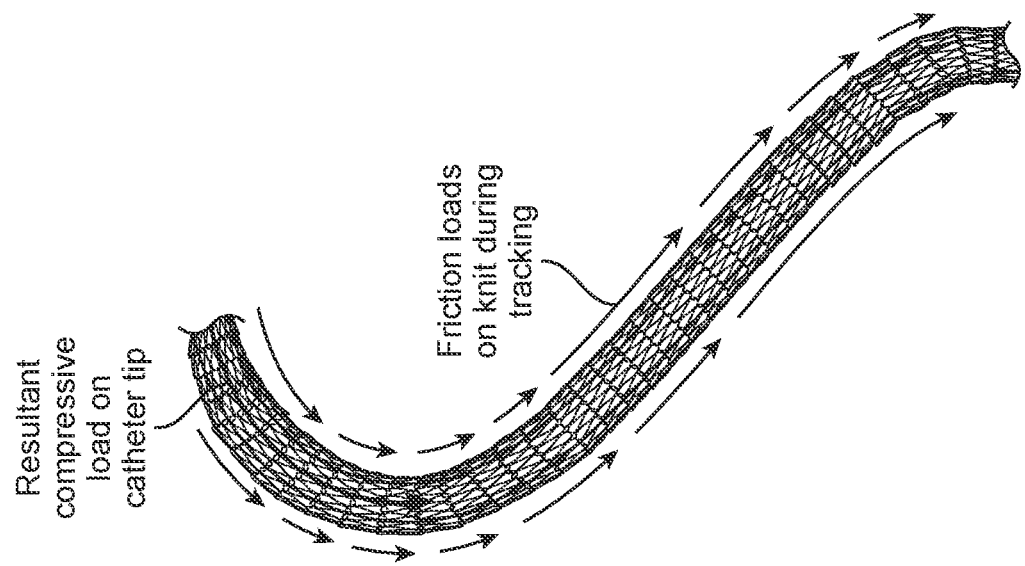
FIG. 13B shows the knitted tractor of FIG. 13A applying compressive force to the elongate inversion support catheter when the apparatus is advanced distally.

In general, the apparatus may be adapted to improve tracking by preventing stiffening or loss of flexibility of the elongate inversion support catheter that may otherwise occur when the tractor tube, which may extend along a substantial distance proximally from the distal open end of the elongate inversion support catheter, applies a compressive force on the elongate inversion support catheter. This may occur, for example, when the apparatus is deployed through the vessel and/or through an intermediate catheter. Although the outer surface of the elongate inversion support catheter, and/or the outer surface of the tractor tube may be lubricated to reduce friction, the distal movement of the apparatus may still result in a drag force on and portion of the tractor tube that is on the outside surface of the elongate inversion support catheter. The resulting drag force is transferred to the distal end of the elongate inversion support catheter, resulting in a compressive force on the elongate inversion support catheter. An example of this is illustrated in FIG. 13B, described in greater detail below.

This issue may be exacerbated when the apparatus includes an elongate inversion support catheter that is configured to have both a high column strength (resisting compression) and an increased flexibility, e.g., by including one or more cut-outs, slots, etc. arranged down the length of the elongate inversion support catheter. For example, metal tubes (e.g., Nitinol tubes, etc.) having transversely arranged slots cut into them along the length of the elongate inversion support catheter may have a high column strength, while remaining sufficiently flexible (at least in an unloaded/untensioned configuration).

In general, an inverting tractor mechanical thrombectomy apparatus for removing a clot from a vessel may be a system, assembly or device including an elongate inversion support catheter (such as those mentioned above), having a distal end and a distal annulus (distal end opening), and a flexible tractor assembly including a flexible tractor tube coupled to an elongate puller within the elongate inversion support catheter. The flexible tractor tube is configured to roll and invert over the distal end opening of the elongate inversion support catheter. Knitted tractor tubes are of particular interested and described herein, although it should be understood that other tractor tubes, e.g., woven, braided, etc., may be used.

Tracking of any of the inverting tractor mechanical thrombectomy apparatus described herein may include an intermediate catheter (I.C.) as a delivery catheter along with a guidewire. For example, FIG. 1A illustrates an example of a typical intermediate catheter 101 that may be used. Note that in some variations, as will be illustrated below, an intermediate catheter is not needed or used and the inverting tractor mechanical thrombectomy apparatus may be delivered to the deployment site near the clot to be removed without the need for an intermediate catheter.

FIG. 1B illustrates one example of an elongate inversion support catheter. In this example, the elongate inversion support catheter 103 is formed of a normally high column-strength material (such as a metal, e.g. Nitinol) having a number of openings (e.g., cut-out regions) or slots along the length to provide enhanced flexibility. The distal end of the elongate inversion support catheter is open 105. Either the entire length or a portion of the length may be cut/slotted as described. The elongate inversion support catheter includes a catheter body having a distal end region that includes a distal end opening 105. The distal end region may have an increasing softness (measured by durometer, e.g., shore durometer) except that the very distal-most end region (distal end 105, including the distal end opening) may be substantially less soft than the region immediately proximate to it. Thus, although the distal tip region of the catheter (e.g., the distal most x linear dimensions, where x is 10 cm, 7 cm, 05 cm, 4 cm, 3 cm, 2 cm, 1 cm, 9 mm, 8 mm, 7 mm, 6 mm, 5 mm, 4 mm, 3 mm) has an increasing softness/decreasing harness extending from the proximal to distal ends, the very distal end region 107 (e.g., measured as distal most z linear dimensions, where z is 1 cm, 9 mm, 8 mm, 7 mm, 6 mm, 5 mm, 4 mm, 3 mm, 2 mm, 1 mm, 0.8 mm, 0.5 mm, 0.3 mm, 0.2 mm, etc., and z is always at least three times less than x) has a hardness that is greater than the hardness of the region immediately proximal to it, and may be as hard or harder than the proximal-most region of the distal tip region.

In FIG. 1B, the elongate inversion support catheter is an elongate hollow catheter having a column strength that is sufficient to prevent buckling when the catheter is pulled over the distal annulus (distal end opening). Thus, the elongate inversion support may be configured so that it does not collapse (e.g., buckle) when 500 g or less of of compressive force is applied (e.g., able to withstand at least about 500 g, at least about 700 g, at least about 600 g, at least about 500 g, at least about 400 g, at least about 300 g, etc. of compressive force) for neurovascular applications. For peripheral vascular applications the elongate inversion support may be selected or configured to withstand at least 1500 g of compressive force (e.g., at least about 2000 g, 1900 g, 1800 g, 1700 g, 1600 g, 1500 g, 1400 g, etc. of compressive force). In general, any of the apparatuses described herein may include an elongate inversion support catheter that is not a full-length catheter, but may include a portion of a catheter, typically at the distal end, connected to a rod, wire, hypotube, or the like. In FIG. 1B the catheter 103 of the elongate inversion support catheter may be any appropriate type of catheter or portion of a catheter, including microcatheters appropriate for neurovascular use.

In some variations the distal end 105 of the elongate inversion support catheter is adapted so that the tractor may slide or roll and invert over the distal end of the catheter without being caught (binding, jamming) or without substantial friction. For example, in some variations the distal tip (end) may be curved or radiused, particularly on the outer surface (e.g., the transition from outer diameter to inner diameter).

FIG. 1C1 shows an example of a flexible tractor tube 111 coupled to an elongate puller 113, forming a pullable tractor assembly 140. In this example, the tractor tube 111 is shown integrated with the puller 113 and extending back over the puller. The puller in this example is a catheter (e.g. a micro catheter, also referred to herein as a PMC or pull micro catheter). In this example, the opposite end of the flexible tractor tube 111 is open and free (e.g., not connected to the puller or catheter, e.g. elongate inversion support catheter). As will be described in greater detail below, this open, free, end may be adapted to be expanded and held open, e.g., by shape setting back on itself and/or by including an annular bias, to enhance deployment and positioning of the catheter between the flexible tractor tube and the puller. In FIGS. 1C1 and 1C2, the tractor tube is formed of material (e.g., wove, knitted, braided, etc.) that is flexible and elongate. The tractor 111 is shown extended from the puller in a first configuration. It may be particularly beneficial if the relaxed outer diameter of the flexible tractor in this first configuration has a greater outer diameter than the outer diameter of the catheter of the elongate inversion support into which the tractor will be positioned prior to inverting. The flexible and tubular tractor 111 may be sufficiently soft and flexible (e.g., having a low collapse strength) so as to easily roll and fold over the distal aperture of the elongate inversion support. The tractor 111 may be configured, e.g., by shape-setting (heat setting, etc.), to expand in the relaxed first configuration to a radial diameter that is between 1.1 and 10 times (e.g., between 1.1× and 5×, between 1.1× and 4×, etc.) the diameter of the inner diameter of the catheter of the elongate inversion support when unconstrained. In FIG. 1C2, the tractor tube 111 is shown coupled to a guidewire (non-hollow structure) 115. The tractor may be formed of a mesh, braided, woven, knitted, or sheet of material and is generally adapted to grasp the object to be removed (e.g., blood clot).

Figure 2A:
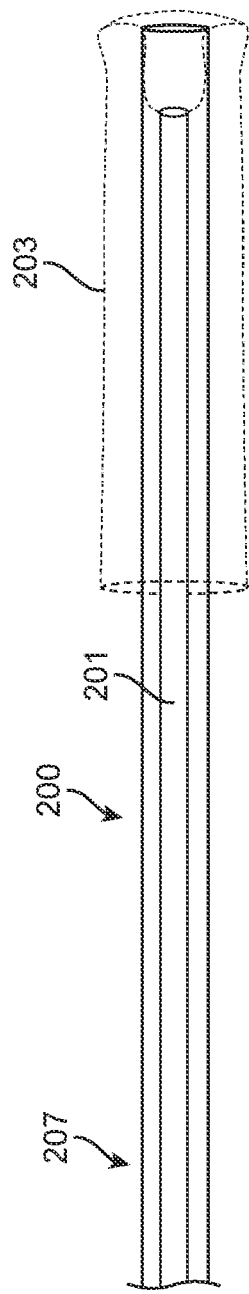
FIGS. 2A-2C illustrate the operation of an inverting tractor mechanical thrombectomy apparatus as described above.
Figure 2B:
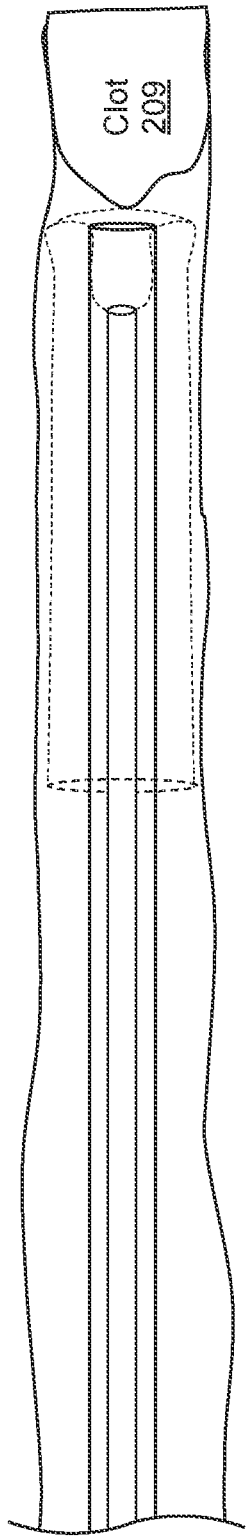
Figure 2C:
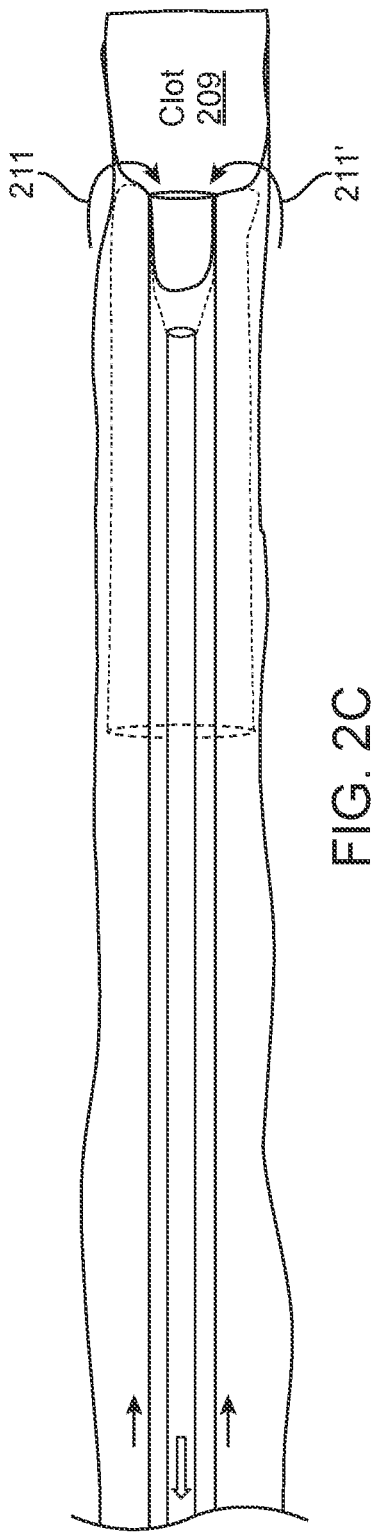

FIG. 2A illustrates an example of an inverting tractor mechanical thrombectomy apparatus 200 deployed. In FIG. 2B the inverting tractor mechanical thrombectomy apparatus is shown deployed near a clot 209. In the deployed configuration the puller 201 (shown here as a puller micro catheter) is held within the elongate inversion support catheter so that the flexile tractor tube 203 extends from the end of the puller and expands toward the inner radius of the elongate inversion support catheter 207; at the distal end opening of the elongate inversion support catheter the tractor tube inverts over itself and extends proximally in an inverted configuration over the distal end of the elongate inversion support catheter. As shown in FIG. 2C, by pulling the puller proximally, the tractor tube rolls and everts over the distal end opening of the elongate inversion support catheter, drawing the adjacent clot into the elongate inversion support catheter, as shown.

FIG. 2A the elongate inversion support catheter is positioned between the tractor tube and the puller so that the tractor tube can be pulled proximally by pulling on the puller and rolling the tractor tube into the elongate inversion support catheter so that it inverts. The portion of the tractor tube that is inverted over the distal end of the elongate inversion support catheter has an outer diameter that is greater than the outer diameter of the elongate inversion support catheter. The tractor is biased so that it has a relaxed expanded configuration with a diameter that is greater than the outer diameter (OD) of the elongate inversion support catheter; in addition, the tractor tube may also be configured (e.g., by heat setting, etc.) so that when the tractor tube is everted and rolled over the distal end opening into the elongate inversion support catheter, the outer diameter of the tractor tube within the elongate inversion support catheter has an outer diameter that is greater than the inner diameter of the elongate inversion support catheter (e.g., greater than 0.1×, 0.5× 0.6×, 0.7×, 0.75×, 0.8×, 0.9×, 1×, etc. the inner diameter, ID, of the elongate inversion support catheter. This combination of an un-inverted diameter of the tractor tube of greater than the diameter of the OD of the elongate inversion support catheter and an inverted diameter of the tractor tube of greater than 0.7× the ID of the elongate inversion support catheter is surprisingly helpful for preventing jamming of the apparatus, both when deploying the apparatus and when rolling the tractor over the distal end opening of the elongate inversion support catheter to grab a clot. The tractor may be expandable and may be coupled to the puller as shown. In some variations the flexible tractor and the puller may comprise the same material but the tractor may be more flexible and/or expandable, or may be connected to elongate puller (e.g., a push/pull wire or catheter).

In FIG. 2C the clot may be drawn into the elongate inversion support catheter by pulling the tractor proximally into the distal end of the elongate inversion support catheter, as indicated by the arrows 211, 211' showing pulling of the inner portion of the flexible tractor, resulting in rolling the tractor over the end opening of the catheter and into the catheter distal end and inverting the expandable distal end region so that it is pulled into the catheter, shown by arrows. The end of the tractor outside of the catheter may be "loose" relative to the outer wall of the catheter.

In general the mechanical thrombectomy apparatuses described herein may be highly flexible, both before actuating and during operation. For example, the flexible tractor may not increase the stiffness/flexibility of the catheter of the elongate inversion support, and particularly the distal end region of the catheter too much, to avoid impacting maneuverability, particularly within tortious vessels of the neurovasculature. Described herein are flexible tractor tube portions that increase the stiffness of the last "y" cm (e.g., the distal most 20 cm, 18 cm, 15 cm, 12 cm, 10 cm, 9 cm, 8 cm, 7 cm, 6 cm, 5 cm, 4 cm, 3 cm, 2 cm, 1 cm, etc.) of the catheter less than a predetermined percentage (e.g., less than 10%, 12%, 15%, 18%, 20%, 25%, 30%, etc.). For example, described herein are flexible tractor tube portions that pass through the catheter and double back over the distal end of the catheter but increase the stiffness of a distal 5 cm of the catheter by less than 15% of the stiffness of the distal 5 cm of the catheter without the flexible tube extending therethrough and doubling back over the distal end of the catheter.

The tractors may be woven, braided and/or knitted materials. For woven and braided materials, which may include a plurality of fibers that are woven or braided to form the inverting tube, these structures may be tuned to prevent jamming and/or to reduce the force necessary to pull the tractor and invert over the catheter tip. For example, the mechanical atherectomy apparatus may include a braid-type tractor that can roll freely around the tip of catheter even in a tortuous anatomy and when grabbing clot by tuning one or more of the braid structure; minimizing the braid angle; including a hydrophilic coating on the distal aspect of the catheter outer diameter (OD) or the inner diameter (ID) of the braid (e.g., tractor); including a radiused wall on the catheter; and/or increasing the stiffness of the distal tip region relative to adjacent proximal regions. Alternatively, it may be advantages to have a hydrophilic coating on 1, 3, 5, 10, or 15 cm of the distal ID or the entire catheter ID. This may even enhance aspiration of the clot without a tractor element.

As mentioned, the tractor (e.g., braided, woven, knitted, etc.) may be configured to collapse down into the inner diameter (ID) of the catheter as little as possible. For example the tractor may collapse to an ID that is greater than, equal to, or within 90%, 85%, 75%, 70%, 65%, 60%, or 50% of the catheter inner diameter (ID)/Catheter Tip OD, since, when the tractor is being pulled around catheter tip it may create axial tension on the tractor (e.g., braid, knit, etc.) that can inadvertently cause the tractor to jam on the catheter tip. When tractor is pulled around catheter tip, the tractor is being pulled in the axial orientation creating axial tension on tractor structure as the tractor is being pulled through the catheter ID. By having the tractor elements jam at an ID greater than or equal to 90%, 85%, 75%, 70%, 65%, 60%, or 50% of the catheter ID (or in some variations, OD), when being axially tensioned, the tractor is less likely to grab/synch down onto the catheter tip, helping the braid roll around the catheter tip with less axial force applied by the user. If less axial force is required by the user to pull the tractor structure around the tip then the catheter tip is less likely to buckle or deflect when retracting the tractor. It may be advantageous to minimize the chance the catheter tip will buckle. The tractor can be tuned to "jam" at a specific ID by controlling any of the following variables and in any combination: selecting a specific number of braid ends, selecting the size/diameter of the braid ends; selecting the braid material (e.g., multifilament or monofilament); heat setting the bias on the braid (e.g., braid diameter); and selecting a braid pattern, e.g., 1×2, 1×1 or any other pattern.

The braid angle may be minimized to prevent locking up of the rolling of the tractor over the catheter end opening. Typically, the lower the braid angle (e.g., 45 degrees or less, 40 degrees or less, 35 degrees or less, 30 degrees or less, 25 degrees or less, 20 degrees or less, etc.) the less likely it is to have the braid cross over points catch on the catheter tip.

In any of the variations described herein, the catheter and/or a surface of the tractor may be coated to enhance rolling over the distal end region of the catheter. It may be helpful to have a hydrophilic coating on the distal aspect of the catheter OD or the ID of the tractor so the tractor can more easily side over the catheters distal end and around the tip of the catheter when pulled through the inside of the catheter.

The radius wall of the catheter tip may be chosen/set to within a range that allows sliding. For example, it may be helpful for the tip of the catheter to have the largest radius possible but at least 0.025" radius wall on the catheter, ideally approximately 0.05" radius wall.

The stiffness of the distal of the elongate inversion support catheter may be sufficiently stiff to prevent collapse as the tractor is pulled; it may also be lubricious (e.g., by a coating or material property). The distal most section of the elongate inversion support catheter tip (e.g., the last 5 mm) may be fabricated of a material which is stiff enough and lubricious enough so the distal tip of the catheter does not collapse or buckle inward ward when the braid structure is rolling around the catheter tip. Thus, the distal tip may have a stiffness that is greater than the more proximal region at the distal end of the catheter.

It may be helpful or desirable to have pores in the tractor. A lack of gaps or small pore size may limit the ability of the braid to grab clot. Alternatively or additionally, it may be desirable to form a braid structure with texture. One example is to braid two or more different diameter braid ends into the same structure: the difference in braid end diameters will help form a texture to the braid structures outer surface, aiding the grabbing of the clot when rolling the braid-dozer around the catheter tip.

As an alternative (or in addition) the tractor may be configured to lock so it does not compress in diameter during axial load by adding a coating, laminate or adhesive to the braid at a desired diameter. Adding a thin coating, laminate or adhesive can inhibit the braid elements from sliding with respect to each other, thereby locking the braid to a specific diameter. The coating can be applied while leaving the majority of the pores and pore area substantially open. Examples of thin coatings include urethanes and silicones with and without hydrophilic coatings and hydrophilic coatings with no tie layer.

Figure 2D:
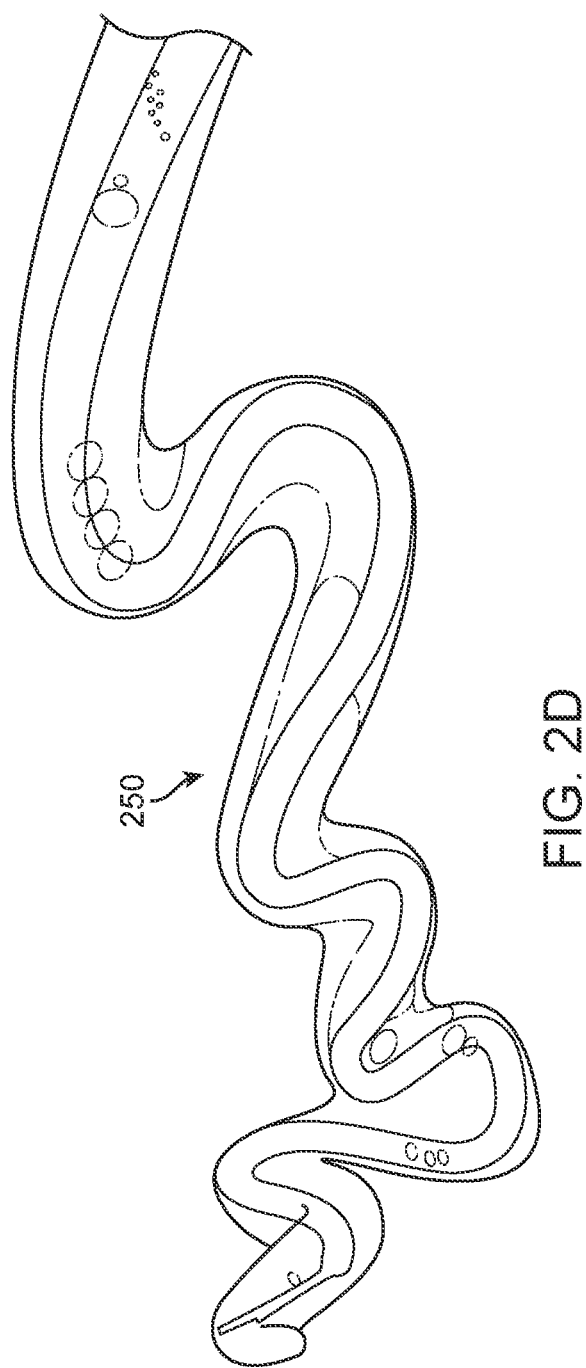
FIG. 2D illustrates an example of a tortious path that the inverting tractor mechanical thrombectomy apparatus may have to navigate in order to reach the clot.

As mentioned above, any of the apparatuses described herein may be configured to provide enhance delivery of the apparatus though the tortious anatomy of the vessels in order to deploy the apparatuses near the clot. For example, FIG. 2D illustrates an example of a tortious path 250 that may be navigated by the apparatuses (including in particular the apparatuses that are pre-loaded into an intermediate/delivery catheter).

Preloaded Apparatuses

Figure 3A:
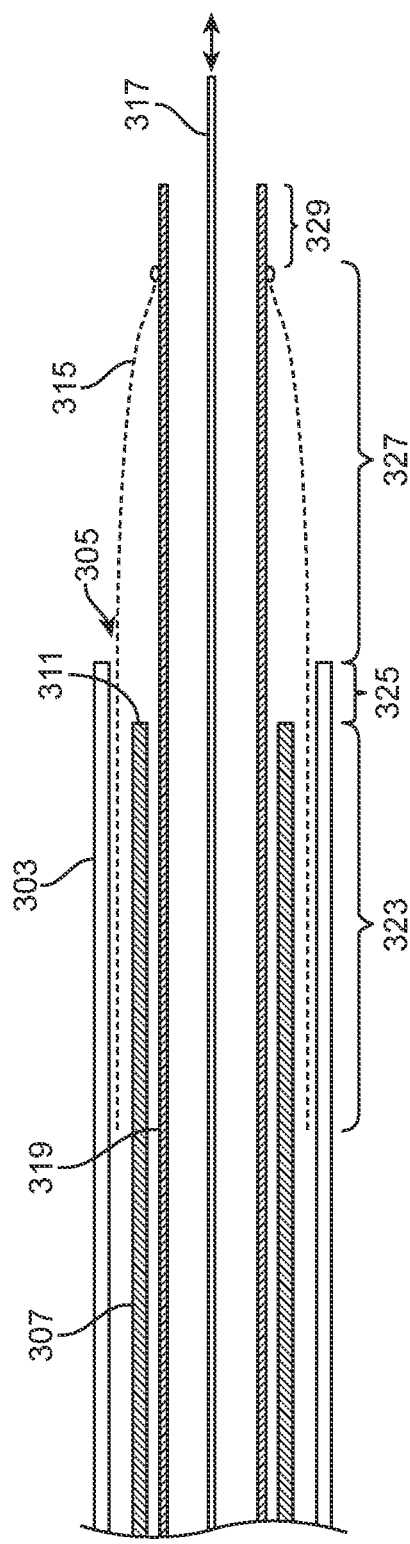
FIG. 3A is an example of a preloaded assembly of an inverting tractor mechanical thrombectomy apparatus within an intermediate catheter that may be used as described in order to deliver an inverting tractor mechanical thrombectomy apparatus though a tortious vessel to a deployment location. In this example, the elongate inversion support catheter is held within the intermediate catheter (and may be locked in position) until deployed, while the pusher (e.g., PMC) and tractor are partially extending distally. A guidewire may also be used.

One solution to the problem with tracking of the inverting mechanical thrombectomy apparatuses such as those described herein, and particularly those having a high flexibility, high column strength elongate inversion support catheter (which may stiffen when placed under even relatively small compressive forces from their distal end by the tractor tube) is to preload the inverting mechanical thrombectomy apparatuses within an intermediate catheter so that a portion of the inverting mechanical thrombectomy apparatus is protected within the body of the intermediate catheter, while the rest of the intermediate catheter portion is advanced over and/or along (with) a guidewire. For example, FIG. 3A illustrate one example of a pre-loaded inverting tractor mechanical thrombectomy apparatus for removing a clot from a vessel configured to be delivered through a tortious anatomy. In this example, the apparatus may include an intermediate catheter 303 having a distal end 305. The intermediate catheter (I.C.) may be considered part of the inverting mechanical thrombectomy apparatus, although in other variations it may be considered a separate component that is used with the inverting mechanical thrombectomy apparatus. The apparatus also includes an elongate inversion support catheter 307 (also referred to as push catheter "880 Device" in FIG. 3) within the lumen of the intermediate catheter. The elongate inversion support catheter 307 has a distal end 311 and a distal end opening. The apparatus also includes a puller 319 extending distally within the elongate inversion support catheter and a flexible tractor tube 315 extending proximally from a distal end region of the puller. The puller extends from the distal end of the intermediate catheter and the distal end opening of the elongate inversion support catheter.

In the pre-assembled configuration shown in FIG. 3A, the elongate inversion support catheter is held within the lumen of the intermediate catheter so that the distal end opening of the elongate inversion support catheter is proximal to the distal end opening of the intermediate catheter by a first distance 325. This distance may be between about 1 mm and about 10 cm (e.g., between about 2 mm and about 10 mm, between about 2 mm and about 20 mm, between about 2 mm and about 30 mm, etc.). The elongate inversion support catheter may be fixed in position relative to the intermediate catheter, so that as the two catheters move together, until released. For example, the proximal ends of the intermediate catheter and the elongate inversion support catheter may be removably coupled.

The tractor tube in the pre-assembled apparatus of FIG. 3 extends between the elongate inversion support catheter and the intermediate catheter for some second distance along the length 323 of the elongate inversion support catheter. Securing the end of the tractor tube between the I.C. and the distal end of the elongate inversion support catheter may help both hold it in place, so that it may be held in compression, as will be described in greater detail below, which may also help prevent it from applying compressive force to the distal end of the elongate inversion support catheter. For example, the second length 323 may be between about 1 mm and about 50 cm (e.g., between about 5 cm and about 10 cm, between about 1 cm and about 20 cm, between about 1 cm and about 10 cm, between about 2 cm and about 20 cm, between about 2 cm and about 10 cm, etc.).

The portion of the tractor tube 315 and puller 319 (e.g., pull micro catheter, or pmc) in this pre-loaded example may extend distally and ride over the guidewire 317. The tractor tube and puller may also be longitudinally fixed relative to the intermediate catheter 303 (e.g., by releasably locking, e.g., at the distal end region) or they may be somewhat longitudinally slideable (and, in some variations, prevented from exceeding a range of, e.g., between about 1 mm and 20 cm from the distal end opening 305 of the intermediate catheter 303.

In practice, the portion 327 of the tractor tube 315 that extends outside of the intermediate catheter 303 may be between about 1 mm and about 20 cm (e.g., between about 1 cm and about 7 cm, between about 1 cm and about 10 cm, between about 1 cm and about 15 cm, between about 2 cm and about 10 cm, between about 2 cm and about 7 cm, etc.). As mentioned, this distance may be fixed (e.g., by fixing the puller with respect to the push catheter and/or I.C.), or variable. In any of these variations, the puller may extend some distance 329 beyond the distal attachment site for the flexible tractor tube, or the tractor tube may be attached at the distal end of the puller. The distance from the attachment site of the tractor tube and the distal end of the puller may be between about 0 mm and about 10 cm, for example (e.g., between about 1 mm and about 10 cm, between about 1 mm and about 5 cm, etc.).

In variations in which the pre-loaded apparatus is configured with the puller (and therefore the tractor tube) and/or the elongate inversion support catheter fixed relative to the intermediate catheter for delivery of the apparatus to the clot (e.g., adjacent to the clot), once in the deployment location, the elongate inversion support catheter and/or puller may be unlocked so that they may move independently of the intermediate catheter. In some variations, the elongate inversion support catheter may be unlocked first, so that it can be advanced distally into the tractor tube and over the puller; once the distal end of the elongate inversion support catheter is near the attachment site for the tractor tube on the puller, the puller may be also be released (manually or automatically).

Figure 3B:
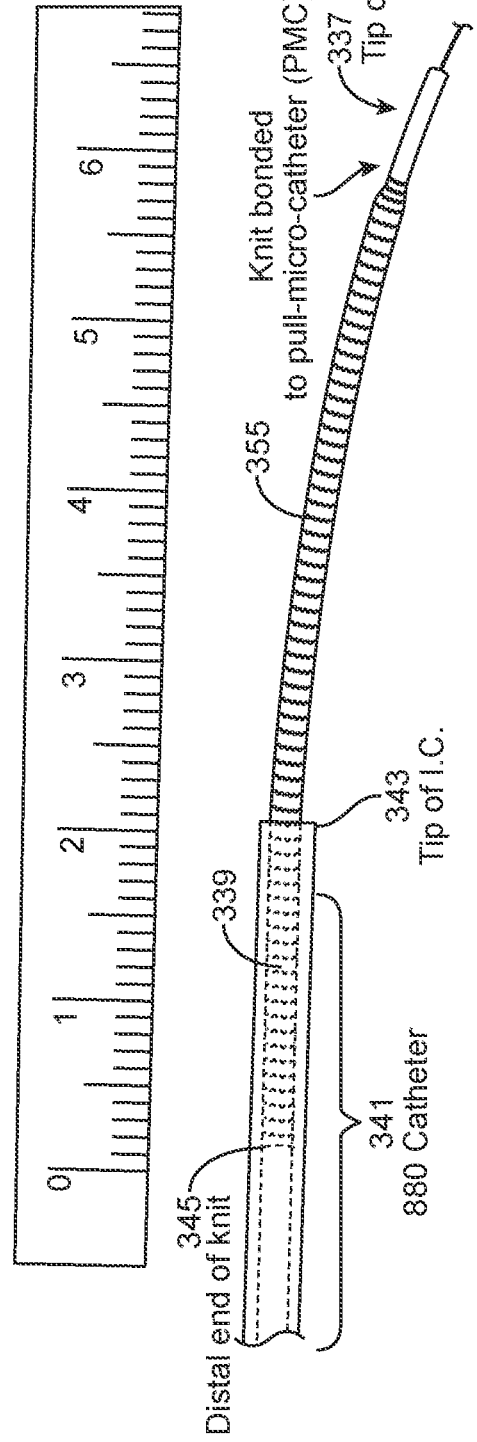
FIG. 3B show a prototype assembly (pre-assembled) similar to that shown in FIG. 3A.

FIG. 3B illustrates another example of a pre-loaded apparatus (pre-loaded inverting tractor mechanical thrombectomy apparatus for removing a clot from a vessel configured to be delivered through a tortious anatomy). In FIG. 3B, the tractor tube is a knit 355 that is bonded to the puller near a distal end region, described in FIG. 3A. The distal end region of the puller (pmc) 337 extends from the intermediate catheter 343. The opposite end 345 of the tractor tube, approximately 1 cm) is held between the intermediate catheter and the elongate inversion support catheter 341, which is entirely within the intermediate catheter. Exemplary dimensions are shown by the ruler above the prototype device.

Figure 4A:
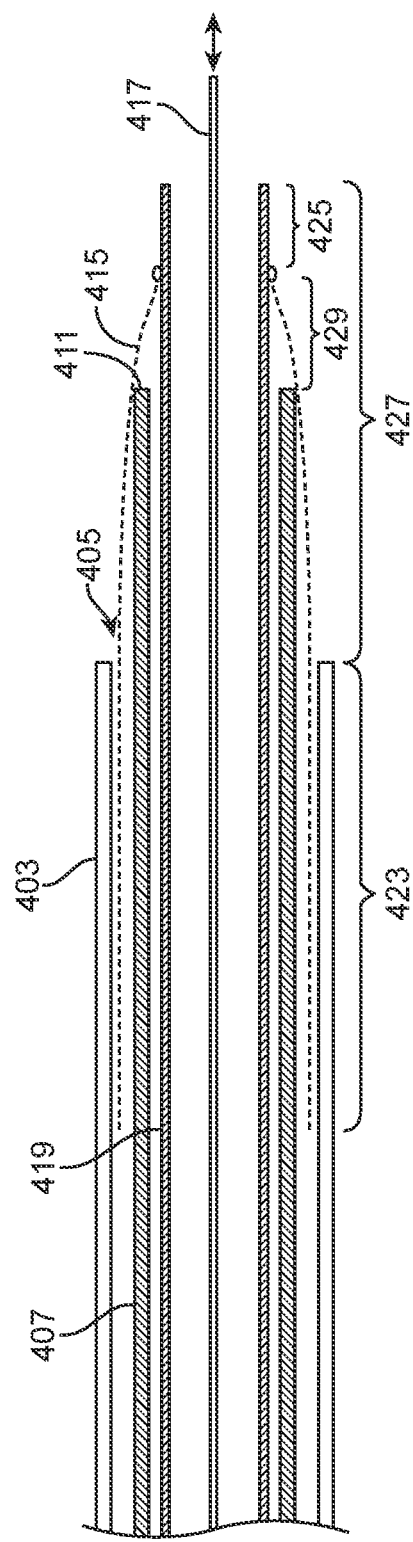
FIG. 4A is another example of a preloaded assembly of an inverting tractor mechanical thrombectomy apparatus within an intermediate catheter that may be used as described in order to deliver an inverting tractor mechanical thrombectomy apparatus though a tortious vessel to a deployment location. In this example, the elongate inversion support catheter is extended from the intermediate catheter, and extends distally along with the puller (PCM).

Another variation of a pre-loaded inverting tractor mechanical thrombectomy apparatus for removing a clot from a vessel configured to be delivered through a tortious anatomy is shown in FIGS. 4A-4D. In FIG. 4A, the apparatus contains the same elements shown in FIG. 3A, but they are arranged and interact in a different manner. For example, the pre-loaded apparatus includes an intermediate catheter 403 with an open distal end 405, an inner elongate inversion support catheter 307, a tractor tube 415 and a puller 419. In FIG. 4A, he tractor tube is connected to a distal end region of the puller (e.g., within a fixed distance 425 of the distal end of the puller, e.g., between about 0 mm and 10 cm (e.g., about 1 mm to about 10 mm, etc.) as in the example in FIG. 3A. The opposite end of the tractor tube is held between the intermediate catheter 403 and the elongate inversion support catheter 407, as in FIG. 3A. For example, between about 1 mm and about 50 cm of tractor tube (e.g., between about 5 cm and about 10 cm, between about 1 cm and about 12 cm, etc.) may be between the intermediate catheter and the elongate inversion support catheter; the tractor tube may be held loosely, or it may be held so that the distal end of the tractor tube on the outside of the elongate inversion support catheter is compressed, it from being pulled distally by friction from the vessel walls, resulting in compressive forces on the distal end of the elongate inversion support catheter.

In FIG. 4A, the elongate inversion support catheter is secured in position relative to the puller so that the distal end opening of the elongate inversion support catheter is near the attachment site for the tractor tube on the puller. For example, the distance between the elongate inversion support catheter distal end opening and the attachment site for the tractor tube 429 may be between about 0 mm and about 10 cm (e.g., between about 0 mm and about 1 mm, between about 0 mm and about 2 mm, between about 1 mm and about 5 mm, between about 1 mm and about 3 mm, etc.). As discussed above for FIG. 3A, the puller, elongate inversion support catheter and intermediate catheter may be releasably locked together so that they move together. The portion of the puller from the attachment site of the tractor tube to the distal end of the puller 425 may, as described for FIG. 3A, above, be between about 0 mm and about 10 cm (e.g., between about 0 mm and about 7 mm, between about 0 mm and about 5 mm, etc.).

In operation, the pre-assembled apparatus shown in FIG. 4A may advance distally (e.g., over a guidewire) towards a clot in a vessel with the slightly more flexible distal end portion consisting of a distal portion of the puller, tractor and elongate inversion support catheter extending distally from the distal opening of the intermediate catheter by a distance 427 that may be, for example, between about 1 cm and 20 cm (e.g., between about 2 cm and about 7 cm, between about 1 cm and 10 cm, between about 2 cm and about 7.5 cm, etc.). This presents a more flexible distal end region that tapers slightly over the guidewire, allowing the apparatus to navigate tortious vessels, including those having branches. Once the distal end of the apparatus is within the deployment region, near (e.g., adjacent to) the clot to be removed, the apparatus may be deployed by removing the coupling between the intermediate catheter, puller and elongate inversion support catheter, and allowing the intermediate catheter to be withdrawn at least slightly, and for the elongate inversion support catheter to be advanced while withdrawing the tractor tube proximally to roll the tractor tube so that it everts over the distal end opening of the elongate inversion support catheter.

Figure 4C:
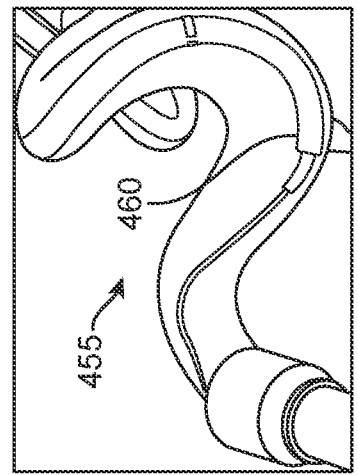
FIG. 4C shows an example of a preloaded assembly such as the one shown in FIGS. 4A and 4B navigating through a model of a tortious vessel.
Figure 4B:
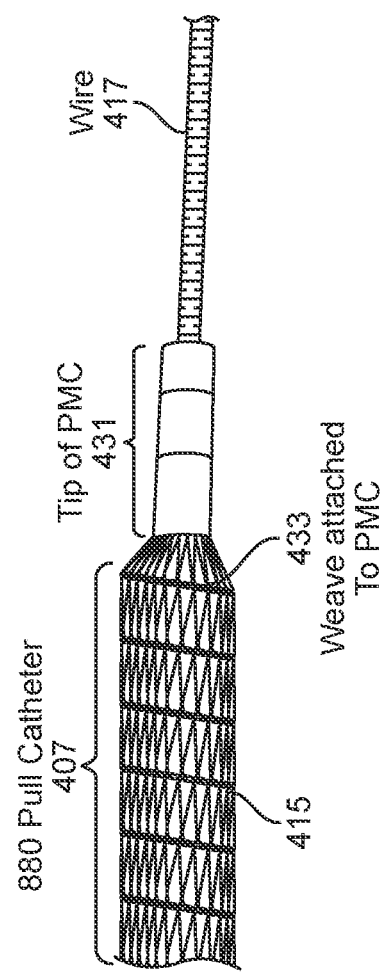
FIG. 4B show a prototype assembly (pre-assembled) similar to that shown in FIG. 4A.

FIG. 4B illustrates an example of distal end of a prototype pre-assembled apparatus similar to that shown in FIG. 4A. In FIG. 4B the apparatus is shown over a guidewire 417 with the elongate inversion support catheter 407 near the attachment site 433 for the tractor tube onto the distal end region of the puller; a distal end region of the puller 431 extends from the tractor tube attachment site to the distal end opening of the puller.

Figure 4D:
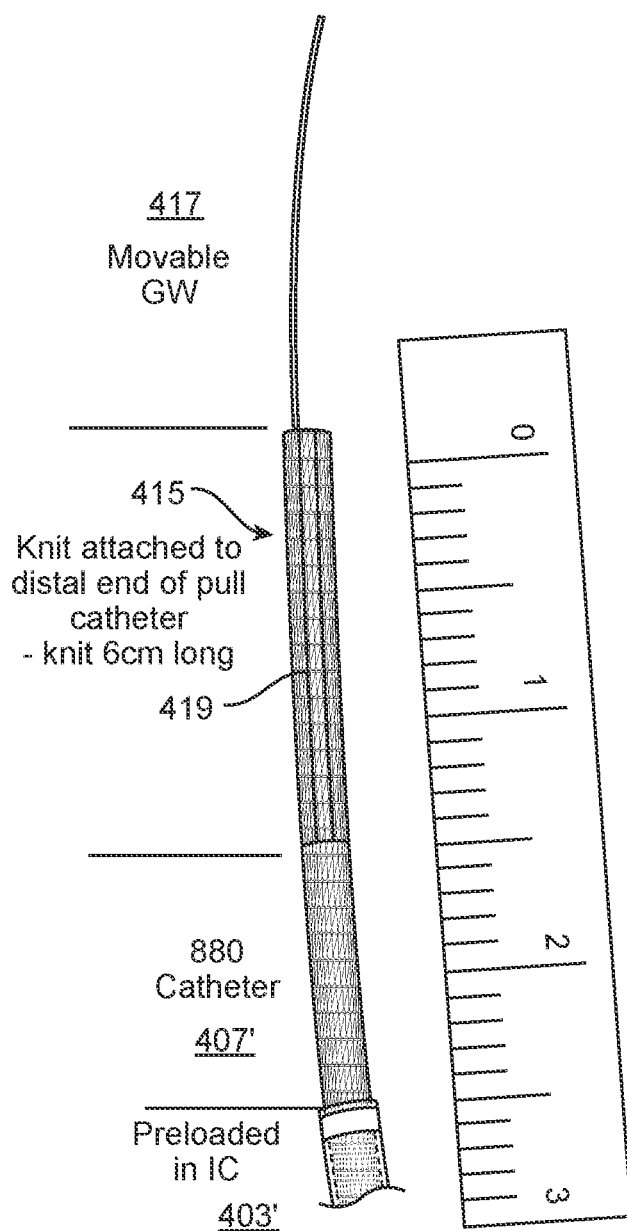
FIG. 4D is another example of a prototype pre-assembled assembly (inverting tractor mechanical thrombectomy apparatus) such as the one shown in FIG. 4A.

FIG. 4C illustrates tracing of an apparatus 460 such as the one shown in FIG. 4B through a tortious model of a blood vessel 455; the flexible distal end leads the device in tracking and navigating through the vessel. FIG. 4D illustrates another example of a distal end region of a pre-loaded inverting tractor mechanical thrombectomy apparatus for removing a clot from a vessel, also showing exemplary dimensions. In FIG. 4D, the apparatus is threaded over a movable guidewire 417, and shows a knitted tractor tube 415' that is attached to the distal end region of a puller 419; an elongate inversion support catheter 407' is between the tractor and the puller, as mentioned above. This is pre-loaded into an intermediate catheter 403'.

Figure 5A:
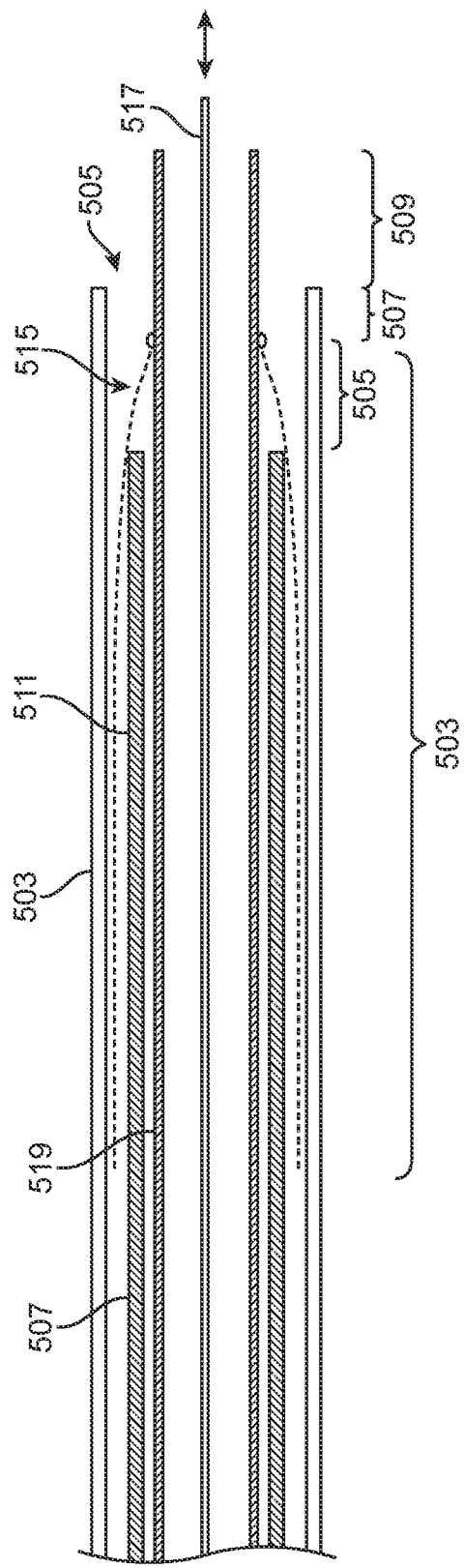
FIG. 5A is another example of a preloaded assembly of an inverting tractor mechanical thrombectomy apparatus within an intermediate catheter that may be used to deliver an inverting tractor mechanical thrombectomy apparatus though a tortious vessel to a deployment location. In this example, the elongate inversion support catheter, and the tractor tube are held within the intermediate catheter, and the distal end (extending beyond the attachment to the tractor tube) of the puller extends distally.

Another example of a pre-loaded inverting tractor mechanical thrombectomy apparatus for removing a clot from a vessel configured to be delivered through a tortious anatomy. In FIG. 5A, unlike the variations shown in FIGS. 3A and 4A, both the elongate inversion support catheter 507 and the tractor tube 515 are held (e.g., releasably locked) within the intermediate catheter 503. This may prevent the tractor tube from pushing against the vessel wall during tracking, and therefore prevent compressive force on the elongate inversion support catheter that may otherwise result in it stiffening. In this example, a portion 509 of the puller 519 may extend distally out of the intermediate catheter, e.g., between about 0 mm to about 30 cm (e.g., between about 0.5 cm to about 20 cm, between about 1 cm to about 15 cm, between about 1 cm to about 10 cm, between about 1 cm and about 5 cm, etc.). The attachment site of the tractor tube to the puller may be at or near the distal opening of the intermediate catheter, or it may be offset by some predetermined distance 507 (or within a range of distances, e.g., between about 0 mm to about 10 cm, such as between about 1 cm to about 8 cm, between about 0 cm to about 2 cm, etc.). Similarly, the elongate inversion support catheter may be preloaded near the attachment site for the tractor tube to the puller (e.g., with a distance 505 of between about 0 mm to about 20 cm, preferably between about 0 mm and 10 mm). The entire length of the tractor tube 503 may be any appropriate length, e.g., between about 1 cm and about 60 cm (e.g., between about 5 cm and about 30 cm, between about 5 cm and about 10 cm, etc.).

In operation, the apparatus shown in FIG. 5A may be deployed over a guidewire (with the component parts all removably secured together, e.g., at a proximal handle) and advanced distally until it is near the clot. In any of these examples, the guidewire may penetrate the clot or it may stop short of the clot. Thereafter, the intermediate catheter may be withdrawn proximally and/or the elongate inversion support catheter advanced distally so that the tractor tube is everted from over the distal end opening of the elongate inversion support catheter and into the elongate inversion support catheter. Pulling the puller proximally may continue to roll the tractor tube, while advancing the elongate inversion support catheter to pull the clot into the elongate inversion support catheter as the tractor tube everts.

Figure 5B:
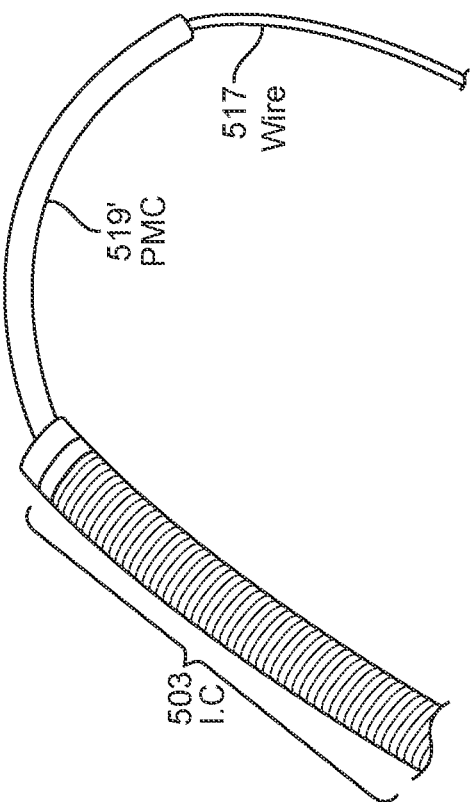
FIG. 5B show a prototype assembly (pre-assembled) similar to that shown in FIG. 5A.

FIG. 5B illustrates another example of the pre-loaded inverting tractor mechanical thrombectomy apparatus shown in FIG. 5A. IN this example, only the distal end of the puller 519' (referred to herein as the pull micro catheter or PMC), while the tractor tube attached more proximally to the PMC remains in the intermediate catheter (I.C.) 503'. In this example, the puller 519' rides over the guidewire 517, and has a length that is about 2 and 5 cm.

Figure 6:
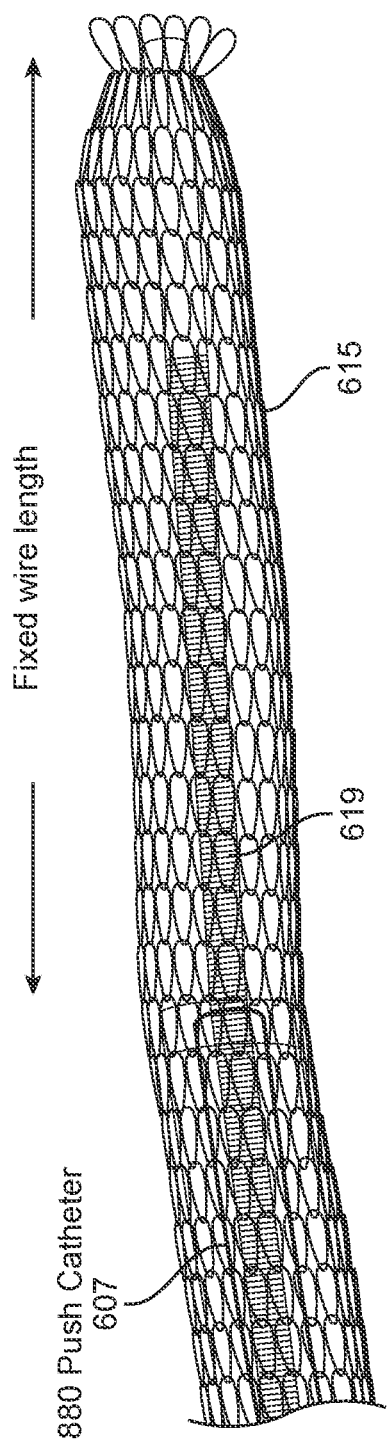
FIG. 6 is an example of a non-over-the-wire variation of an inverting tractor mechanical thrombectomy apparatus in which the puller is a guidewire, similar to the variation shown in FIG. 2C2.

The examples shown in FIGS. 3A-5B shown above include a puller that is configured as a puller micro catheter than may be driven over a guidewire. Any of the variations described herein may instead by configured so that the puller is a guidewire, as shown in the example in FIG. 6. In this example the puller 619 is a guidewire and the tractor tube 615 is attached at one end to the puller. IN this example, the tractor is attached to the distal end of the puller, but it may be attached more proximally, as described above. The elongate inversion support catheter 607 is interposed between the puller and the tractor tube, and may be extended distally so that the tractor tube rolls over the distal end opening of the elongate inversion support catheter when pulling the puller to capture and remove a clot. In the variations shown in FIG. 6, the puller does not necessarily need to be a movable (i.e., longitudinally slideable) pull wire, but may be a fixed wire.

As an alternative to the pre-assembled configurations described in FIGS. 3A-5B described above, any of the apparatuses described herein may also or alternatively be configured to be deployed through an intermediate catheter that is first deployed (e.g., using a guidewire and one or more internal catheters), and left in place; the inverting tractor mechanical thrombectomy apparatus may then be delivered through the intermediate catheter.

Some variations an inverting tractor mechanical thrombectomy apparatus for removing a clot from a vessel configured to be delivered through a tortious anatomy are configured for delivery and deployment to remove a clot without needing an intermediate catheter. For example, in some variations all, or most of, the tractor tube is withdrawn into the elongate inversion support catheter portion of the apparatus. Thus, the outer surface of the apparatus is the outer surface of the elongate inversion support catheter, which may be smooth, and/or lubricated, and therefore less likely than the tractor tube to provoke a compressive force on the distal end region that would otherwise stiffen the elongate inversion support catheter and prevent it from navigating a tortious vessel. For example, FIGS. 7A-7C show a first example of an inverting tractor mechanical thrombectomy apparatus for removing a clot from a vessel configured to be delivered through a tortious anatomy that is configured to deliver the apparatus to the deployment site near the clot with the tractor withdrawn nearly fully into the elongate inversion support catheter.

In FIG. 7A, the inverting tractor mechanical thrombectomy apparatus does not include (or require) the use of an intermediate catheter, though one may be used with it (not shown). The apparatus includes an outer elongate inversion support catheter 707 that includes a stop 704 at or near the distal end. This stop 704 may be a lip, flange, protrusion, or the like, and may provide a larger diameter region that engages with a complimentary stop 816 on the end of the tractor tube 715. The opposite end of the tractor tube is connected to a puller (puller micro catheter 719) similar to the variations described above. When delivered to the clot region of a vessel the puller is withdrawn (preferably loosely, to avoid compressive forces on the elongate inversion support catheter), so that the tractor tube is withdrawn into the elongate inversion support catheter except for small portion at the distal end that is prevented from rolling into the elongate inversion support catheter by the stop on the tractor tube engaging with the stop on the elongate inversion support catheter. The apparatus may be driven over a guidewire 717, as shown, until it is proximate to the clot. FIGS. 7B and 7C illustrate a two-step method for deploying the apparatus that may be used. In This example, the apparatus may be deployed by advancing the puller distally (e.g., "pushing" the puller 775), as shown in FIG. 7B. Thus, the tractor portion will be inverted over itself, ahead of the distal end of the elongate inversion support catheter. Thereafter, as shown in FIG. 7C, the elongate inversion support catheter may be advanced distally into the pocket 777 formed by the inverted tractor tube. The apparatus is then ready for the puller to be pulled proximally to roll the tractor tube back into the elongate inversion support catheter so that it may capture a clot, and may therefore be positioned against or adjacent to the clot.

Figure 8A:
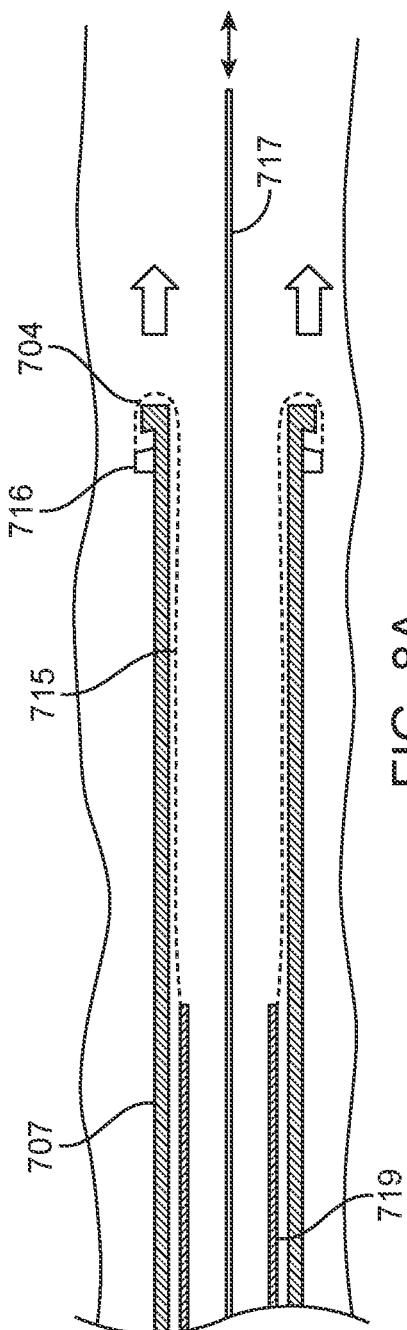
FIGS. 8A-8C illustrate another method of deploying an inverting tractor mechanical thrombectomy apparatus (where the apparatus is configured for delivery of the tractor tube within the elongate inversion support catheter) so that the tractor tube portion is inverted over the elongate inversion support catheter distal end when at the deployment region near the clot. In both FIGS. 7A-7C and 8A-8C, withdrawing the tractor tube into the elongate inversion support catheter may prevent it from applying a compressive force on the elongate inversion support catheter as it is deployed through the vessel, either with an intermediate catheter or without an intermediate catheter.
Figure 8B:
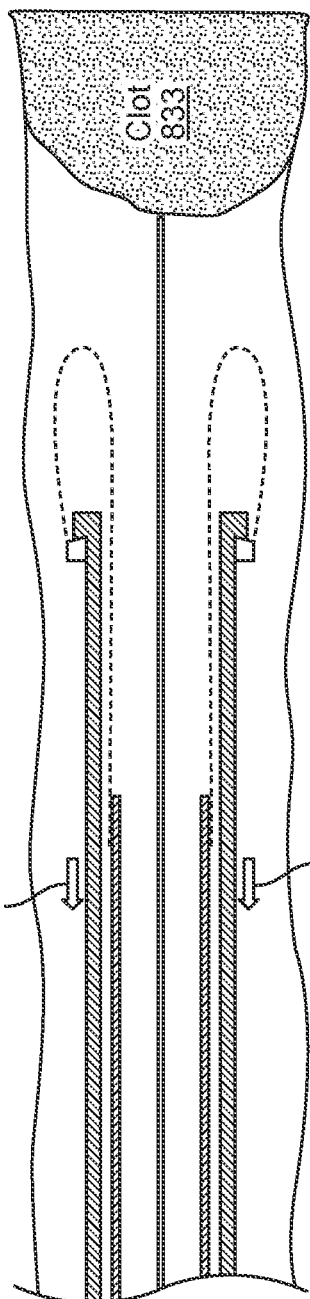
Figure 8C:
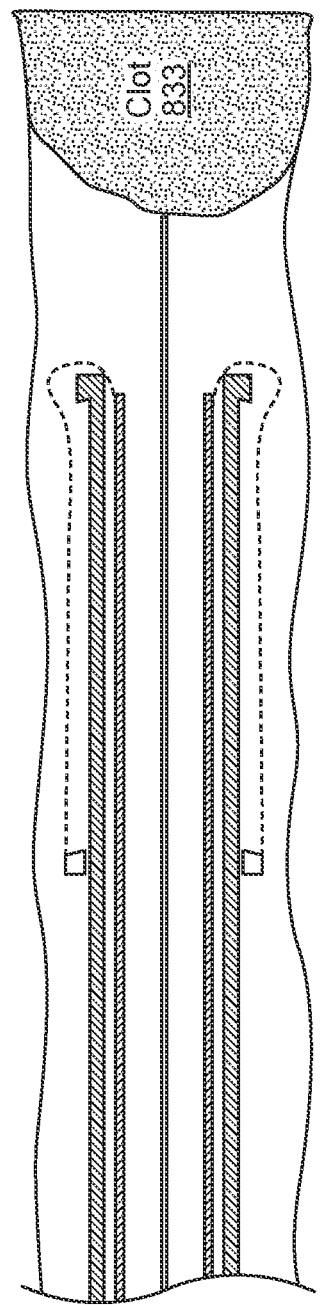

FIGS. 8A-8C show an alternative method of deploying the apparatus shown in FIG. 7A. FIG. 8A is similar to FIG. 7A, showing delivery of the apparatus to the clot over a guidewire 717. The apparatus includes the tractor tube 715 and elongate inversion support catheter 707, which include a stop on one or both of the elongate inversion support catheter and/or tractor tube to engage the distal end of the elongate inversion support catheter with the end of the tractor tube. The apparatus may be delivered with the tractor tube retracted so that it does not tension the elongate inversion support catheter. As shown in FIGS. 8B and 8C, once near the clot, the tractor tube may be repositioned outside of the elongate inversion support catheter so that it can be rolled and used to capture a clot. In FIG. 8B, the elongate inversion support catheter is pulled proximately 851; since the distal end of the elongate inversion support catheter is engaged with the tractor tube to prevent it from sliding off of the end of the elongate inversion support catheter, when the elongate inversion support catheter is pulled proximately while holding the puller in place (or advancing it distally), the tractor tube will extend out of the elongate inversion support catheter and invert, as shown. Thereafter, as shown in FIG. 8C, the elongate inversion support catheter may be advanced distally between the fold formed by the inverted tractor tube, and the entire apparatus advanced distally back to the clot 833, a shown. Once proximate the clot, the puller may be pulled proximally to capture the clot and remove it.

FIGS. 9A-9K illustrate one method of removing a clot using a preloaded assembly of an inverting tractor mechanical thrombectomy apparatus within an intermediate catheter, such as the variation shown in FIG. 3A. In general, a method of using any of the preloaded assemblies of inverting tractor mechanical thrombectomy apparatuses described herein (e.g., in FIGS. 3A-5B), may be delivered over a wire, through a guide catheter (or a sheath or balloon guide catheter) to a clot fact, e.g., proximate the clot. The tractor tube may then be aligned so that it warps around and over the distal end of the elongate inversion support catheter and rolls into (everts) the elongate inversion support catheter. Once in positioned (against the face of the clot), the elongate inversion support catheter may be pushed distally while pulling proximally on the puller to ingest the clot, until the full length of the tractor tube is pulled proximally and rolled into the elongate inversion support catheter, unless the apparatus includes a stop to prevent it from entering the elongate inversion support catheter. Aspiration may be applied through the elongate inversion support catheter and/or the puller (when a puller micro catheter is used) to ensure that the clot remains in contact with the distal end of the elongate inversion support catheter and tractor. The intermediate catheter may then be advanced to the distal end of the elongate inversion support catheter (and aspiration may be applied through the intermediate catheter. The elongate inversion support catheter may be withdrawn proximally through the intermediate catheter while applying aspiration, which may both ease retraction of the apparatus within the intermediate catheter and may remove any residual clot portions.

Figure 9A:
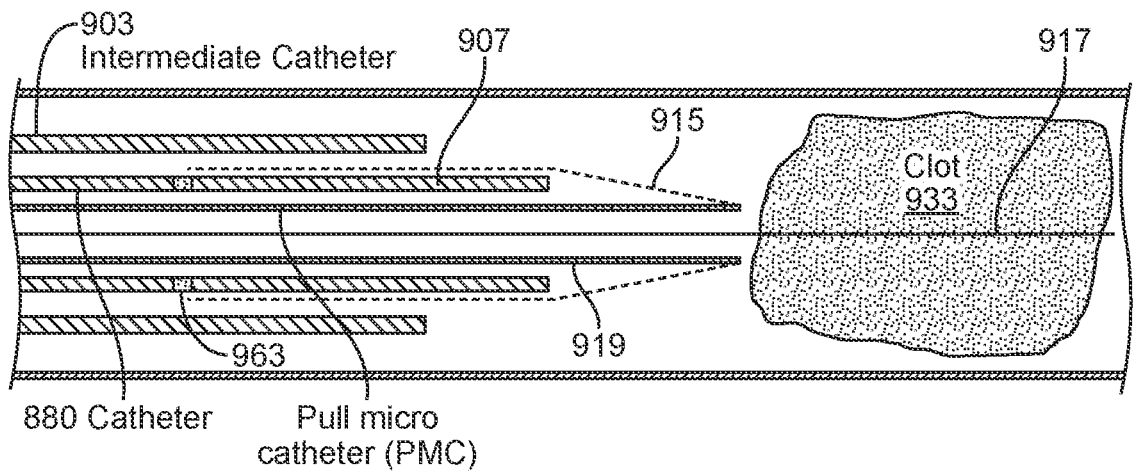
FIGS. 9A-9K illustrate one method of delivering and deploying an inverting tractor mechanical thrombectomy apparatus pre-loaded into an intermediate catheter such as the one shown in FIGS. 3A-3B. Similar methods may be employed to deliver the pre-loaded variations shown in FIGS. 4A and 5A.
Figure 9B:
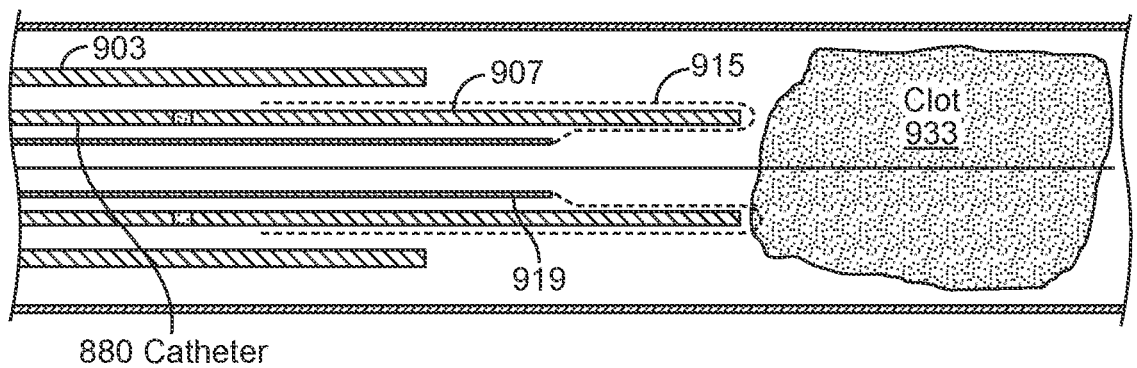
Figure 9C:
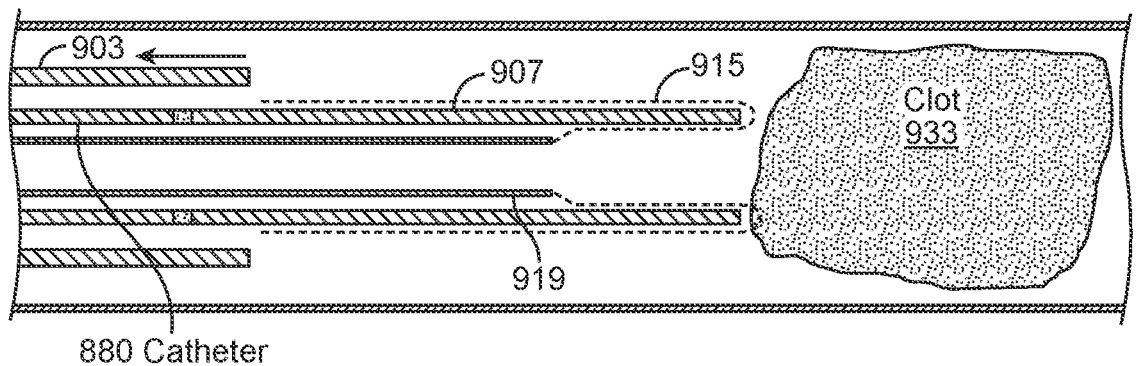
Figure 9D:
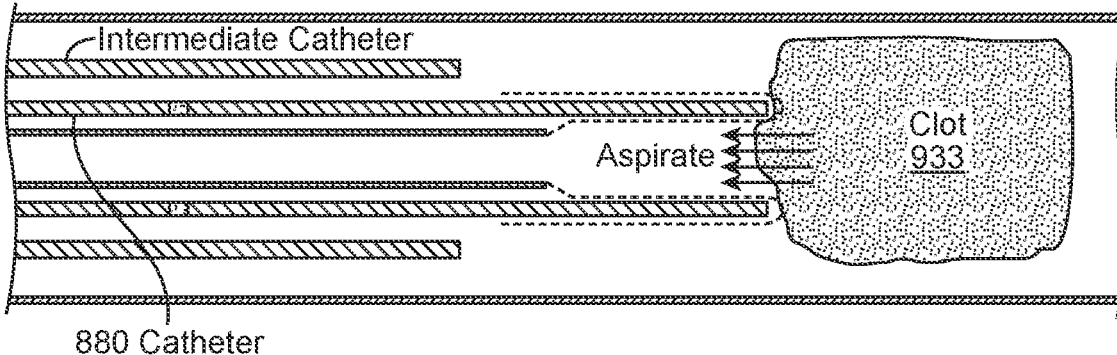

For example, in FIG. 9A, the apparatus has been delivered to the region adjacent to the clot and deployed out of the intermediate catheter 903. The elongate inversion support catheter 907 and puller 919 are advanced together distally to the clot 933 face over a guidewire 917. The elongate inversion support catheter includes a marking 963 that is visible under, for example, fluoroscopy or other imaging modality. In FIGS. 9A-9K this marking on the elongate inversion support catheter is a band. In FIG. 9B, the elongate inversion support catheter is advanced distally while simultaneously or sequentially pulling the puller proximally so that the tractor tube is rolled over the distal end opening of the elongate inversion support catheter and extends slightly within the elongate inversion support catheter (shown biased against the inner diameter of the elongate inversion support catheter). The tractor extending out of the elongate inversion support catheter is pushed against the clot face. In FIG. 9B, the guidewire has been left in place; alternatively, as shown in FIG. 9C, the guidewire may be removed. Alternatively, or additionally, the intermediate catheter 903 may be withdrawn proximally, which may fully unsheathe the tractor, including the distal end of the tractor. This may permit the tractor tube to roll freely over the distal end of the elongate inversion support catheter. The intermediate catheter may be locked to the elongate inversion support catheter, so that the two catheters move together wile drawing the puller proximally to roll the tractor tube over the elongate inversion support catheter, as shown in FIG. 9D. In this example, aspiration (e.g., vacuum) may also be applied, e.g., from within the puller and/or elongate inversion support catheter, which may help the rolling tractor to engage with the apparatus, even before rolling the tractor into the elongate inversion support catheter by withdrawing the puller proximally.

Figure 9E:
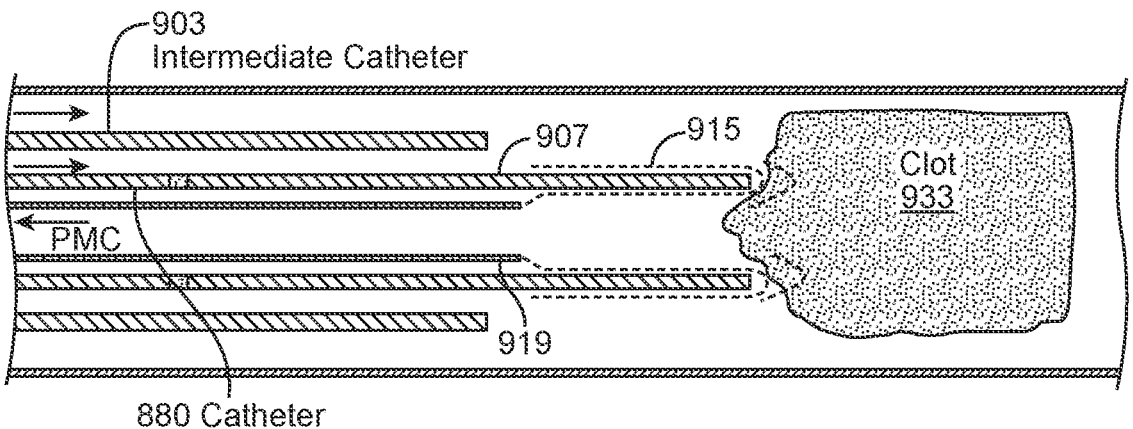
Figure 9F:
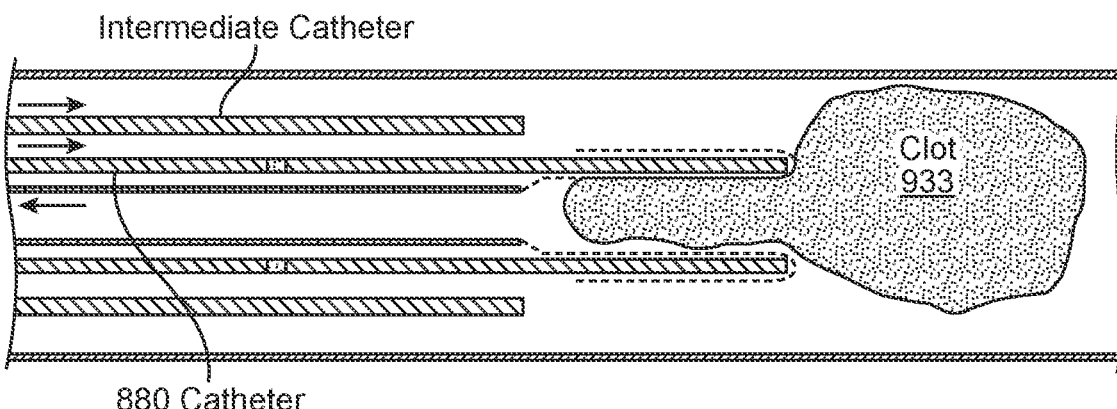
Figure 9G:
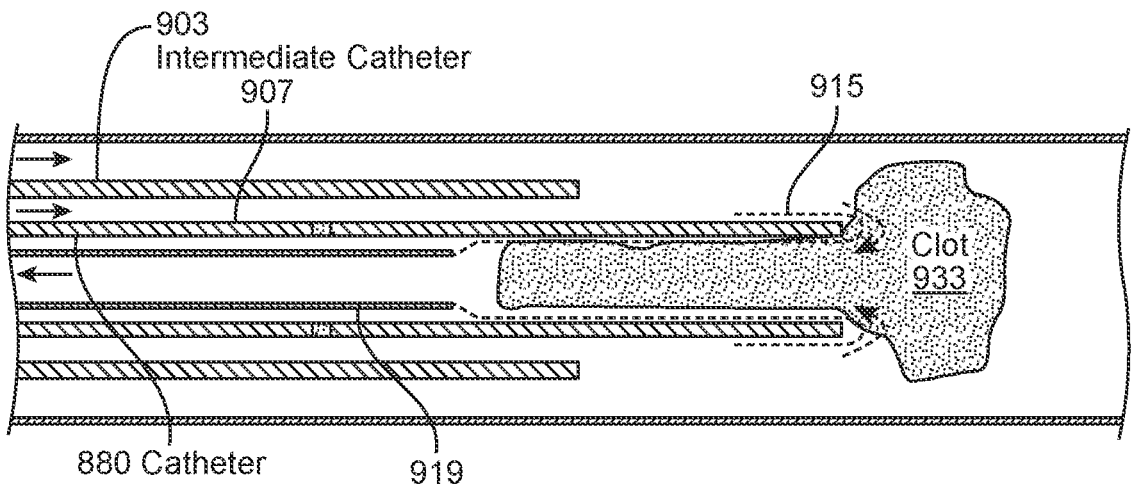
Figure 9H:
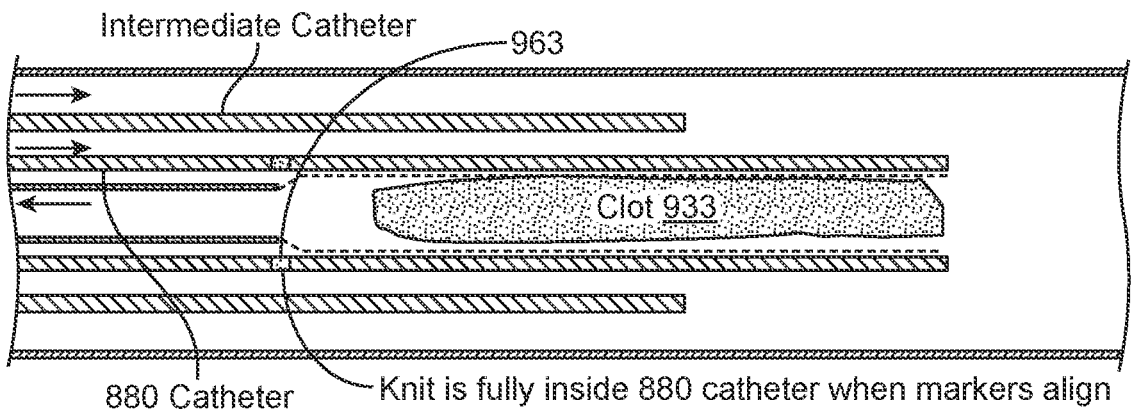
Figure 9I:
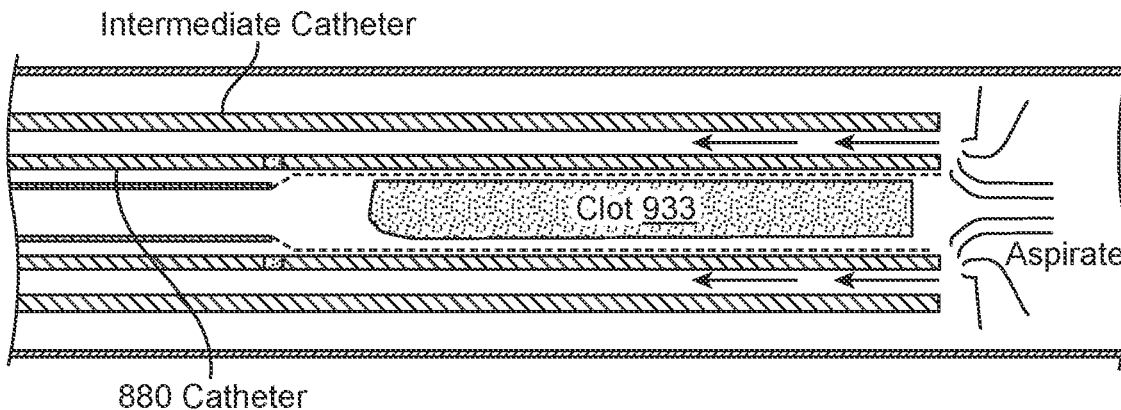
Figure 9J:
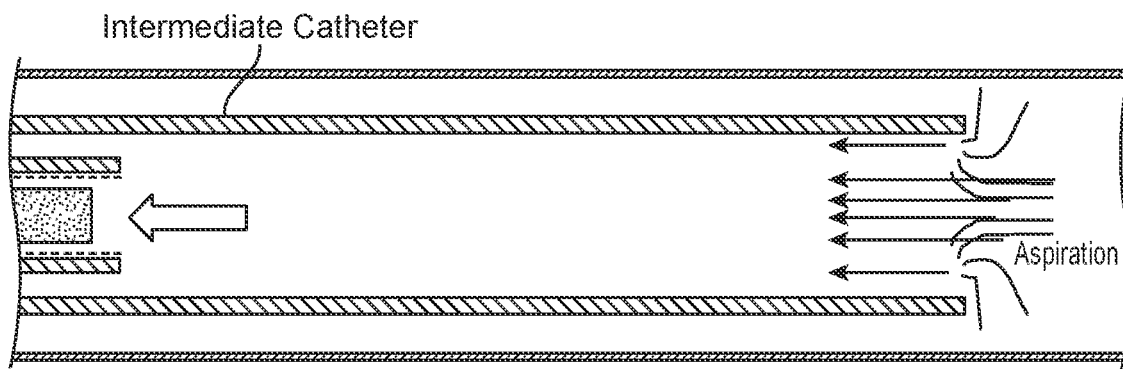
Figure 9K:
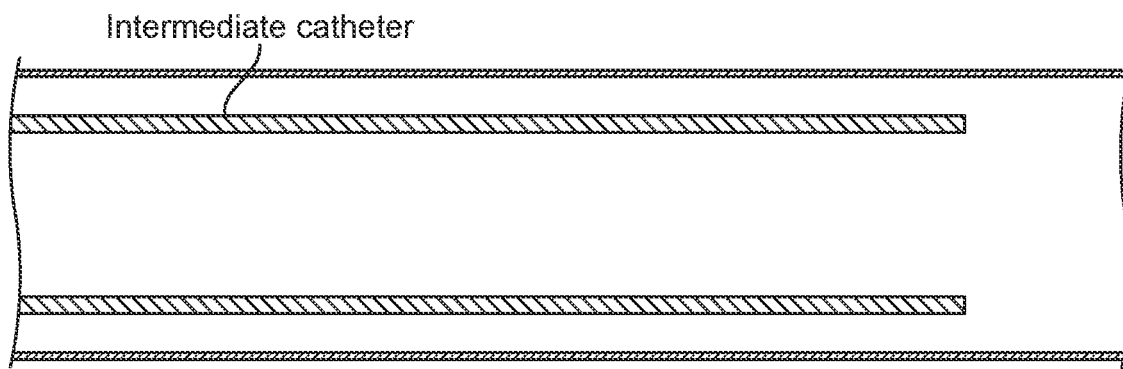

As shown in FIG. 9E, the puller 919 (PMC) may be drawn proximally while the elongate inversion support catheter 907 is advanced towards/into the clot. As previously mentioned, the intermediate catheter 903 may optionally be advanced with the elongate inversion support catheter (e.g., the two may be coupled together for this portion of the method. This step may be continued to ingest the clot. FIG. 9F shows the clot 30% ingested while still rolling the tractor tube into the elongate inversion support catheter (e.g., by pulling on the puller and/or pushing on the elongate inversion support catheter). FIG. 9G shows the clot 80% ingested and rolling into the elongate inversion support catheter. By FIG. 9H, the tractor tube has been fully withdrawn into the elongate inversion support catheter. In this example, the marker 963 on the elongate inversion support catheter aligns with either a marker on the puller or the puller itself (if it is visible under imaging). FIG. 17 shows another example of an elongate inversion support catheter (slotted 1709 to have a high column strength and high flexibility) in which the distal end region 1707 is marked with a platinum material to make it visible when imaging (e.g., with fluoroscopy). In FIGS. 9A-9H, the entire clot (100%) is captured by the tractor tube within the elongate inversion support catheter once the entire tractor tube has been rolled into the elongate inversion support catheter. However, this is not necessarily the case, as will be described below, in some variations additional clot may be drawn into the elongate inversion support catheter and/or the intermediate catheter by applying a combination of mechanical action (e.g., pulling the clot with the portion captured by the tractor and suction. For example, FIG. 9I shows the (optional) use of aspiration through the intermediate catheter (and in some cases, the elongate inversion support catheter). The aspiration may be left on while withdrawing the apparatus proximally, as shown in FIG. 9J. As mentioned, this may remove any remaining clot. Alternatively, or additionally a second apparatus may be installed through the intermediate catheter and delivered to the deployment site (with the intermediate catheter left in position. Finally, as shown in FIG. 9K, an angiogram may be performed through the intermediate catheter to confirm that the vessel is opened. If not, additional procedures (e.g., another preloaded assembly of an inverting tractor mechanical thrombectomy apparatus may be inserted and used to remove clot) may be performed.

In general, when deploying any of the inverting tractor mechanical thrombectomy apparatuses described herein, and in particular, the pre-loaded inverting tractor mechanical thrombectomy apparatuses, the deployment may include the general steps described below. These steps may be customized as indicated herein. First, obtaining access with sheath to the patient's common carotid or ICA. Inject contrast through the sheath to image the vessel. Before, during or shortly after, on the back table (e.g., where the proximal end of the mechanical thrombectomy apparatus is held/prepared), flush the intermediate catheter (I.C.) and connect it to a first rotating hemostatic valve (RHV A), then introduce the elongate inversion support catheter ("880 Device"), puller and tractor through RHV A, e.g., using a peel-away sheath. The elongate inversion support catheter may then be positioned relative to the I.C., e.g., within about 1 cm proximal to the tip of the I.C., as shown in FIG. 3A, and locked in position relative to the I.C. RHV A may then be tightened. A second RHV (e.g., RHV B) may be coupled to the pusher and flushed, and RHV A may be flushed as well. Flush lines may be connected. A guide wire may be loaded through the apparatus. The puller may be locked in position (e.g., as shown in FIG. 3A, extending approximately 1 cm or more from the distal end opening of the I.C.) for tracking.

The apparatus may then be tracked to the desired location (e.g., near the clot). Once in position, the apparatus may be used to perform the thrombectomy. For example, RHV A and B may be loosened. The coupling between the elongate inversion support catheter and the I.C. may be released, as may any coupling between the puller and the I.C. and/or elongate inversion support catheter. The elongate inversion support catheter may be advanced over the puller until its distal end meets the distal connection between the tractor tube and the puller. The I.C. may be pulled back to unsheathe the tractor tube. The elongate inversion support catheter and I.C. may again be locked in position relative to each other. RHV A may be tightened, and the elongate inversion support catheter may be advanced to the clot face (possible with aspiration through the puller). With a slight pressure forward (distally) on the pusher (and/or I.C.), the puller may be pulled slowing proximally to ingest the clot. Alignment markers on the elongate inversion support catheter and the tractor (e.g., a region at the end of the tractor tube on the outside of the elongate inversion support catheter, or a region of the puller) may be monitored to indicate when the tractor tube is completely inverted into the elongate inversion support catheter, and the user may stop pulling proximally on the puller. RHV A may be loosened and the IC may be advanced, with aspiration, over the elongate inversion support catheter, which may remove any excess clot or pieces of clot. The elongate inversion support catheter, puller and tractor may then be withdrawn proximally through the I.C. The I.C. may remain in position and contrast applied to again image through the vessel and a TICI score determined.

Figure 10A:
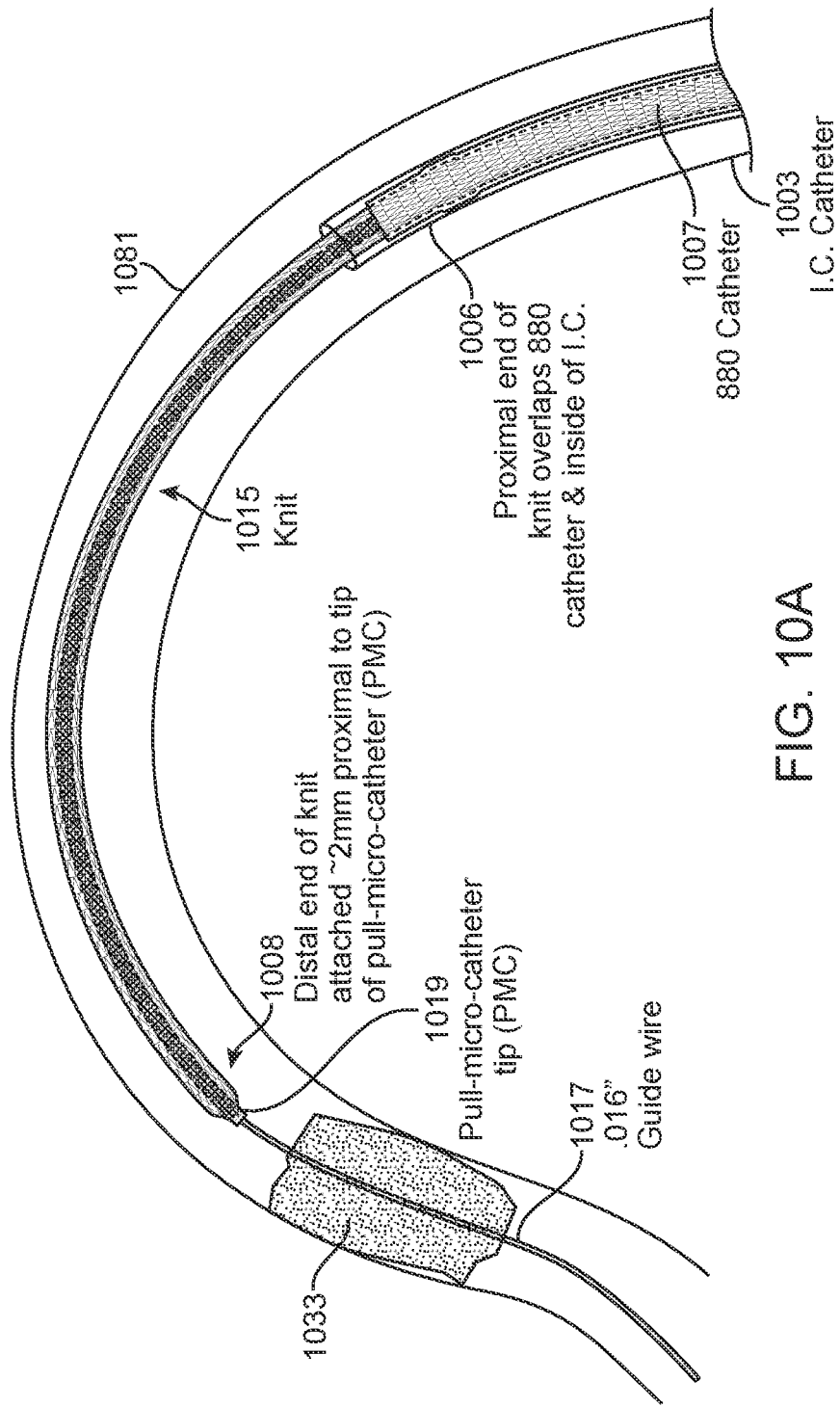

Another example of the operation of a pre-loaded assembly of an inverting tractor mechanical thrombectomy apparatus is shown in FIGS. 10A-10D. For example, in FIG. 10A, the pre-assembled apparatus is similar to that shown in FIG. 3A, above. The apparatus includes an intermediate catheter 1003 that entirely houses the elongate inversion support catheter 1007 during the tracking through the tortious vessel 1081. A puller (pull micro catheter 1019) passes through the elongate inversion support catheter, and include a tractor tube (shown as a knit tractor tube 1015) extends from an attachment site 1008 approximately 2 mm proximal to the distal end of the puller. The opposite end of the tractor tube is held between the elongate inversion support catheter and the intermediate catheter (within the intermediate catheter). In FIG. 10A, the guidewire 1017 has been inserted distally to and through a clot 1033, and the pre-loaded assembly of the inverting tractor mechanical thrombectomy apparatus is locked (e.g., so that the puller extends distally a predetermined distance and the elongate inversion support catheter is locked relative to the intermediate catheter) and advanced distally over the guide wire until it reaches the clot face.

Figure 10B:
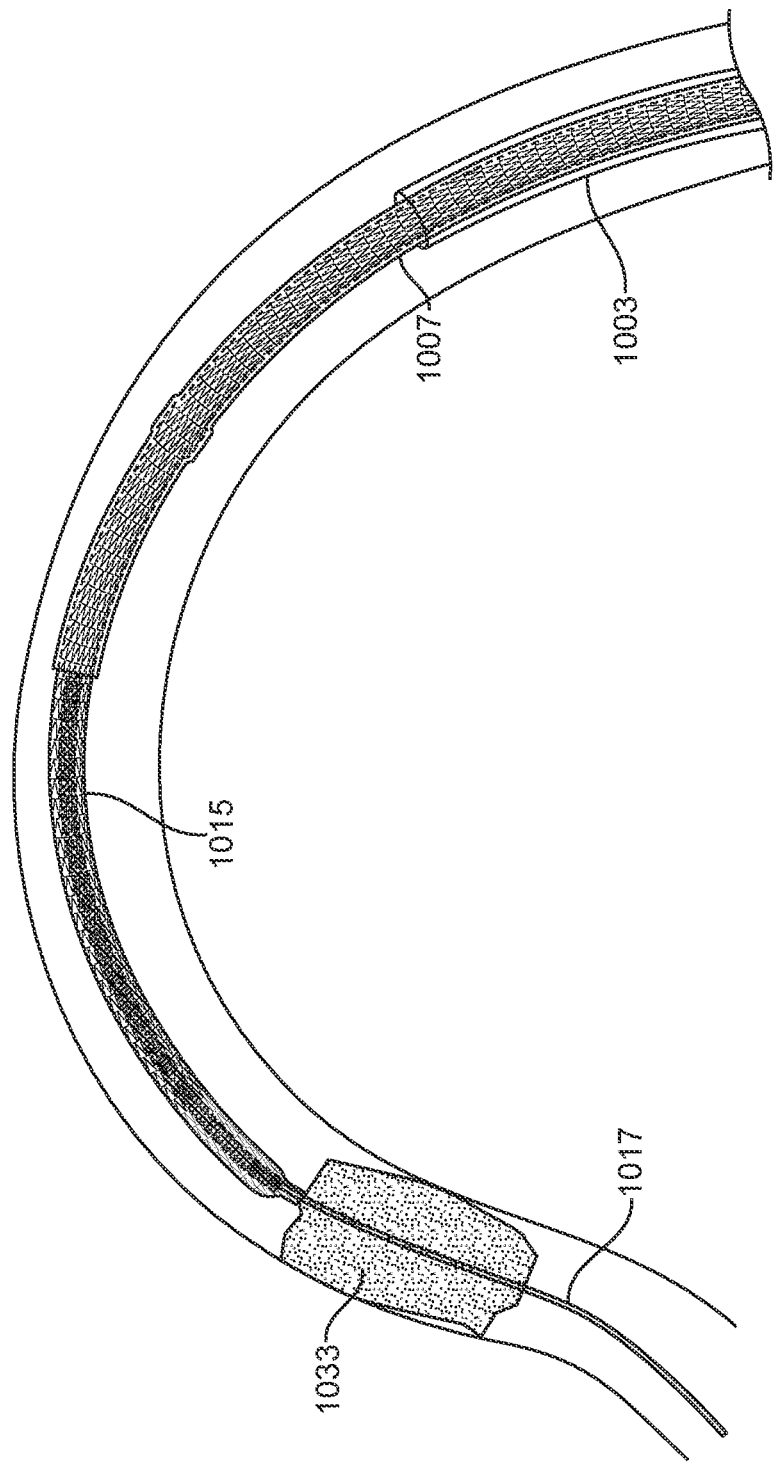
Figure 10D:
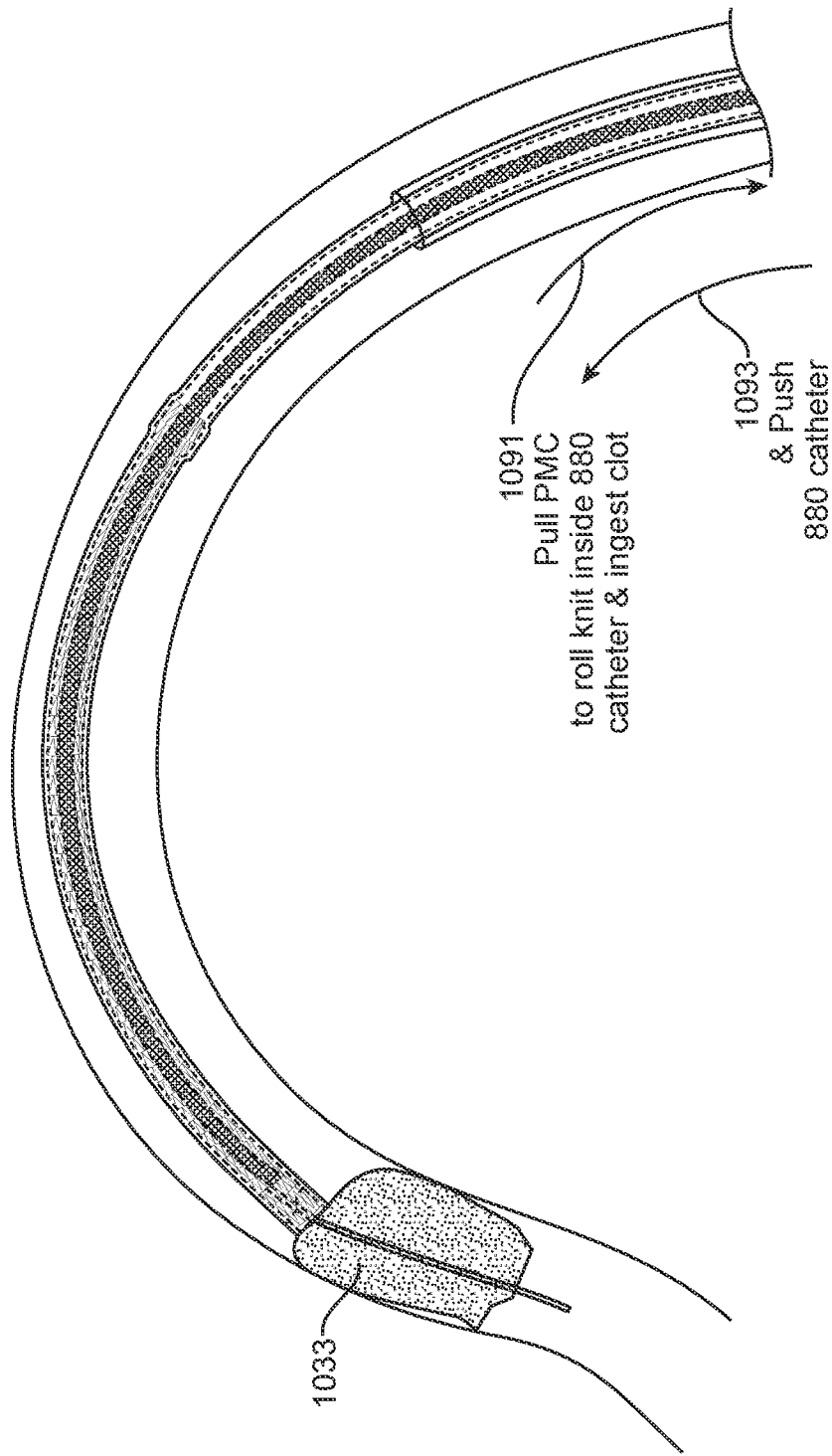

In FIG. 10B, the puller distal end is adjacent to the clot face, and the puller may be locked in position (e.g., at the handle) while the elongate inversion support catheter is unlocked from the intermediate catheter and advanced distally over the puller and between the gap formed by the tractor tube. In this example, as the elongate inversion support catheter is advanced distally, the tractor tube may compress to a compressed/jammed state, particularly when a knit material is used, before the elongate inversion support catheter slides within its inner diameter. In FIG. 10C, the elongate inversion support catheter is advanced distally 1068 over the puller (and under the tractor tube) until the distal end of the elongate inversion support catheter is aligned with the clot, as shown. Finally, as shown in FIG. 10D, the puller may be pulled proximally 1091 while the elongate inversion support catheter is pushed distally 1093 to roll the tractor into the elongate inversion support catheter and capture the clot 1033.

Figure 11A:
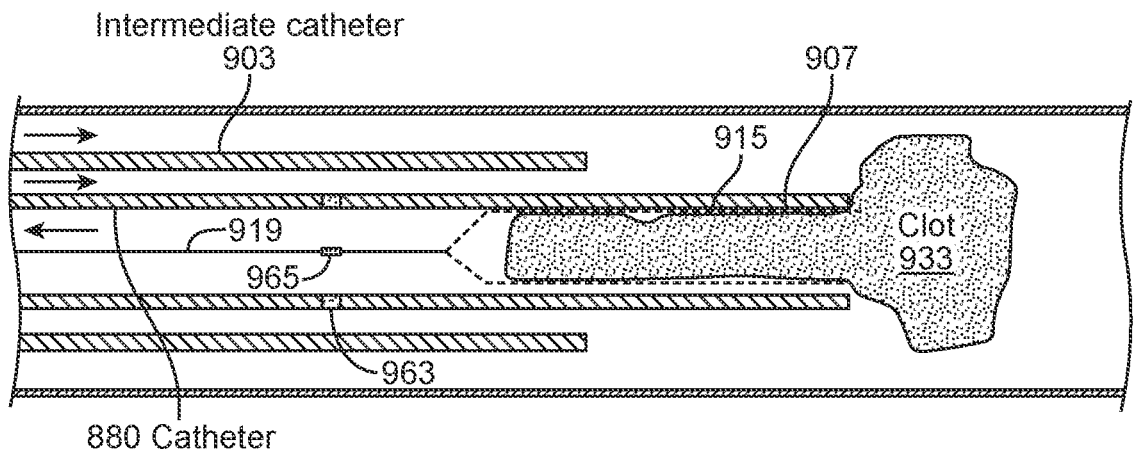
FIGS. 11A-11C illustrate a method of using an inverting tractor mechanical thrombectomy apparatus to remove clot after the tractor tube portion of the inverting tractor mechanical thrombectomy apparatus has been completely withdrawn into the elongate inversion support catheter.
Figure 11B:
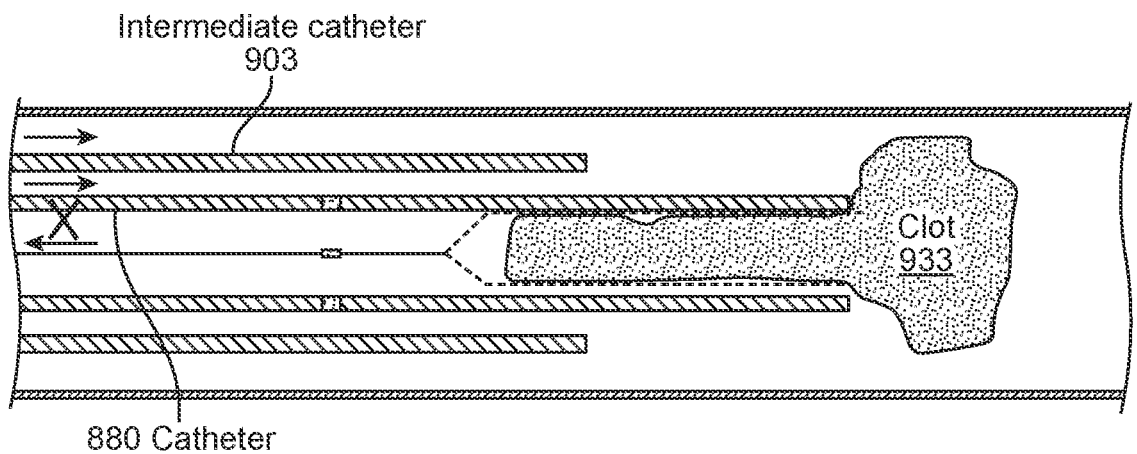
Figure 11C:
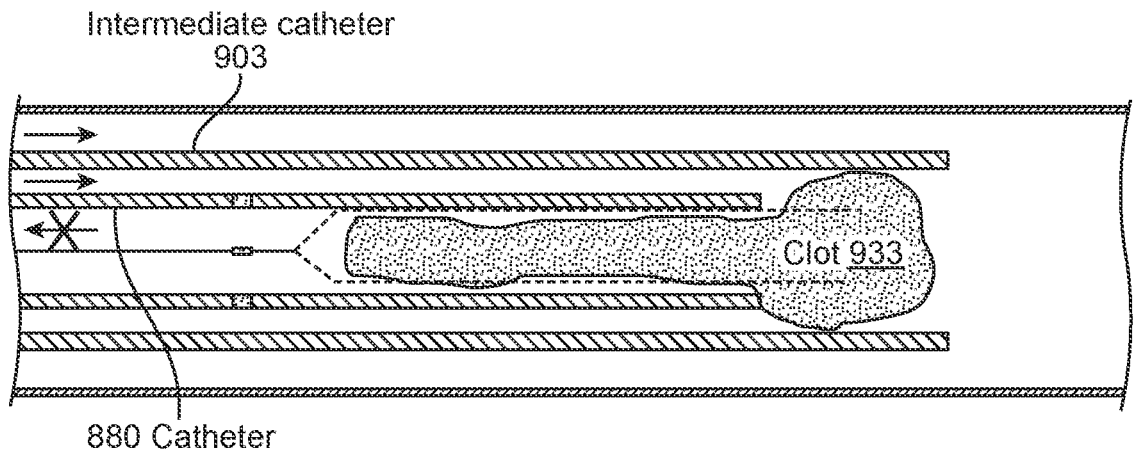

As discussed above, in some variations the tractor tube may be completely rolled into the elongate inversion support catheter before a clot has been completely removed. In such cases, it may be helpful to ensure that the clot is not ripped or fragmented during the process. In order to prevent this, the apparatus may be adapted to limit the movement of the puller and/or the tractor, in addition to (or instead of) using the vacuum and intermediate catheter, as described above. FIGS. 11A-11C illustrate an example in which the clot is too long for the tractor tube apparatus to fully engulf. In FIG. 11A, similar to FIG. 9H, the clot has been captured by the tractor tube 915, which is shown fully retracted into the elongate inversion support catheter 907. The user may detect that the tractor tube has been fully retracted because either the puller 919 maybe limited to prevent it moving further proximally when the tractor tube is fully retracted into the elongate inversion support catheter. Alternatively, or additionally, the tractor tube may include a first marker 963 that may align with a marker on the puller 965 when the tractor tube is fully retracted, as shown in FIG. 11A. Unlike FIG. 9H, however, in this example, the clot has not been fully captured, and some of it remains outside of the tractor and elongate inversion support catheter.

If the clot is not fully captured by the apparatus, there is a risk that continuing to pull on the clot may disrupt it, e.g., cutting it into fragments. To avoid this, the apparatus may be configured to prevent the user from continuing to apply force to the clot once the tractor has been fully deployed. As mentioned, the user may be instructed to stop drawing the puller proximally once one or more markers indicate that the tractor tube has been retracted to a predetermined position. In particular, it may be beneficial to prevent the tractor tube from fully inverting over the tractor tube, as described in FIG. 12A, below.

In some variations, the apparatus may include a stop (e.g., in a handle region) preventing or limiting the puller to prevent it from extending beyond a predefined limit. For example, the limiter or puller stop may be configured as a physical stop on the puller portion of a handle that limits the travel of the puller.

FIGS. 11B-11C illustrate a method for handling this situation without tearing (and risk harming the patient). In FIG. 11B the elongate inversion support catheter is stopped from advancing any further distally, and instead the intermediate catheter may be advanced distally (with or without aspiration through the intermediate catheter). In FIG. 11C, the clot, including the portion outside of the elongate inversion support catheter, has been fully captured within the intermediate catheter, as shown.

Figure 12A:
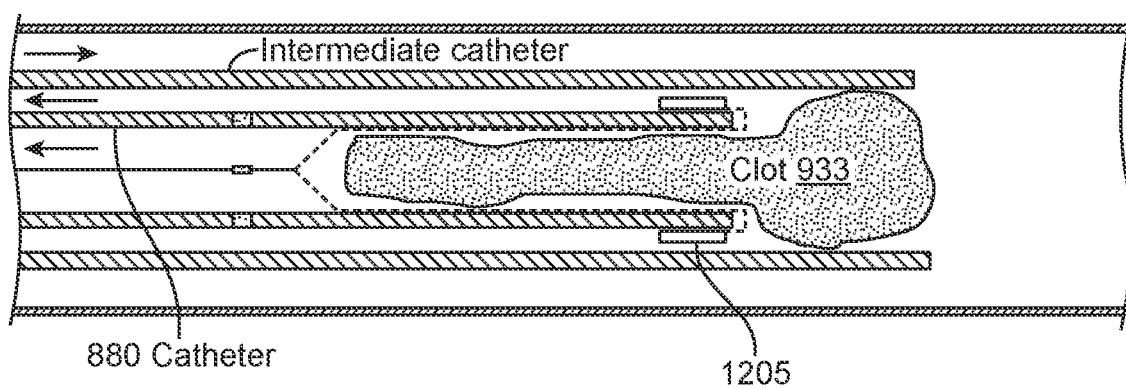
FIG. 12A illustrates an inverting tractor mechanical thrombectomy apparatus configured to prevent the tractor tube from retracting fully into the elongate inversion support catheter.
Figure 12B:
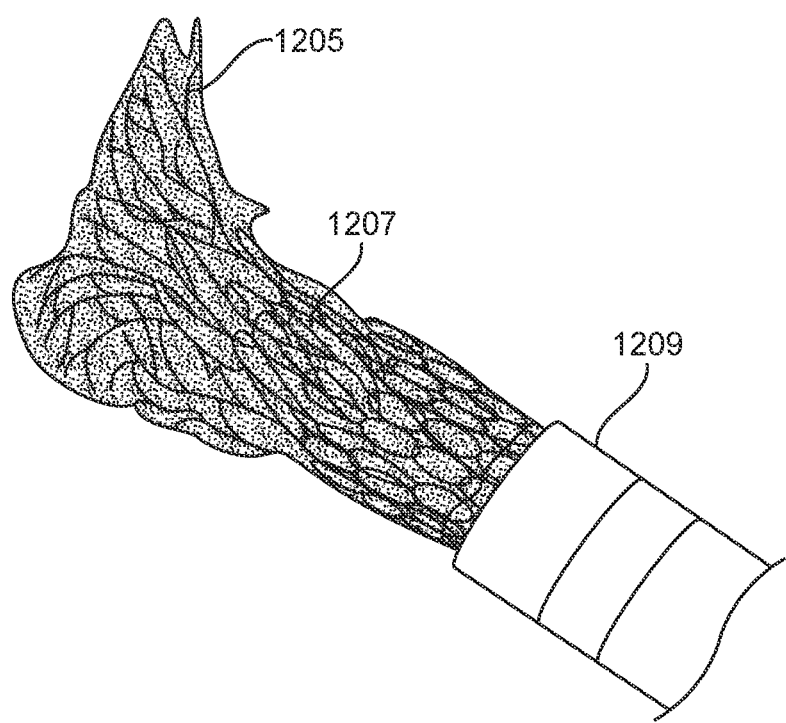
FIG. 12B shows an example of a cuff on the distal end of an inverted flexible tube.

FIG. 12A illustrates another example of a configuration of the apparatus (and in particular the tractor tube) in which the distal end of the tractor tube is configured with a non-compliant material 1205 (e.g., a cuff) so that it cannot flip or roll over the distal end of the elongate inversion support catheter. This may prevent the user from pulling the tractor all the way around the catheter. In some variations, the cuff is configured to permit the tractor tube to flip over the distal end of the elongate inversion support catheter. For example, a cuff on the outer end of the tractor tube may include one or more slits (e.g., between one and 20 slits or slots) extending along its length configured to permit it to flip and invert, but providing an increase in the stiffness of the tractor tube. In any of these variations, the cuff on the outer end of the tractor tube may include a marker (e.g., radiopaque material); for example, the cuff may be a polymer including a platinum or other radiopaque material suspended in it. FIG. 12B illustrates an example of a cuff 1205' at one end of a flexible tube ('tractor') 1207 that has been inverted over the inversion support catheter 1209.

Figure 13A:
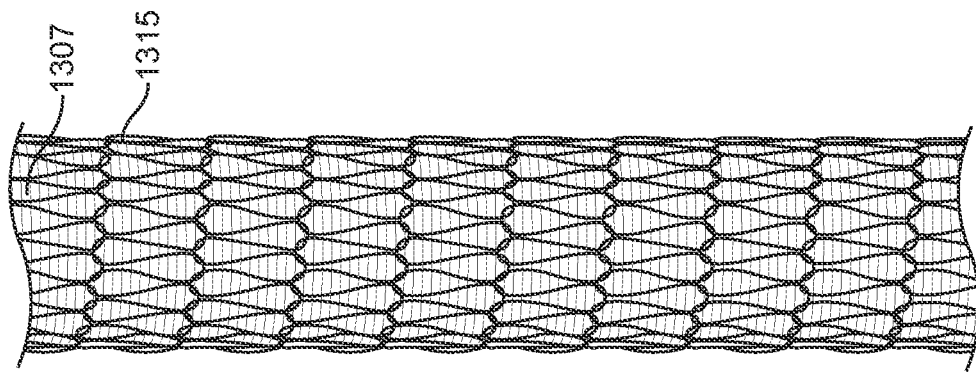
FIG. 13A shows a knitted tractor tube extending in an inverted configuration over the outside of a distal end of an elongate inversion support catheter.

As mentioned above, any of these apparatuses may include one or more features that may be used to improve tracking, and in particular, by preventing the elongate inversion support catheter from stiffening. This may be a problem with the high column-strength, highly flexible elongate inversion support catheters that include one or more slot or cut-out regions along their length. One feature that may be included, discussed above, is the use of configurations in which the tractor tube, and particularly knitted tractor tubes, are delivered in a compressed state, rather than a stretched state. As mentioned above, pinning one end of the tractor tube in the intermediate catheter may be configured to do this in some of the preloaded configurations described above. FIGS. 13A-16B illustrate other variations. For example, FIG. 13A shows a knitted tractor tube 1315 over an elongate inversion support catheter 1307 that is stretched. The woven links are connected end-to-end (forming a helical winding pattern around the elongate inversion support catheter). FIG. 13B illustrates the resulting compressive load on the catheter tip in this configuration; friction loads on the knit during tracking may pull on the distal end of the elongate inversion support catheter, causing it to stiffen in compression. However, such compressive loads may be lessened or eliminated by using a woven material held in a compressed configuration, as shown in FIG. 13C. In this example, the interlocking loops forming the weave are overlapping in a compressed state.

Figure 14D:
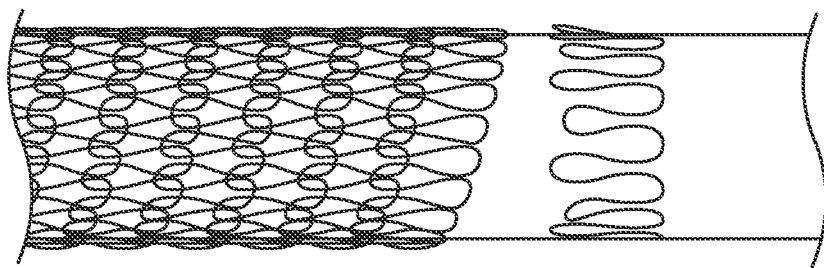
FIGS. 14A-14D illustrate examples of inverting tractor mechanical thrombectomy apparatuses (e.g., elongate inversion support catheter portions) including a stop that is configured to hold the knitted tractor tube in a compressed configuration.
Figure 14C:
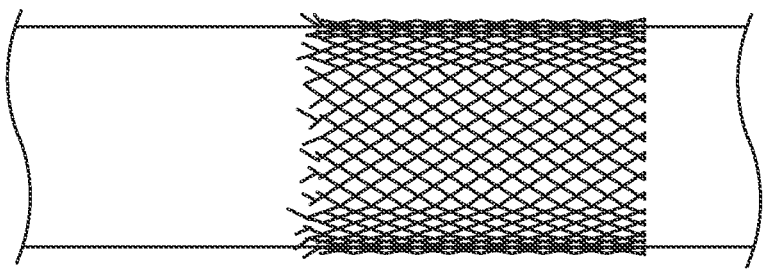
Figure 14B:
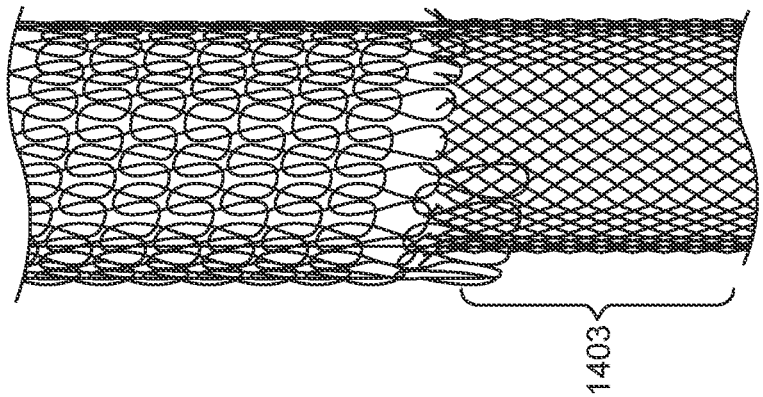
Figure 14A:
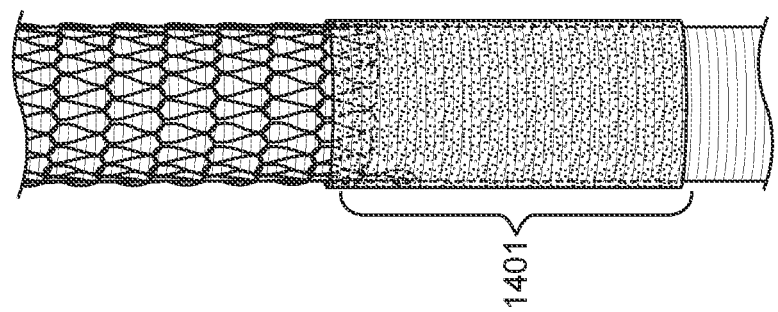

This compressed state may be maintained by pinning, securing or holding one or more ends or lengths of the tractor tube in place when the tractor tube is compressed. Any appropriate mechanism for holding the compression may be used. For example, the apparatus may include a stop or lock to engage with one or more regions of the tractor tube and hold it in a compressed configuration during tracking. FIGS. 14A-14D illustrate variations of structures (stops) that may be used to hold the woven tractor tube on the outside of the elongate inversion support catheter in a longitudinally compressed state. In FIG. 14A, the elongate inversion support catheter includes a polymeric lip, ridge or rim (stop) 1401 that may secure one end of the woven tractor tube against the elongate inversion support catheter with the tractor tube in compression. Distal force may be applied to pull the tractor tube out of the stop (not shown). FIG. 14B shows a Nitinol (NiTi) braid 1403 that holds the knitted tractor tube in compression along the length of the elongate inversion support catheter. FIG. 14C shows a similar NiTi braids with exposed ends that engage with the knit of the tractor. FIG. 14D a NiTi knit segment also includes projections that engage with the knit, as shown.

Figure 15A:
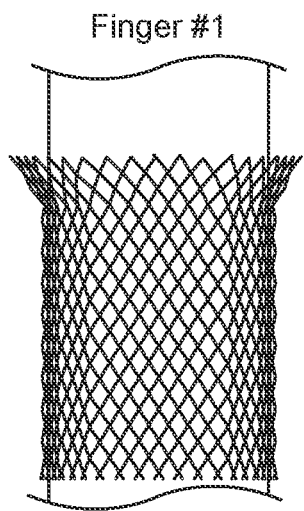
FIGS. 15A-15G illustrate examples of finger-like stop elements similar to those shown in FIGS. 14B-14C. The distally-directed prongs, filaments or fingers of the stops shown may be placed anywhere along the length of the outer surface of the elongate inversion support catheter to prevent compression of the knitted tractor tube during delivery and deployment.
Figure 15B:
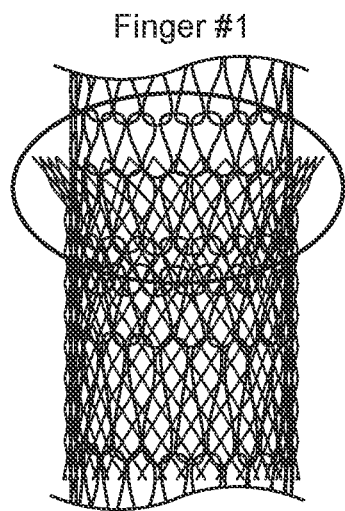
Figure 15C:
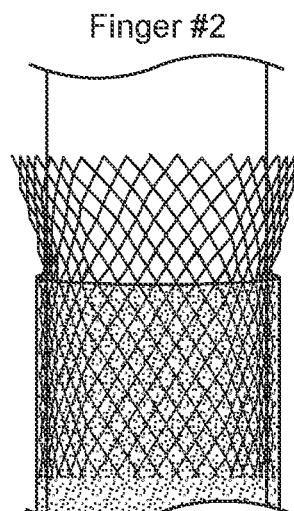
Figure 15D:
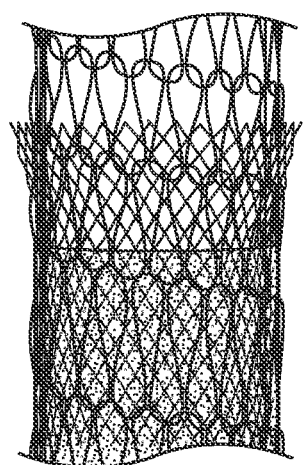
Figure 15E:
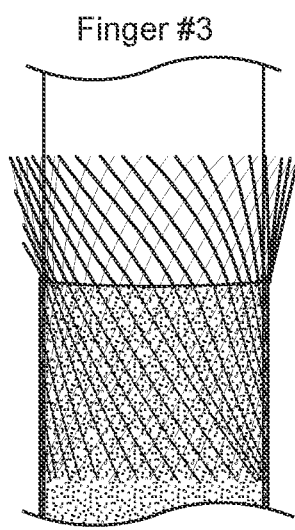
Figure 15F:
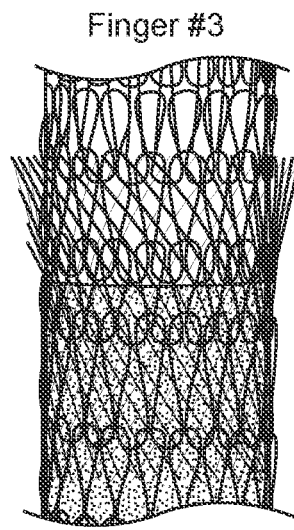
Figure 15G:
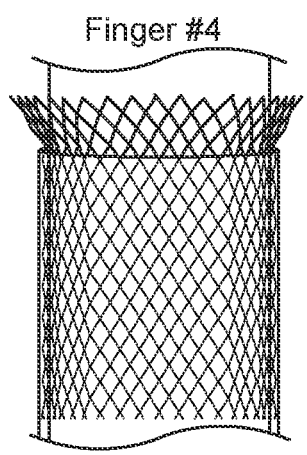
Figure 15H:
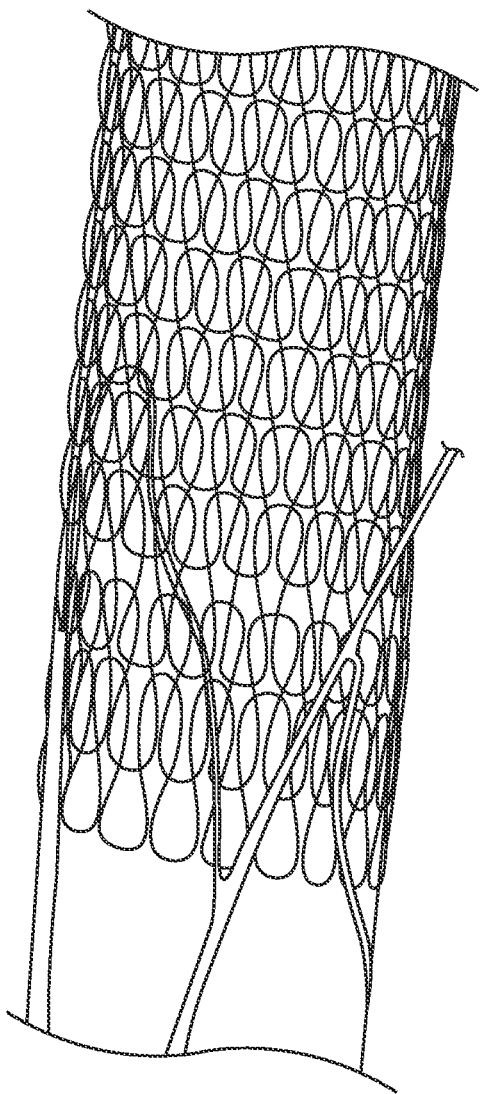
FIG. 15H is another example of a stop on the outer surface of and elongate inversion support catheter having distally-facing prongs that prevent proximal movement of a woven tractor tube, in order to prevent compressive forces on the elongate inversion support catheter.

FIGS. 14A-14G show similar finger-like elements that may be used to engage with the knit (the loops formed by the knit) of the tractor. In FIG. 15A. the loose ends of the woven material form short "fingers" that are exposed and engage with the knitted tractor, as shown in FIG. 15B. In FIG. 15C, as similar construction having longer "fingers" of loose ends is shown, and FIG. 15D shows the fingers engaging with the knitted tractor tube. FIG. 15E shows "fingers" formed by the loose ends of the weave located approximately 1 cm from the tip of the elongate inversion support catheter, and FIG. 15F shows these elements engaging the knitted tractor tube. FIG. 15G is another example of a set of fingers formed of projecting metal wires that may be used to removably hold the tractor tube against the elongate inversion support catheter in compression. FIG. 15H shows an example of a variation formed by a metal wire having very long "fingers", engaged with a knitted tractor tube, holding it in compression.

Figure 16A:
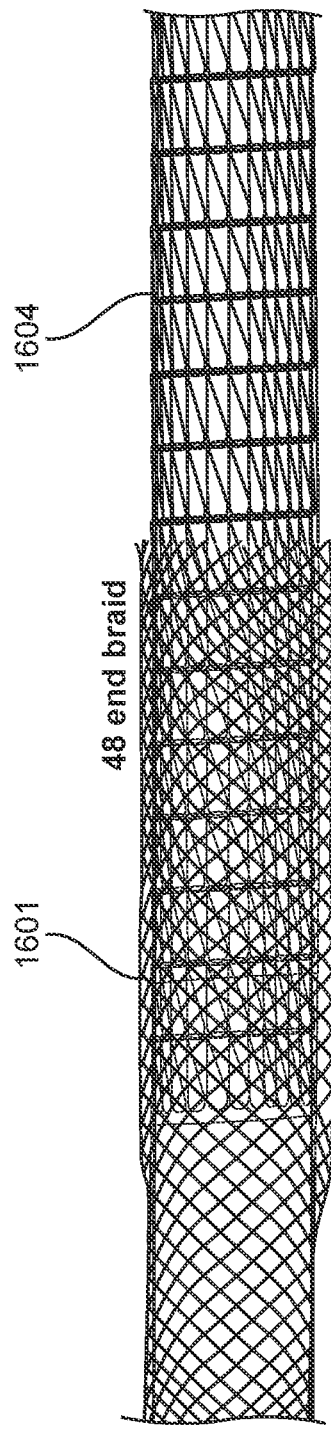
FIGS. 16A and 16B illustrate examples of annular housings ("garages") for the tractor tube on the outer surface of an elongate inversion support catheter that may also maintain the tractor tube in a compressed configuration on an outer surface of the apparatus, preventing it from applying compressive force on the distal end of the elongate inversion support catheter.
Figure 16B:
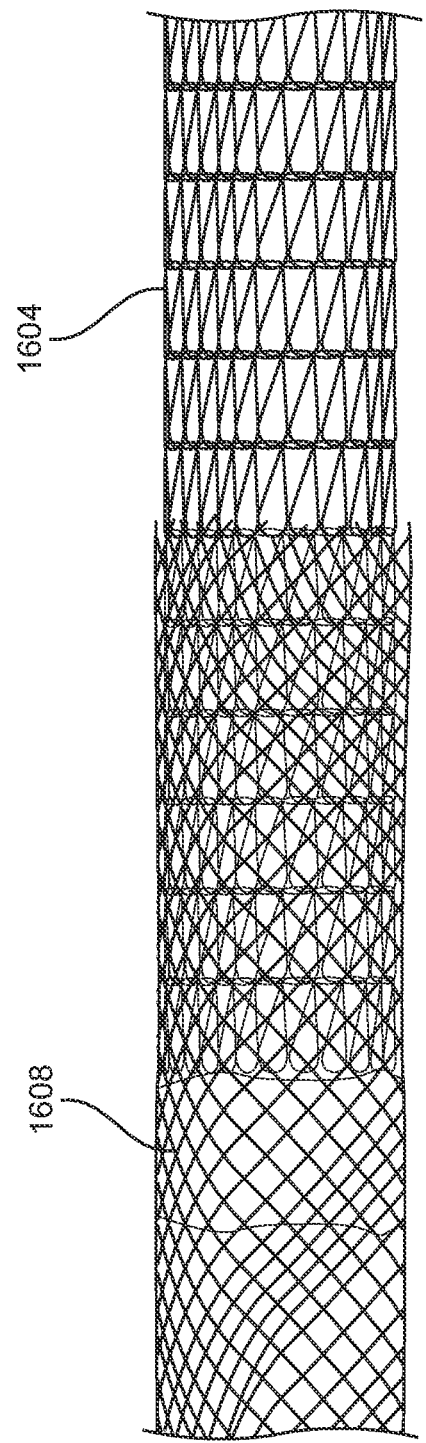

Alternatively, or additionally, any of these apparatuses may include a housing or garage that may be used to hold the knitted tractor tube in compression. For example, FIGS. 16A and 16B illustrate one example of this configuration, in which a housing ('garage') region 1602 formed of a 48-end braided material, is used to hold the knitted tractor tube 1604 in a compressed state at one of its ends on the elongate inversion support catheter. FIG. 16B shows a similar example of a elongate inversion support catheter having a 10 mm long 'garage' region made of a braided material 1608.

Removal of Large Clots

Any of the mechanical thrombectomy apparatuses described herein may be adapted to remove large clots. In general, a large clot may be large in either or both diameter (outer diameter) and length, and may be large relative to the mechanical thrombectomy apparatus. For example, the clot may have a diameter that is larger than the diameter of the apparatus (e.g., larger than the expanded diameter of the flexible tube which captures the clot). Thus, the apparatus may be configured to capture and compress the clot so that it may be withdrawn from the lumen of the vessel, into the lumen of the intermediate catheter and/or inversion support catheter. The apparatus may also be configured to capture and remove clots that are longer than the ability of the flexible tube to hold.

Figure 18F:
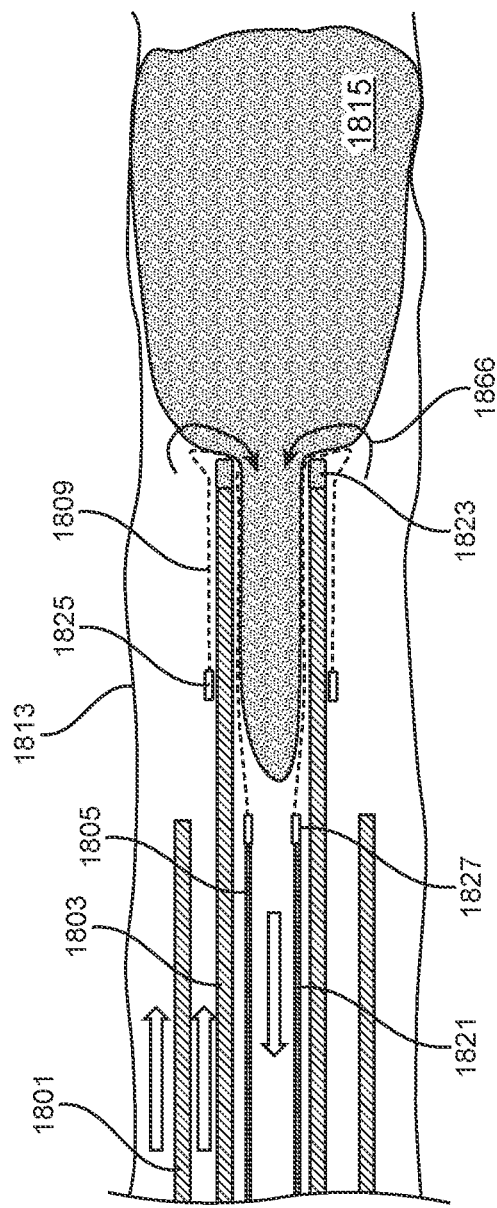

In general, FIGS. 18A-18J show a method of removing a clot 1815 from a vessel 1815 as described herein, in which a vacuum (suction) may be applied through the puller to make and confirm initial contact with the clot. For example, FIGS. 18A-18B illustrate an example of an apparatus that is preloaded and configured to both track to the clot and to remove the large-diameter clot 1815. For example, in FIG. 18A, the apparatus (mechanical thrombectomy apparatus or inverting tube apparatus) includes an intermediate catheter (IC) 1801, an inversion support catheter ("outer catheter") 1803 within a lumen of the intermediate catheter, a puller (shown as a puller catheter) 1805 within a lumen of the inversion support catheter, and a flexible tube (e.g., knit tube) 1809 extending over the inversion support catheter. The flexile tube has a first end 1826 coupled at a distal end region of the puller and a second end 1824 comprising a cuff 1825 that is less flexible that a region of the flexible tube adjacent to the cuff, wherein the flexible tube is configure to be pulled proximally into the inversion support catheter by pulling the puller proximally so that the flexible tube rolls and inverts over a distal end of the inversion support catheter 1823. The apparatus is shown over a guidewire 1807. In this example, multiple regions include markers that may be visualized, e.g., under fluoroscopy. For example, the end of the inversion support catheter includes a marker 1823, as does the distal end of the puller 1826. The puller may also include an intermediate marker 1821, shown aligned with the cuff 1825; the cuff also includes a marker. The assembly is shown within the vessel 1813.

The apparatus may be distally advanced over the guidewire and positioned adjacent to the clot 1815. The apparatus may initially be pre-loaded in a tracking configuration, in which the outer (inversion support) catheter 1803 is retracted into the lumen of the intermediate catheter 1801 while the puller (puller catheter 1805) with the attached flexible tube 1809 extending proximally from the distal end 1826, is moved distally to track over the guidewire. In FIG. 18B, the apparatus is adjusted into a clot-grabbing configuration in which the inversion support catheter 1803 is extended distally towards the distal end of the apparatus, although it is still positioned proximal to the puller distal end 1827. The intermediate catheter 1801 may also optionally be withdrawn proximally, as shown in FIG. 18C, which in some variations may allow the flexible tube to expand outwards (see, e.g., FIG. 26B).

FIG. 18C1 shows an example of a prototype device corresponding to the apparatus configured as shown in FIG. 18C. In this example the flexible tube is a woven flexible tube 1809 that is shown extending distally from the distal end face 1827 of the puller. The puller is shown over a guidewire 1807.

Figure 18G:
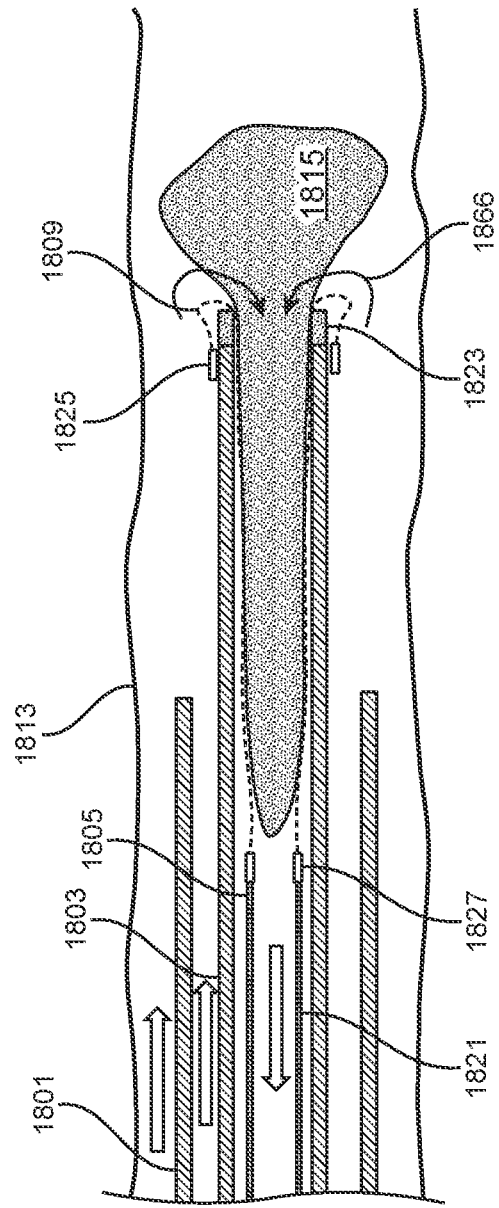

Once the apparatus is in position near the clot, suction may be applied through the puller catheter, as shown in FIG. 18D. This focal suction (aspiration) 1840 may be applied while advancing the apparatus distally to engage the clot, as shown in FIG. 18E. In some variations, the guidewire is left in place (not shown) or it may be optionally removed (as shown in FIGS. 18D-18E). Once the distal-facing end of the puller is engaged with the clot, as shown in FIG. 18E, connection to the clot may be detected by observing the flow and/or pressure through the puller from the suction 1840'. Thereafter, the puller may be drawn proximally and/or the inversion support catheter may be moved distally so that the flexible tube rolls over the distal end opening of the inversion support catheter (these motions are shown by the large arrows). In FIG. 18F, approximately 30% of the clot has been drawn into the inversion support catheter by rolling 1866 the flexible tube. In FIG. 18G, more, but not all (e.g., approximately 70%) of the clot has been ingested, though a substantial amount of clot remains outside of the inversion support catheter and flexible tube. The vacuum may be left on, or it may be turned off while pulling the puller proximally to engulf/grab the clot. Heavy arrows indicate movement of the components of the apparatus, such as the intermediate catheter, which may be advanced distally, the inversion support catheter, which may also be advanced distally, and the puller, which may be withdrawn proximally. These motions may be coordinated by the handle (not shown) and/or performed manually by the user. Once the flexible tube has reached the distal end of the inversion support catheter, it may stop or be stopped, to prevent it from rolling over the distal end. Rolling of the second end of the flexible tube over the inversion support catheter distal end may cut or break the clot off, which may be highly undesirable, as it may potentially release the clot, resulting in complications, and/or may require additional removal steps.

Figure 18H:
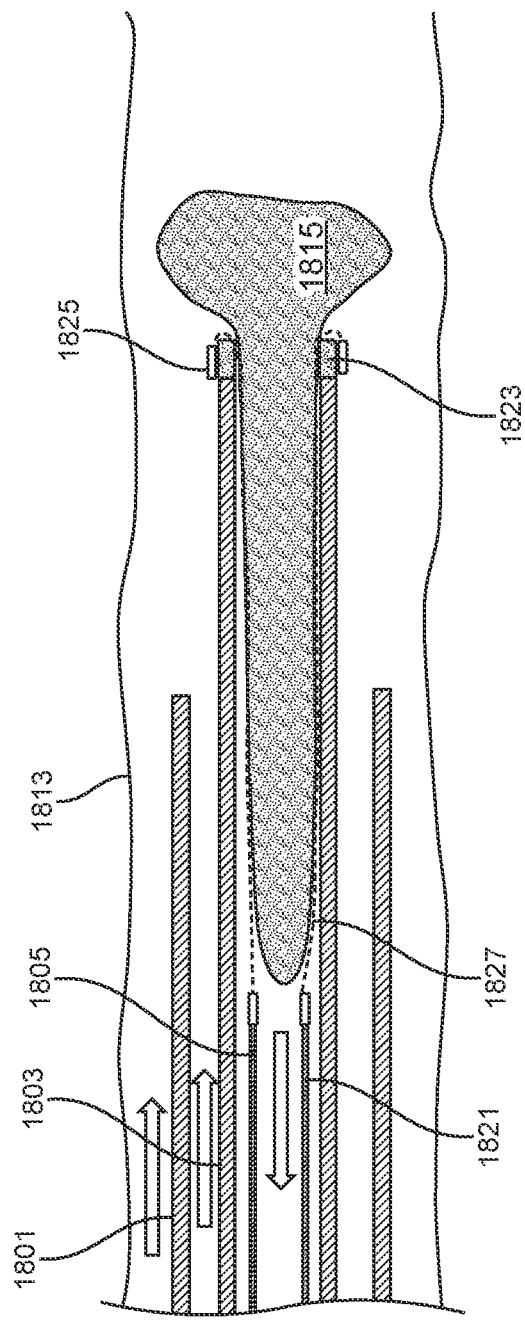
Figure 18I:
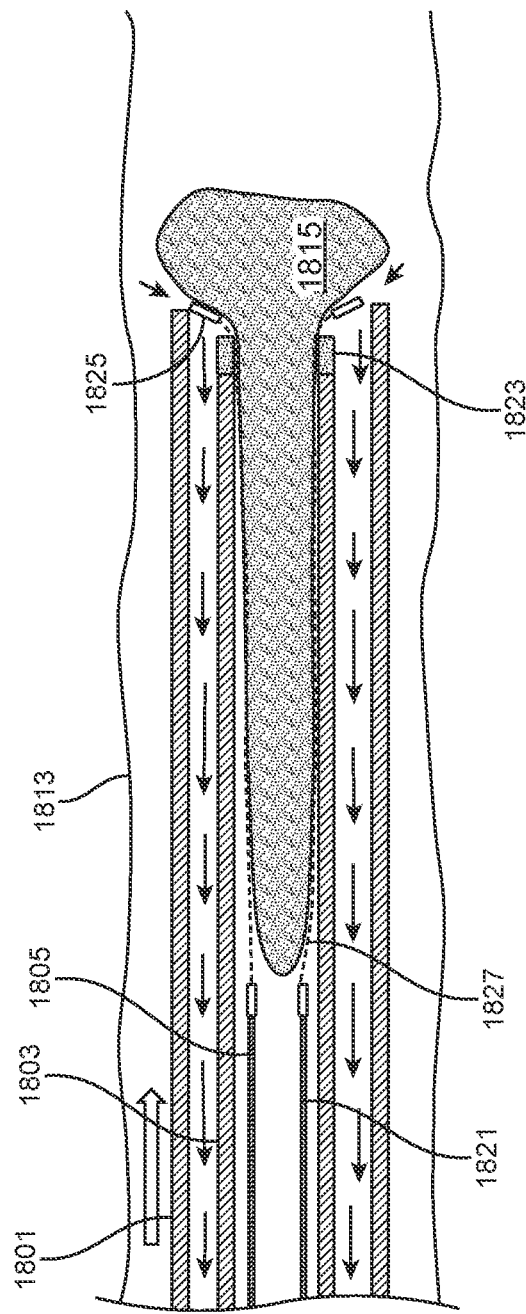
Figure 18J:
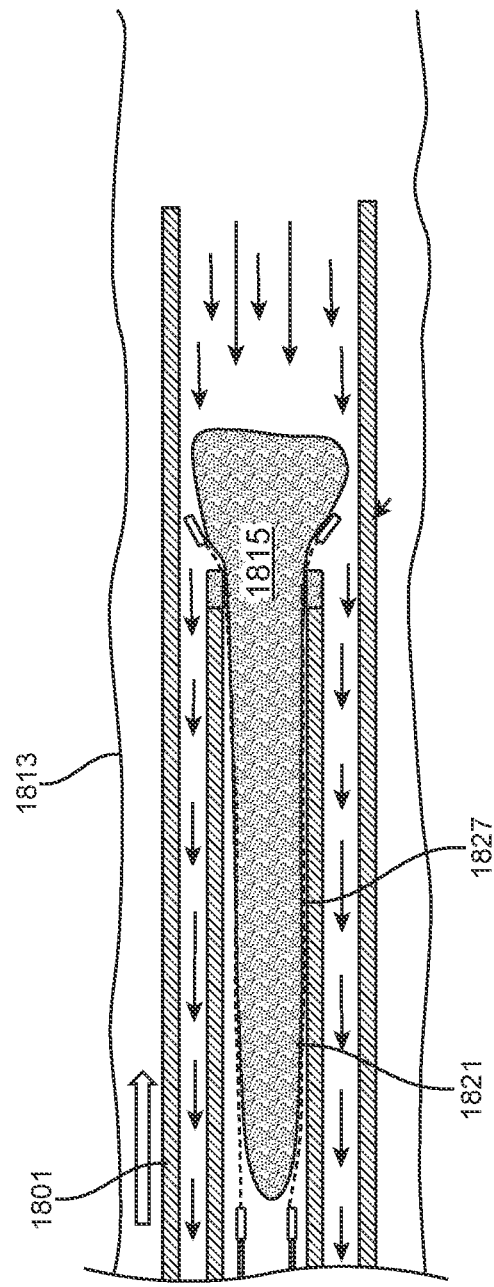

In FIG. 18A-18J the second end of the flexible tube includes a cuff 1825 that may prevent the flexible tube from rolling over the distal end when pulling proximally on the puller, as shown in FIG. 18H. In FIG. 18I, the intermediate catheter is shown advancing distally beyond the cuff and the distal end of the intermediate support catheter. In this configuration (as also described in FIGS. 22A-22B) the motion of the intermediate catheter 1801 may invert the cuff 1825 over the distal end of the inversion support catheter 1803 and against the clot 1815 without breaking or disrupting the clot. A vacuum (suction) may be applied through the intermediate catheter is also shown in FIG. 18I (by the small arrows). In FIG. 18J, the flexible tube, puller and inversion support catheter are then drawn proximally into the intermediate catheter along with the un-engulfed portion of the clot, either by driving the intermediate catheter distally over them, and/or by pulling the inversion support catheter (which may be pulled with the puller) proximally.

Thus, in the example shown in FIGS. 18A-18J, a larger clot, both in diameter and in length, may be removed by the apparatus.

Figure 19:
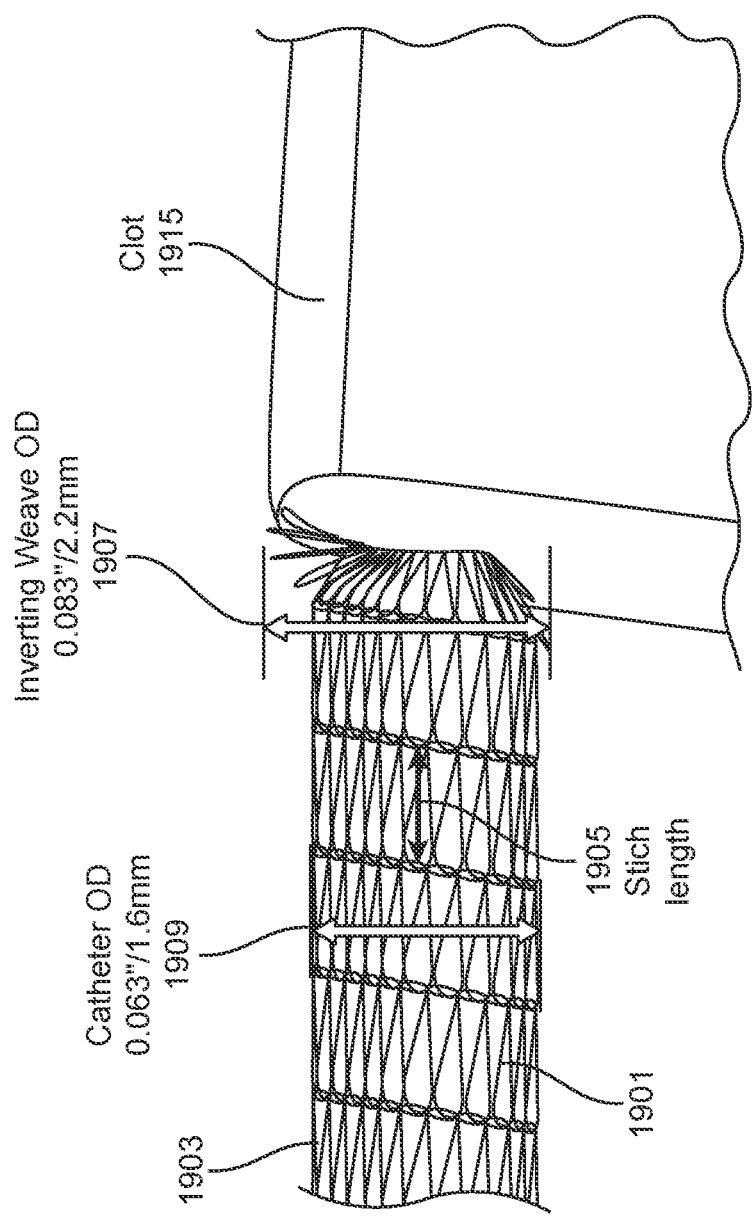
FIG. 19 illustrates an example of a mechanical thrombectomy apparatus having a knitted flexible tube that is configured to operate even in larger-dimeter vessels (having proportionally larger-diameter clots) by configuring the stitch length of the knitted tube to help grab larger-diameter clots.

FIG. 19 illustrates another example of an apparatus that is configured or adapted to have a smaller diameter (outer diameter) than the vessel and the clot but may be capable of grabbing and removing larger clots (e.g., clots having an outer diameter that are more than 1.5×, more than 2×, more than 2.5×, etc.) the outer diameter of the flexible tube capturing the clot.

In FIG. 19, the apparatus includes a flexible tube that is configured as a knit tube. In this example the region of the knit tube 1901 on the outside of the inversion support catheter 1903 hugs the outer diameter (OD) of the inversion support catheter. In order to maximize the ingesting efficiency/power of the knit when used to capture larger clots, the stich length of the knit may be tuned to the diameter of the vessel in which the apparatus is to be used. For example, in general, the stitch length 1905 is the lateral extent of a loop formed by the knit. In general, the outer diameter 1909 of the inversion support catheter may be known, and the inner diameter of the vessel (which may be equivalent to the outer diameter of the clot) may also be known or approximated (e.g. from fluoroscopy). Thus, the user, such as a surgeon or physician, may select the appropriate flexible tube (e.g., knit) based on the selected size. For example, in FIG. 19, twice the knit or stich length (knit/stich length) plus the outer diameter of the inversion support catheter may be approximately equal to the Vessel ID in order to maximize power/efficiency when grabbing and/or removing clot. The woven stitches may act as fingers or extensions that swing around the distal end opening of the inversion support catheter 1907, as shown in FIG. 19. Thus, for vessel inner diameters of between set ranges, the knit/stitch length may be determined. In general, the knitted tube may comprise a filament knitted to form a plurality of interlocking loop stitches, wherein each loop stitch has a stitch length that is between the difference of 25% of the ID and one half the outer diameter (OD) of the inversion support catheter and 65% of the ID and one half of the OD of the inversion support catheter. For example, twice the knit/stitch length plus the inversion support catheter OD may be equal to a range of vessel inner diameters (IDs), such as between about 90%-110% of the vessel ID, between about 80-100% of the vessel ID, between about 60-100% of the vessel ID, between about 50-100% of the Vessel ID, between about 30-100% of the vessel ID, between about 20-100% of the vessel ID, between about 10-100% of the vessel ID, and/or between about 50-130% of the vessel ID.

In practice for most neurovascular and/or peripheral vascular applications, the knit/stitch length may be between about 0.5 mm and about 10 mm (e.g., about 0.5 mm, between about 0.1 to 0.5 mm, about 1. mm, between about 0.5-1. mm, about 1.5 mm, between about 1.-1.5 mm, about 2. mm, between about 1.5-2. mm, about 2.5 mm, between about 2.-2.5 mm, about 3. mm, between about 3.-3.5 mm, between about 0.5 mm-10 mm (e.g., by any 0.5 mm increment), etc.

In general, the apparatuses described herein may compress a clot. For example, FIG. 20A illustrates an example of a clot 2005 shown within the bottle on the top of the figure that is 5 cm long and has an outer diameter of about 15 mm. A portion of an inverting mechanical thrombectomy apparatus is shown in the middle of FIG. 20A, showing an inverting support catheter that is an 8 French (8F) catheter 2003 over which a flexible tube, formed of a knit material 2001, has been arranged, including coupling to one end of a puller (not shown). The flexible (knitted) tube in this example is biased to expand in an uploaded state to an outer diameter than is much greater than the outer diameter of the inverting support catheter. This apparatus was used to remove the clot 2005, which resulted in compressing the clot 2007, as shown in FIG. 20A, bottom.

Figure 20B:
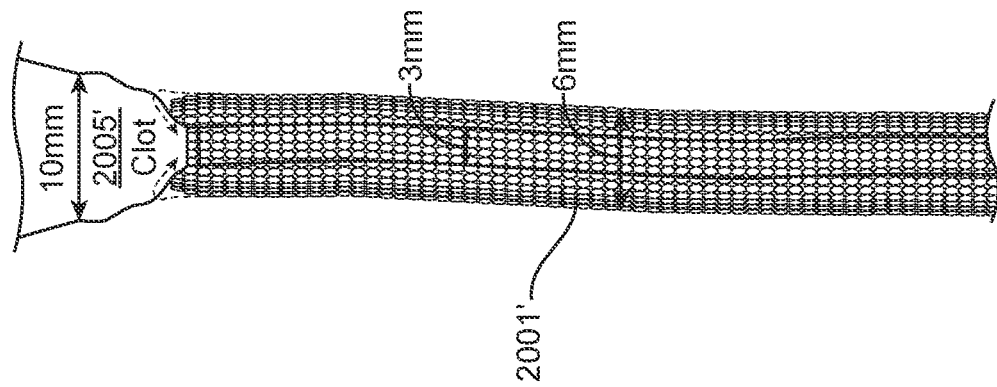
FIG. 20B shows a side view of a distal end region of a similar mechanical thrombectomy apparatus having a knitted flexible tube that inverts into a 3 mm inversion support catheter. The knitted flexible tube has a 6 mm expanded first configuration, but may remove clots having an outer diameter much larger (e.g., a 15 mm outer diameter clot, as shown in FIG. 20A).
Figure 20A:
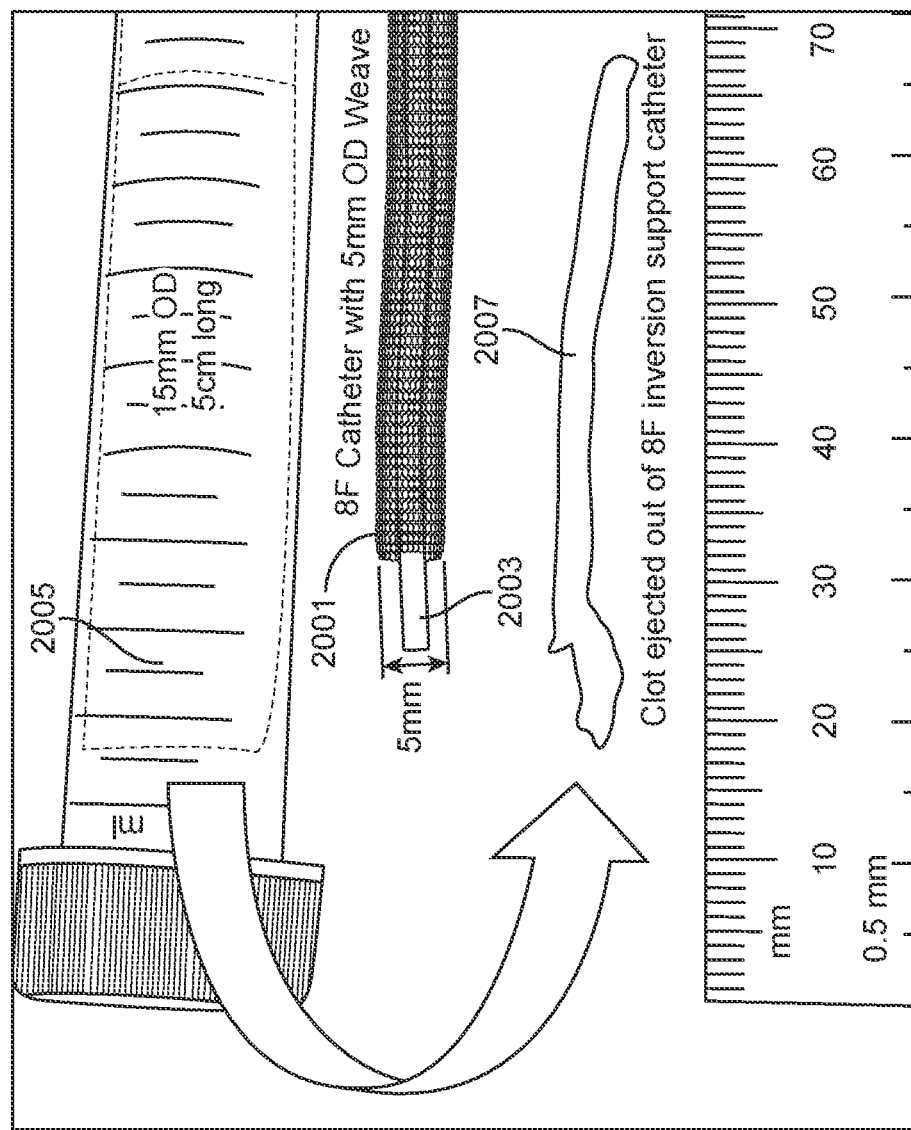
FIG. 20A illustrates a larger-dimeter clot (e.g., shown in the top as a 15 mm OD, 5 cm long clot) that was captured using a narrower-diameter mechanical thrombectomy apparatus having a knitted flexible tube portion (shown having an expanded outer diameter of 5 cm with an 8F inversion support catheter). The removed clot is shown on the bottom above the ruler.

Another example of an apparatus for removing clot is shown in FIG. 20B, showing a 10 mm diameter clot 2005' being grabbed and engulfed by a flexible tube 2001' having an expanded outer diameter of 5 mm extending over a 3 mm outer diameter inversion support catheter.

Figure 21B:
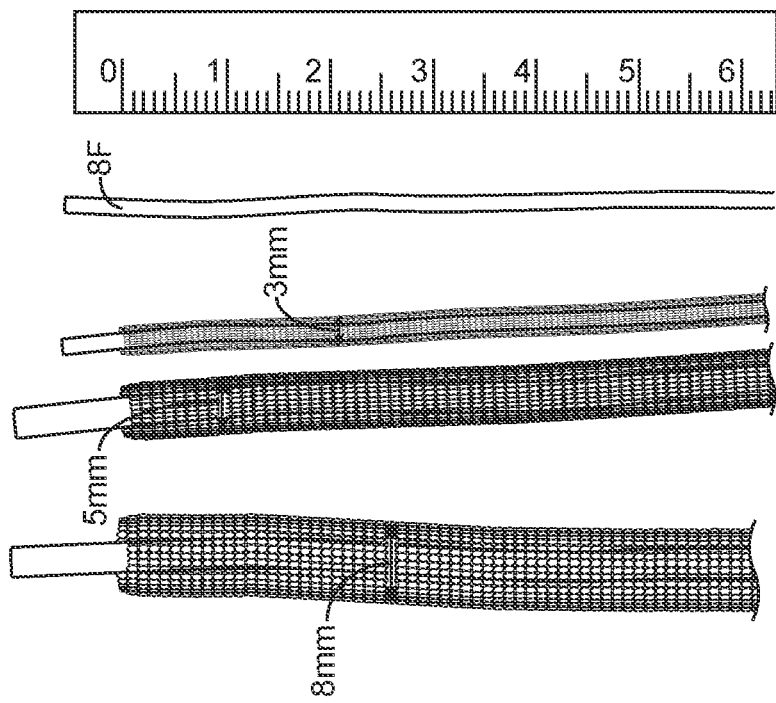
FIG. 21B shows example of the distal ends of mechanical thrombectomy apparatus tested in FIG. 21A, showing variations with 8 mm expanded outer diameter, 5 mm expanded outer diameter, and 3 mm outer diameter, as well as an 8 French (8F) inversion support catheter.
Figure 21A:
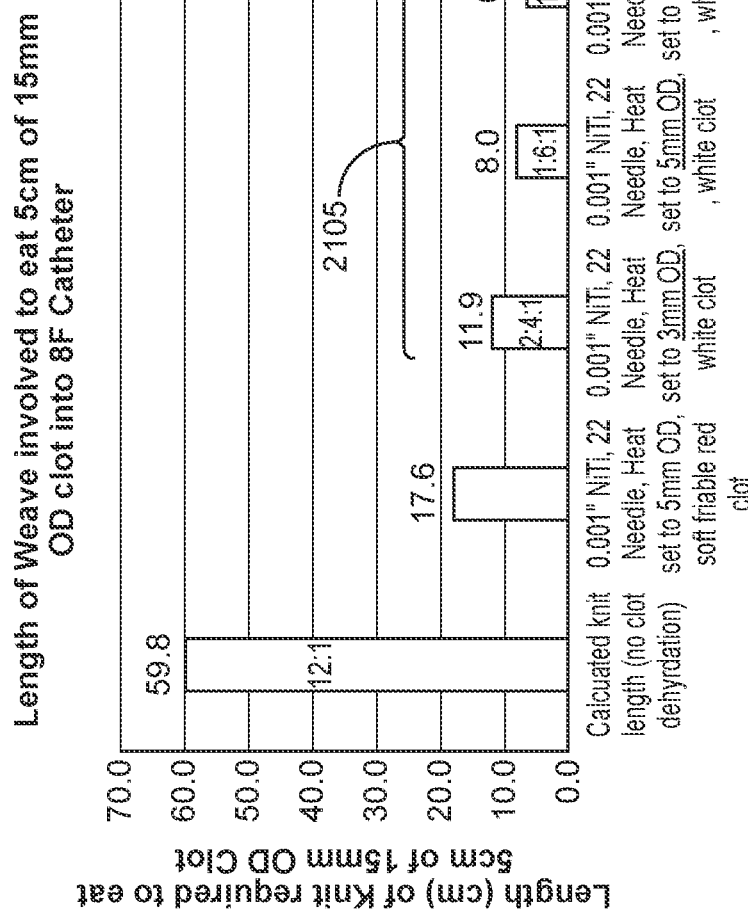
FIG. 21A illustrates and example of a relationship between the length of flexible tube required for a mechanical thrombectomy apparatus as described herein in order to completely engulf ("eat") a clot having an outer diameter of 15 mm and a length of 5 cm. In this example, the flexible tube is a knitted or woven tube formed of heat-set 0.01 inch NiTi wire.

In general, the amount of clot that may be contained (e.g., "eaten") by the rolling and inverting devices described herein in a single pass may be a function of the diameter of the clot, the length of the flexible tube, the structure of the flexible tube (e.g., woven, knitted, etc.) and most importantly, the expanded outer diameter of the flexible tube. For example, FIGS. 21A and 21B illustrate the relationship. In FIG. 21A, the graph shows the length of the flexible tube (e.g., length of the woven tube, L, needed to fully engulf a clot of 15 mm diameter and 5 cm length. In general, the results show that for compressible clots, the length of the flexible tube necessary to fully engulf a 5 cm length of 15 mm diameter clot (depending on the type of clot, including its compressibility) may be between about 6. mm and about 60 mm. Thus, as a rough rule of thumb, as much as a 12:1 ratio of flexible tube to clot may be necessary at this exemplary dimension of a clot. FIG. 21B illustrates example of different apparatuses 2105 used to generate the data shown in FIG. 21A.

In general, the knit expands to a larger diameter than the outer diameter of the catheter once the apparatus is delivered to a clot site when the vessel ID is much larger than the catheter OD. Furthermore, the flexible tube (e.g., knit tube) may expand to a larger diameter than the catheter once it is delivered to clot site, particularly when the vessel ID is much larger than the catheter OD. This is illustrated, e.g., in FIG. 20B. Typically, to maximize the efficiency/power of the flexible tube to ingest a clot, when the catheter is much smaller than the vessel ID/clot OD, it may be helpful to have an expanded outer diameter of the flexible tube such that it is at least 10% (e.g., at least 20%, 30%, 40%, 50%, 60%, 70%, 80%, etc. of the Vessel ID, or any range between any two of these percentages). For example, it may be preferable for the expanded flexible tube to have at least 30% of the vessel ID. Further, as mentioned above, the expanded diameter of the flexible tube may be at least about 30%, 50%, 100%, 150%, 200%, 250%, 300%, 400%, 500%, 600%, etc. of the catheter OD (or any range between any of these two percentages).

As shown in FIG. 19, and discussed above, the extension of the loop stiches in flexible tubes that are knitted (forming "fingers" on the knit, or protrusion that roll and extend beyond the expanded OD of the rest of the flexible tube) may further help grab and remove clot. These extensions for an apparatus such as shown in FIG. 19 (or 26A) may be between about 0.5 mm-10 mm (e.g., between any two value in this range, typically by 0.5 mm increments, including any range between any such increments).

Figure 22A:
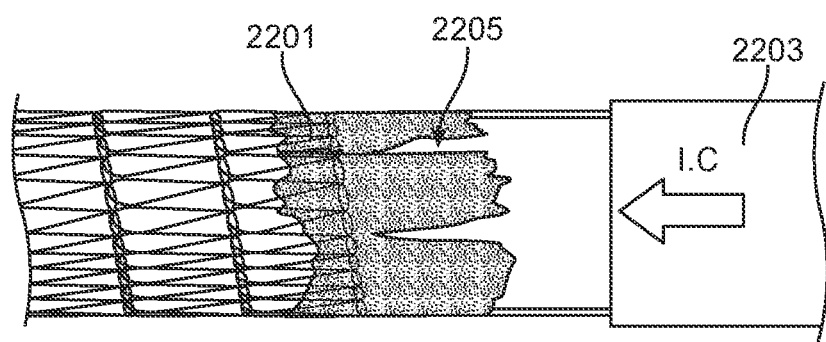
FIG. 22A shows another example of a cuff that may be at the second end of a flexible tube of a mechanical thrombectomy apparatus.
Figure 22B:
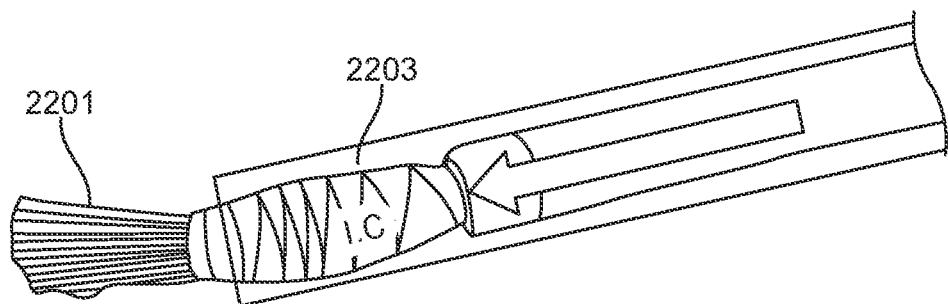

FIGS. 22A and 22B illustrate an example of a cuff as discussed above. In the example shown in FIGS. 22A and 22B, the cuff 2201 is made of (or includes) a radiopaque polymer filling the cuff at the second end of knit tube. This may allow it to be seen under fluoroscopy, and may also prevent unraveling of the knitted tube. In FIG. 22A, the cuff includes a plurality of lateral slits 2205 (e.g., four are shown, though 3, 4, 5, 6, 7 or more slits may be used). These slits may allow the cuff to flip over inversion support catheter, e.g., when driven by an intermediate catheter 2203, as shown in FIG. 22B. In this example, the cuff may be formed of a polymer such (e.g., as Pebax 45D+80% tungsten filled). The cuff may have a wall thickness of less than about 0.025 inches when laminated on knit, and may have a length of between 1 and 3 loop stitches (e.g., about 1.5 knit stitches long).

FIGS. 23A-23B and 24A-24B illustrate examples of a proximal end of a mechanical thrombectomy apparatus, showing components of the apparatus (e.g., guidewire 2305, inner/inversion support catheter 2307, puller 2309, and intermediate catheter 2311. FIG. 23B shows another example, of a proximal end of the mechanical thrombectomy apparatus showing manual controls, including vacuum attachment ports (RHVs) 2317, 2319, for the different regions, as well as the puller hub 2321 at the proximal end.

FIGS. 24A-24B illustrate another example of a set of proximal end controls for a mechanical thrombectomy apparatus. In FIG. 24A the apparatus control region is shown in a first puller position (prior to pulling the clot in), and includes the inner (e.g., puller) rotating hemostat valve (RHV) 2417, outer (intermediate catheter) rotating hemostat valve (RHV) 2419, as well as the puller hub 2421. One or more stop elements 2423, 2423' may be included on the puller to prevent it from pulling and completely inverting the flexible tube over the distal end of the inversion support catheter, as described above; flush ports 2432, 2433 are also shown. In FIG. 24B the apparatus control region is shown after pulling the clot (showing the puller hub extended proximally).

Figure 25:
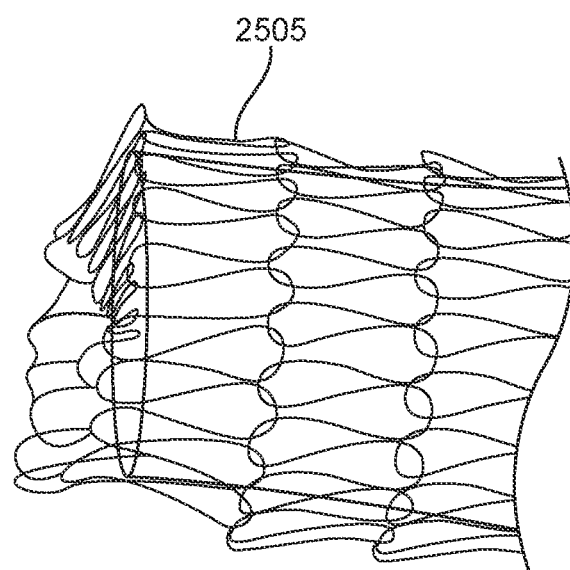
FIG. 25 illustrate an example of a mechanical thrombectomy apparatus in which the flexible tube is configured to cut tissue as it rolls into the inversion support catheter. In this example, the flexible tube is a knitted tube that includes sharp cutting edges that may be used to cut through tissue.

FIG. 25 illustrate an example of a mechanical thrombectomy apparatus in which the flexible tube 2505 is configured to cut tissue as it rolls into the inversion support catheter. In this example, the flexible tube is a knitted tube that includes sharp cutting edges that may be used to cut through tissue. The apparatus may be used over a guidewire to prevent the cutter from dissecting the vessel wall.

Figure 26A:
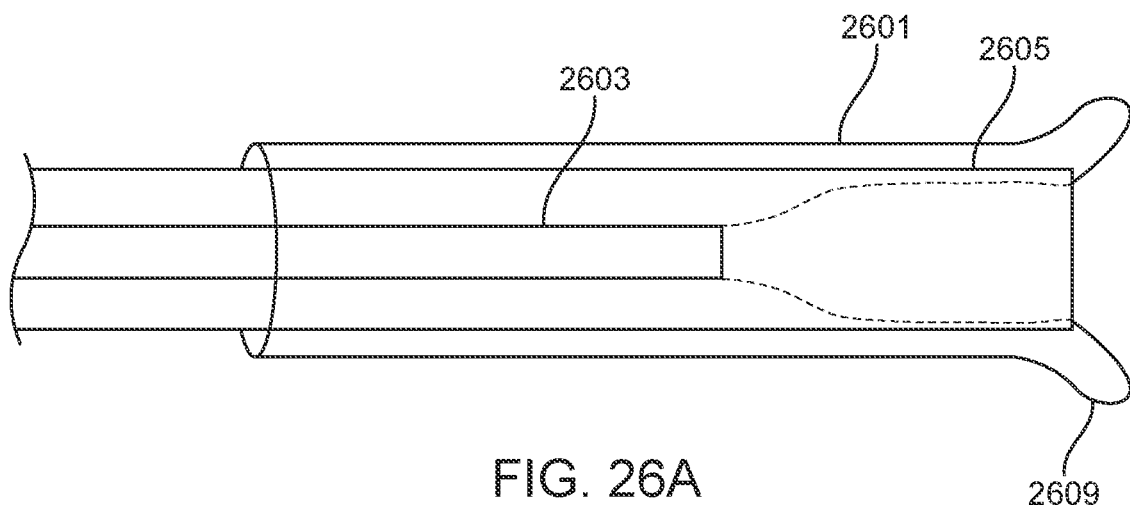
FIGS. 26A-26B illustrate two exemplary side perspective views of mechanical thrombectomy apparatuses.
Figure 26B:
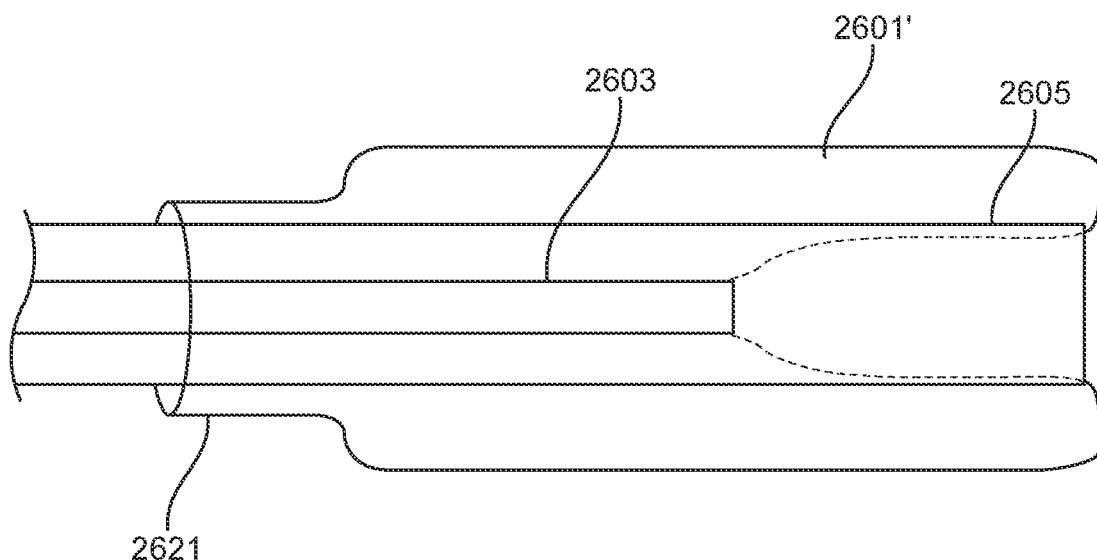

FIGS. 26A-26B illustrate two exemplary side perspective views of mechanical thrombectomy apparatuses. In FIG. 26A, similar to that shown in FIGS. 18A-18J, the apparatus include a flexible (e.g., knitted) tube 2601 that is attached at the first end to a puller catheter 2603 and is configured to expand within the inversion support catheter to an outer diameter that is greater than 40% (shown here as greater than 90%) of the inner diameter of the inversion support catheter 2605, driving the region of the flexible tube within the inversion support catheter against the walls, even when unloaded by clot. The other region (un-inverted) of the flexible tube along the outer diameter of inversion support catheter is shown as snug with the inversion support catheter in the un-constrained configuration. This results in the Y-shaped distal profile 2609, for the inverting flexible tube, which may help grab even larger diameter clots.

FIG. 26B illustrates another example of a mechanical thrombectomy apparatus in which the expanded outer profile of the flexible tube 2601' is expanded beyond the outer diameter of the inversion support catheter 2605 near the first end where it attaches to the puller 2603, but the second end 2621, that is freely sliding over the inversion support catheter, has a much smaller (nearly snug) expanded diameter. This region may also or alternatively include a cuff as described herein.

Re-Sheathing the Tractor

Figure 27A:
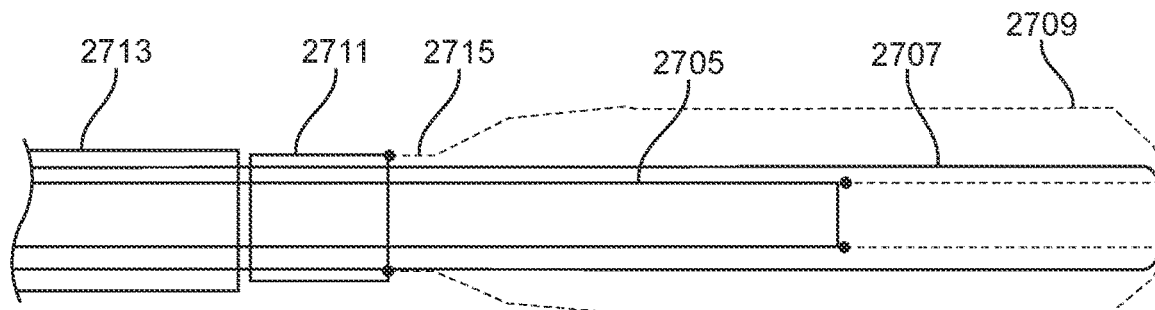
FIGS. 27A-27C illustrate operation of a mechanical thrombectomy apparatus having a cuff on one end of the flexible tube.
Figure 27B:
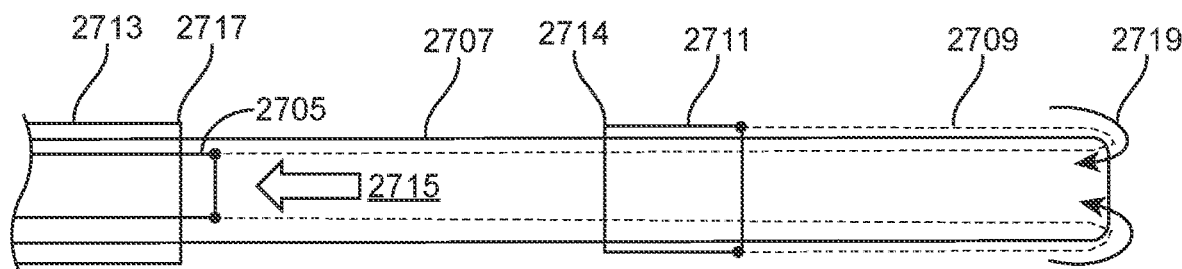
Figure 27C:
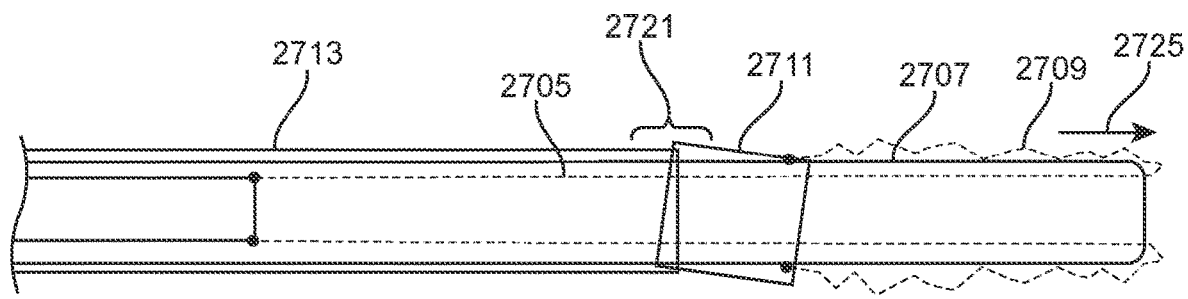

Any of the inverting tube apparatuses described herein may be configured so that the inverting tube apparatus may be retracted (e.g., re-sheathed) into an intermediate catheter. In particular, any of the inverting tube apparatuses that include a cuff at one end (e.g., at the distal end) of the inverting flexible tube may be re-sheathed into the intermediate catheter after deployment, including after capturing all or a portion of a clot. FIGS. 27A-27C illustrates operation of an inverting tube apparatus having a cuff on one end of the flexible tube. As shown in FIG. 27A, the inverting tube apparatus includes an inversion support catheter 2707, a puller 2705 within a lumen of the inversion support catheter, and a flexible tube 2709 extending over the inversion support catheter that is coupled at a first (e.g., proximal) end to the puller, and is configured to roll and invert over the open distal end of the flexible inversion support catheter. In some examples, the flexile tube 2709 may be a woven or knit material. A second end (e.g., distal) end of the flexible tube 2709 may include a cuff 2711 that is less flexible that the region of the flexible tube adjacent 2715 to the cuff. In FIG. 27A, the apparatus is shown in a deployed or partially deployed configuration, in which the flexible tube 2709 and inversion support catheter has been extended out of the distal end of an intermediate catheter 2713, also referred to as a sheath). As discussed above, the apparatus may be delivered to the clot and deployed from out of the intermediate support catheter, including using a guidewire (not shown).

As shown in FIG. 27B, the flexible tube 2709 is configure to be pulled proximally into the inversion support catheter 2707 by pulling 2715 the puller 2705 proximally so that the flexible tube rolls 2719 and inverts over a distal end of the inversion support catheter; the cuff 2711 may slide along the outside surface of the inversion support catheter. As the device is deployed, the distal end 2714 of the cuff 2711 extends further from the distal end 2715 of the intermediate catheter (sheath 2713), which may have a distal end face that faces the deployed cuff 2711, se At any point, either before or after flexible tube has completely, or mostly completely, withdrawn and inverted into the inversion support catheter, the apparatus, and in particular the inversion support catheter, flexible tube, cuff, and any captured clot material, may be withdrawn or re-sheathed back into the intermediate catheter 2713. However, in some cases, including (but not limited to) variations having a cuff 2711 at the second (e.g., distal) end of the flexible and inverting tube 2709 may make it difficult to re-insert the cuff back into the intermediate catheter, as illustrated in FIG. 27C.

In FIG. 27C, the distal face or end 2717 of the intermediate catheter 2713 is shown catching on the distal end 2714 of the cuff 2711 when attempting to re-sheath the sub-assembly including the cuff 2711, flexible tube 2709 and inversion support catheter 2707 back into the intermediate catheter 2713. Although in some variations this may be desirable, as it may help push the cuff and end of the flexible inverting tube off of the end of the inversion support catheter (which it may further envelop and/or cut the clot, as described above in relation to FIGS. 18H-18I), in some variations it may be desired to leave the cuff 2711 on an outside of the inversion support catheter 2707. In this case, as shown in FIG. 27C, if the distal end 2717 of the intermediate catheter 2713 catches on the end face 2714 of the cuff 2711, the cuff may be driven forward, towards the end of the inversion support catheter, as shown. In FIG. 17C, this is shown also driving 2725 the flexible inverting tube 2709 towards the end of the inversion support catheter.

To avoid this, the apparatus may be configured to include one or more cuff retainers that hold the cuff level and/or limit its movement so that it may slide into the intermediate catheter. FIGS. 28A-28C, 29A-29C, 30A-30C, and 312A-31C all describe cuff retainers that may be used.

Figure 28A:
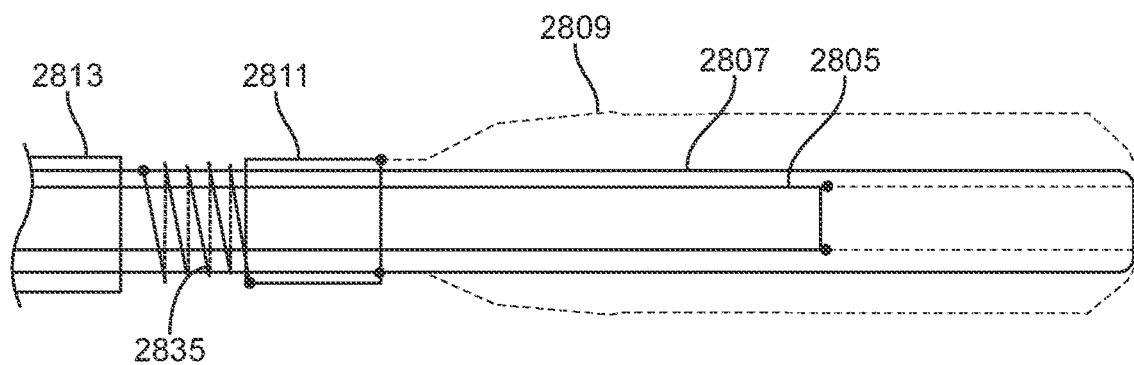
FIGS. 28A-28C illustrate one example of a mechanical thrombectomy apparatus that includes a cuff retainer that may aid in re-sheathing the apparatus into an intermediate catheter.
Figure 28B:
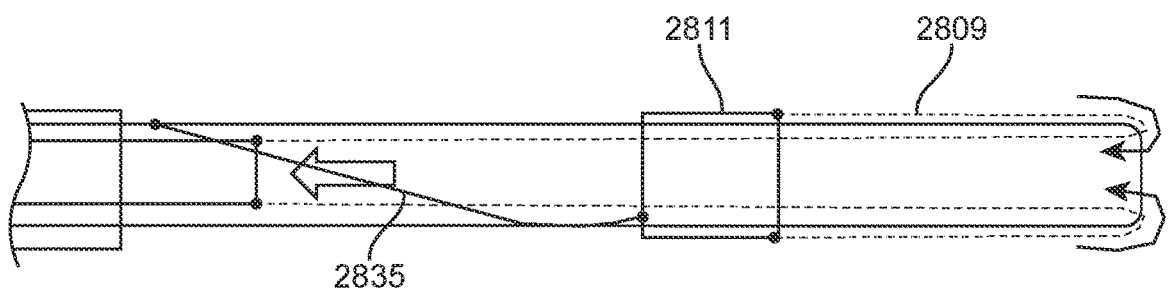
Figure 28C:
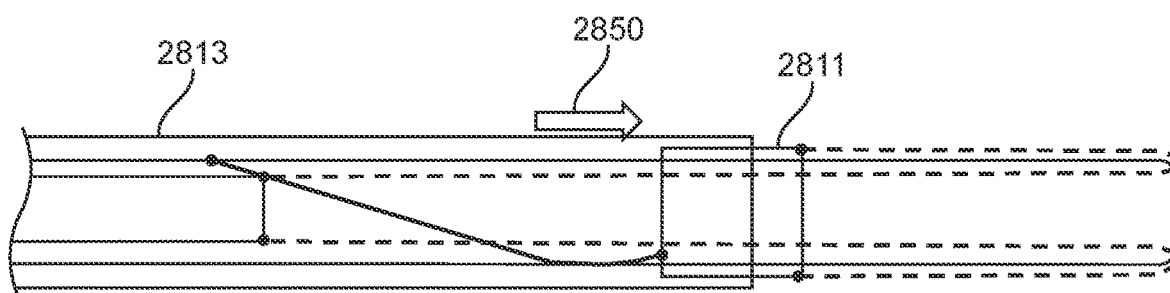

For example, FIGS. 28A-28C illustrate an example of an inverting tube apparatus that includes a cuff at one end of the inverting flexible tube and a cuff retainer, in which the cuff ad flexible tube over the inversion support catheter may be re-sheathed into the intermediate catheter after deployment. The cuff retainer may facilitate the re-sheathing of the cuff and flexible tube into the distal end of the intermediate catheter by applying a force to hold the cuff in a fixed position on the outside of the inversion support catheter. In some variations, the cuff retainer may also or alternatively hold the face of the cuff level relative to the distal end of the intermediate catheter.

In FIG. 28A, the inverting tube apparatuses include a cuff 2811 on the end of an inverting flexible tube 2809 that inverts into the inversion support catheter 2807. A puller (or pusher) 2805 may slide within the inversion support catheter and is attached to the flexible tube 2809. The puller (or pusher) in any of these examples may be a catheter and may pass a guidewire. The cuff retainer in this example is one or more leashes or tether 2835 (e.g., a filament, wire, strand, cable, etc.) that is connected at one or more points on the cuff and one or more locations on the outer surface (or through the outer surface) of the inversion support catheter. The cuff retainer shown is helically arranged over the inversion support catheter so that it may be unwound or unspooled as the puller/pusher pulls and inverts the flexible tube into the inversion support catheter. The cuff retainer may be elastic. In some variations the cuff retainer may include multiple tethers that are spaced circumferentially around the cuff (e.g., spaced equal distances apart).

The inverting flexible tube sub-assembly (cuff, inverting flexible tube, and inversion support catheter) may be re-sheathed into the intermediate catheter 2813 after the puller has pulled the flexible tube into the inversing support catheter, so that the cuff has slid over the inverting support catheter to a predetermined position 2833 towards the distal end of the inversion support catheter, as shown in FIG. 28B.

Once the cuff retainer 2835 is engaged and applying force against the cuff to hold it in position relative to the inversion support catheter, the intermediate catheter 2813 maybe be slid distally 2850 over the distal end of the cuff and/or the sub-assembly including the cuff may be drawn proximally back in to the intermediate catheter. This is illustrated in FIG. 28C.

Figure 29A:
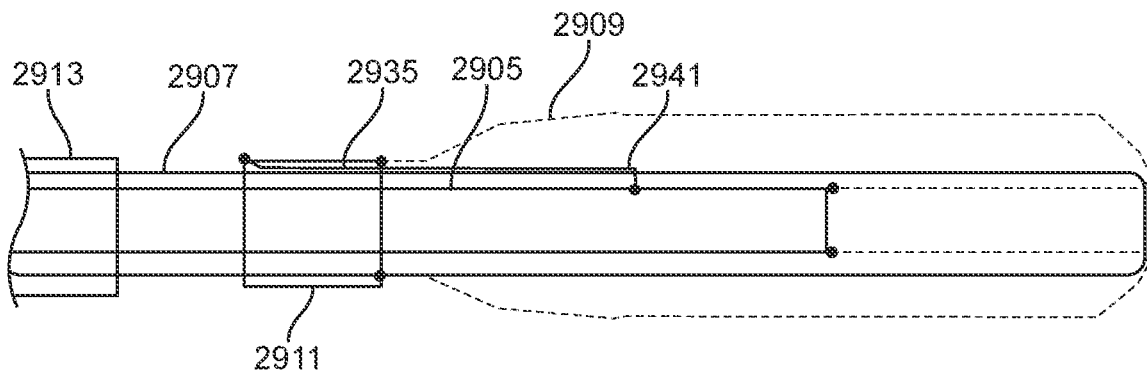
FIGS. 29A-29C illustrate another example of a mechanical thrombectomy apparatus that includes a cuff retainer.
Figure 29B:
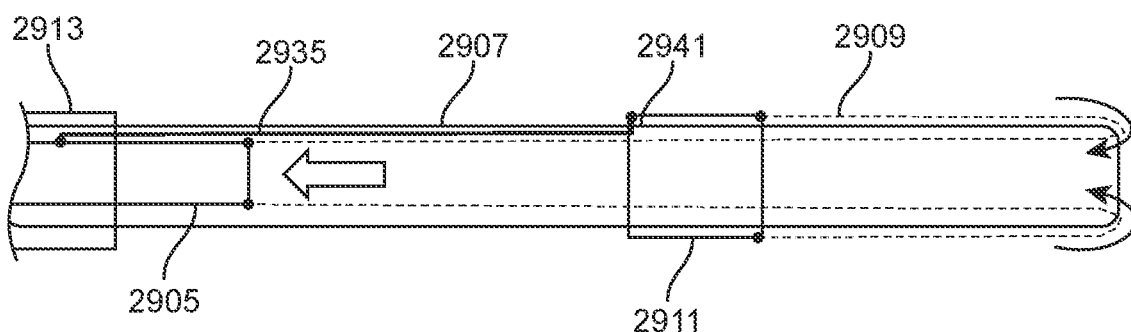
Figure 29C:
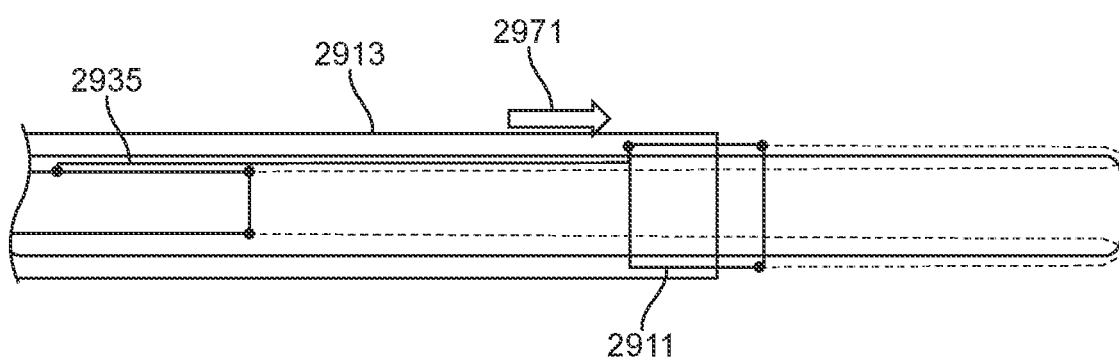

In the variation shown in FIGS. 29A-29C, the cuff retainer 2935 is configured as one or more leashes or tethers 2935 (e.g., filaments, wires, strands, cables, etc.) that is/are attached to a cuff 2911. However, in this example, the cuff retainer passes through an opening 2941 in the inversion support catheter 2907 and attaches to the puller (or pusher) 2905. Thus, as the puller 2905 is drawn proximally to pull and invert the flexible tube 2909 into the inversion support catheter 2905, the cuff retainer 2935 is also drawn with the flexible tube. This configuration may coordinate the movement of the puller with the movement of the cuff, as illustrated in FIGS. 29B and 29C. In FIG. 29B. As shown in FIG. 29B the cuff retainer also limits the axial movement of the cuff along the outside of the inversion support catheter. Thus, by pulling the puller/pusher 2905 proximally, the cuff retainer may apply a force holding the cuff in position so that, as shown in FIG. 29C, the intermediate catheter (sheath 2913) may be advanced distally 2971 and over the cuff and outer portion of the flexible tube 2909. This configuration may also be useful in reloading the flexible tube, as (not shown) force applied to pull the cuff proximally (by pulling/pushing the cuff proximally on the inversion support catheter) may be transmitted to the puller through the cuff retainer (e.g., the one or more filaments, so that force is applied to both ends of the flexible tube to reload the device and also eject any clot within the flexible tube and inversion support catheter.

Figure 30A:
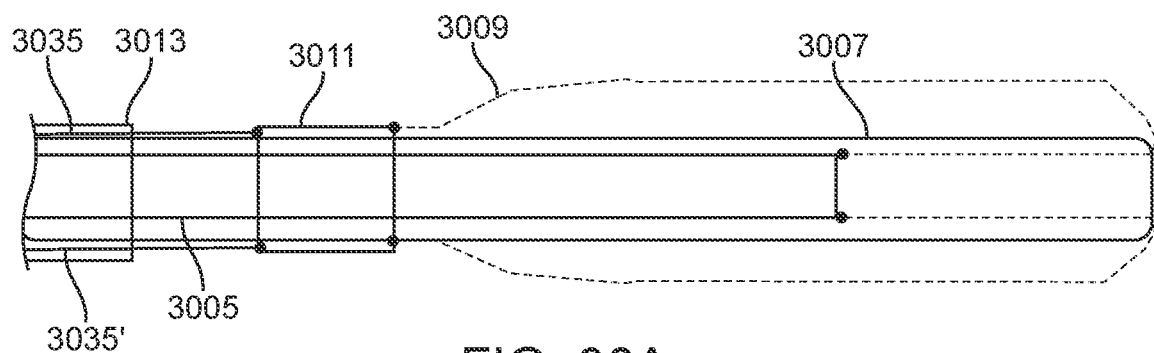
FIGS. 30A-30C illustrate another example of a mechanical thrombectomy apparatus that includes a cuff retainer.
Figure 30B:
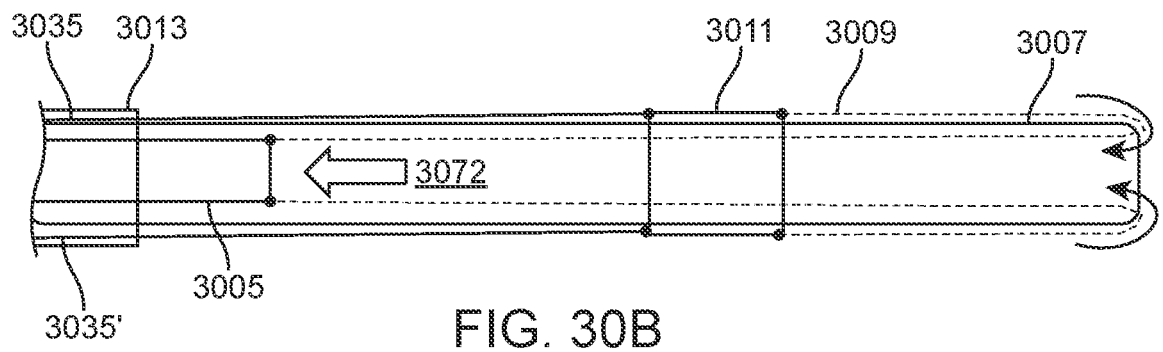
Figure 30C:
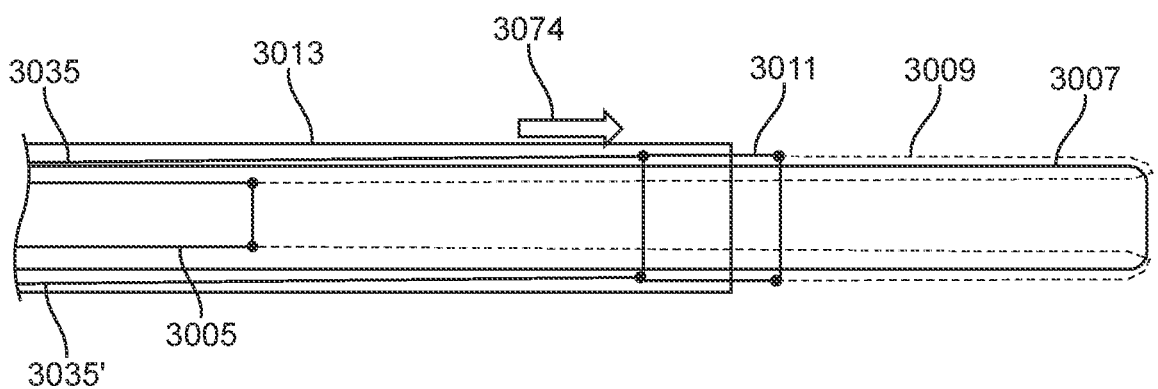

FIGS. 30A-30C illustrate another example of an apparatus including a cuff and a cuff retainer 3035, 3035' in which the cuff retainer includes a pair of leashes or tethers 3035, 3035' (e.g., filaments, wires, strands, cables, etc.) that are attached to the cuff 3011 and extend proximally through the intermediate catheter 3013 all the way to a proximal end of the device where they may be used to apply force (e.g., tension) to the cuff. In FIG. 30B, the puller 3005 has been withdrawn proximally 3072 to cause the flexible tube 3009 (attached to the puller) to roll and invert over the distal end of the inversion support tube 3007. By securing and/or pulling on the cuff retainer 3035, 3035', and in some variations also securing and/or pulling on the puller 3005, the cuff may be held in a fixed location while the intermediate catheter 3013 is driven distally 3074, as shown in FIG. 30C. In this example, the cuff retainer (e.g., tethers) may be made of a metallic (e.g., stainless steel, elgiloy, Nitinol, etc.) or polymeric material. As mentioned, in use, the cuff retainer may be locked down or free to move (e.g., slide) and may be manipulated by the user near the hub of the inversion support catheter or elsewhere on the proximal end of the apparatus.

In some variations, the cuff retainer may be used to pull back the tractor to eject clot after use. For example, the apparatus (e.g., the sup-portion including the cuff, the flexible tube and the puller) may be reloaded on the inversion support catheter and/or material such as a clot captured in the apparatus may be ejected by pulling the cuff proximally (and in some variations pushing the puller/pusher 3005 distally).

Although the cuff retainer shown in FIGS. 30A-30C is shown as one or more tethers, in some examples, the cuff retainer is a tubular structure, which may be knitted, woven, solid, etc.

Figure 31A:
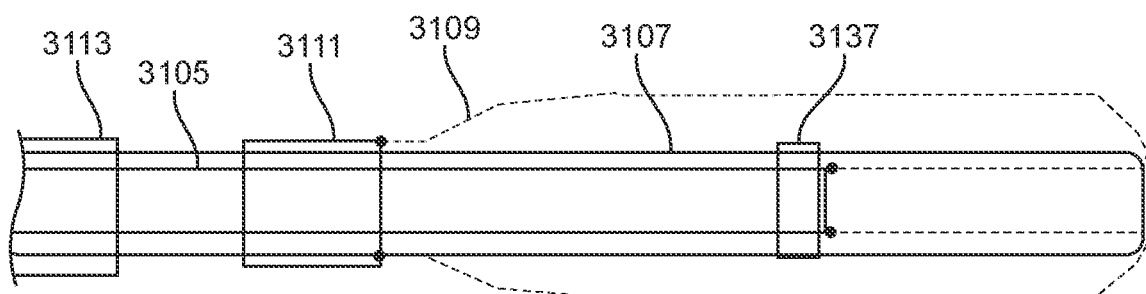
FIGS. 31A-31C illustrate another example of a mechanical thrombectomy apparatus that includes a cuff retainer (configured as a stop).
Figure 31B:
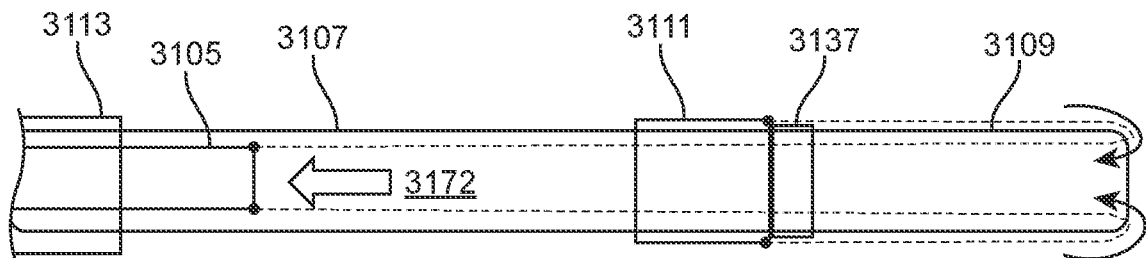
Figure 31C:
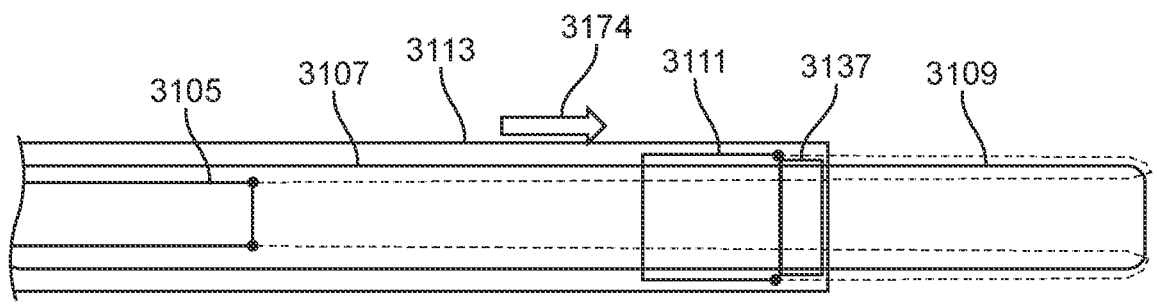

In some variations the cuff retainer is a cuff stop near or on a distal region of the inversion support catheter. For example, in FIG. 31A the cuff retainer is configured as a cuff stop that is formed as a collar attached to the distal end region of the inversion support catheter. In FIG. 31A, the cuff 3111 connected to an end of the flexible tube 3109 slides freely along the inversion support catheter 3105, so that when the puller/pusher 3105 within the inversion support catheter is drawn proximally 3172 (a shown in FIG. 31B), the cuff may be pulled distally while the flexible tube rolls and inverts over the distal end of the inversion support catheter. In FIG. 31B, the cuff is stopped from moving distally by the cuff retainer 3137 (cuff stop). The intermediate catheter (sheath 3113) may then be moved distally over the cuff and any portion of the flexible tube 3109 that is external to the inversion support catheter to re-sheath the apparatus, as shown in FIG. 31C. Alternatively, or additionally, the inversion support catheter, cuff, flexible tube and puller may be drawn proximally into the intermediate catheter. In some variations, a combination of both movements may be used. The puller may be pulled or held so that the cuff is held against the cuff retainer while re-sheathing or alternatively the intermediate catheter (sheath) may drive the cuff against the cuff retainer.

In FIG. 31C the cuff retainer is a stop that is fixed to the outside of the inversion support catheter. Any stop that may engage with the outer distal-facing edge of the cuff and the inversion support catheter may be used. For example, the cuff retainer may be a cuff stop that is a bump, ridge, button, protrusion, band, ring, lip, or the like. One or more (e.g., two, three, etc.) discrete regions arranged around the outside of the inversion support catheter may be used. The cuff retainer may made of any appropriate material, e.g., a polymer or metallic structure, and may be a solid element or a braid or knit structure.

In addition to these mechanical cuff retainers (cuff stops), electrical and/or magnetic cuff retainers may be used. For example, the cuff retainer may be a magnetic or paramagnetic material that interacts with cuff (which may include a magnetic or parametric material) to limit movement of the cuff distally.

Any of the cuffs described herein may also include one or more tapered or shaped ends that also help re-sheath the apparatus. For example, in some variations, the proximal end of the cuff may be tapered towards the inversion support catheter.

Figure 32A:
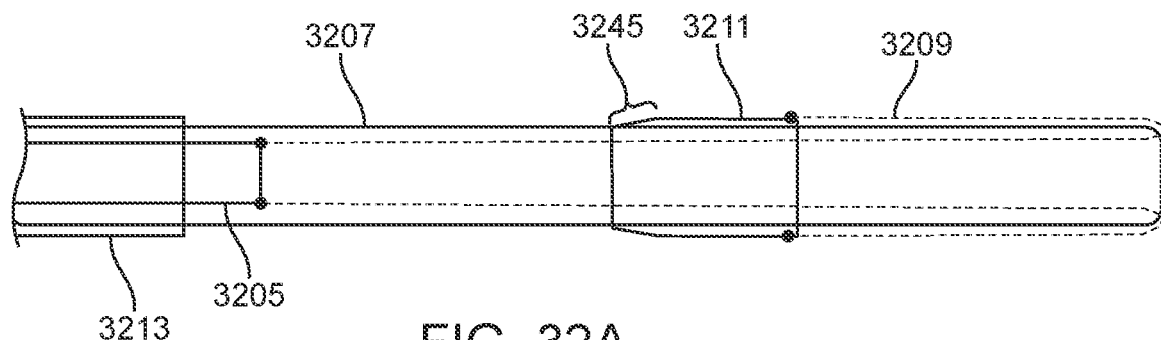
FIGS. 32A-32F illustrate examples of mechanical thrombectomy apparatus including a cuff that is adapted at the proximal-facing end to aid in re-sheathing into an intermediate catheter.
Figure 32B:
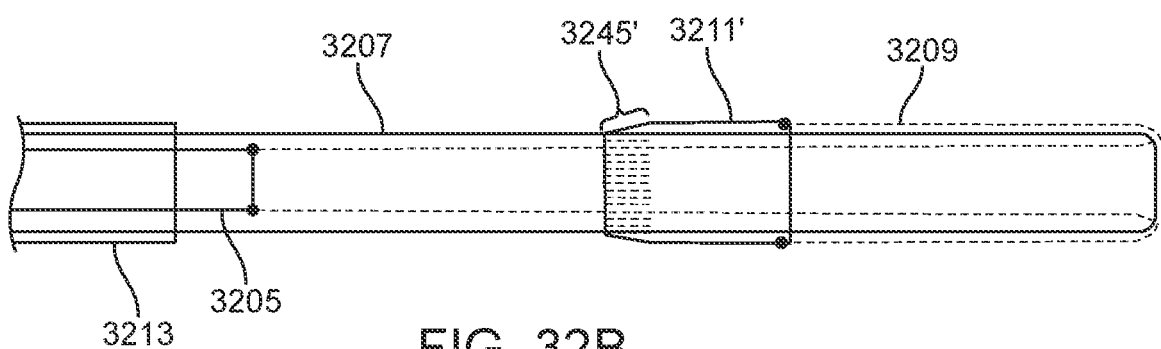
Figure 32C:
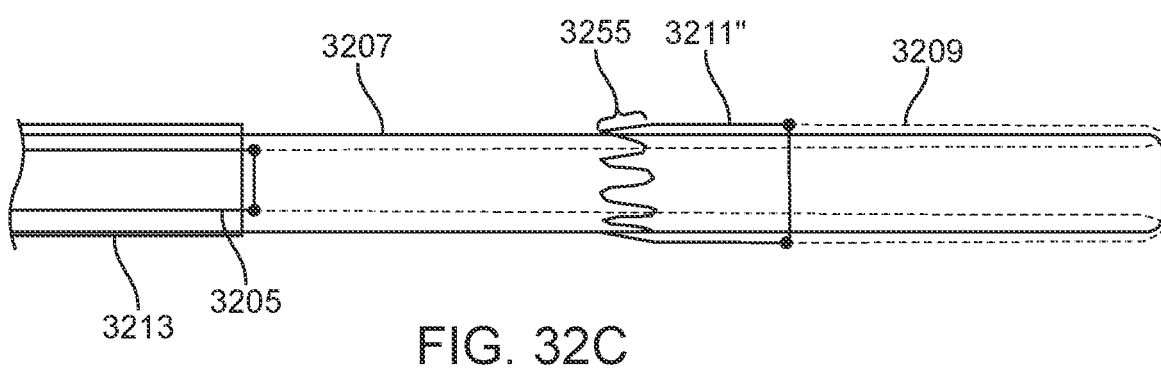

FIGS. 32A-32C illustrate examples of tapered cuffs that may be used. In FIG. 32A, the apparatus includes a cuff 3211 that has a skived or tapered proximal end 3242. The cuff is attached at the other end to the flexible tube 3209 which inverts and rolls over the inversion support catheter 3207 when pulled by the puller 3205 from within the inversion support catheter. The sub-assembly including the inversion support catheter, flexible (inverting) tube, and the cuff is shown in a deployed configuration extending from outside of the intermediate catheter 3213. The tapered cuff may aid in re-sheathing the sub-assembly, including the cuff, back into the intermediate catheter. A tapered cuff may be used with or without a cuff retainer, including any of those described above.

FIG. 32B is another example of a tapered cuff 3211 that includes a proximal tapered region 3245'. In this example, the tapered region includes serrations that may allow some flexibility of the narrowed proximal end so that it is still free to slide on the inversion support catheter. The serrations may be configured as one or more slots, slits or cut-out regions in the tapered region. The serrations may be limited to the tapered region.

FIG. 32C is another example of a tapered cuff 3211 having a crown-like tapered region 3255 comprising a number of larger cut-out regions, similar to the serrations of the tapered region in FIG. 22B. In FIG. 32C the tapered region may include tapered fingers or projections that may be triangular, square/rectangular, curved and/or sinuous and/or irregularly shaped tapered extensions. In some variations, the tapered region is crenelated.

The tapered regions of the cuff may extend over a portion of the cuff, e.g., between 5%-50% of the length of the cuff in the long-axis of the inversion support catheter (e.g., between 10% and 50%, between 15% and 50%, between 10% and 40%, etc.). The cuff may be any appropriate length, e.g., between 0.5 mm and 30 mm, between 1 mm and 20 mm, between 2 mm and 20 mm, greater than 2 mm, greater than 3 mm, greater than 4 mm, greater than 5 mm, greater than 6 mm, etc.).

Figure 32D:
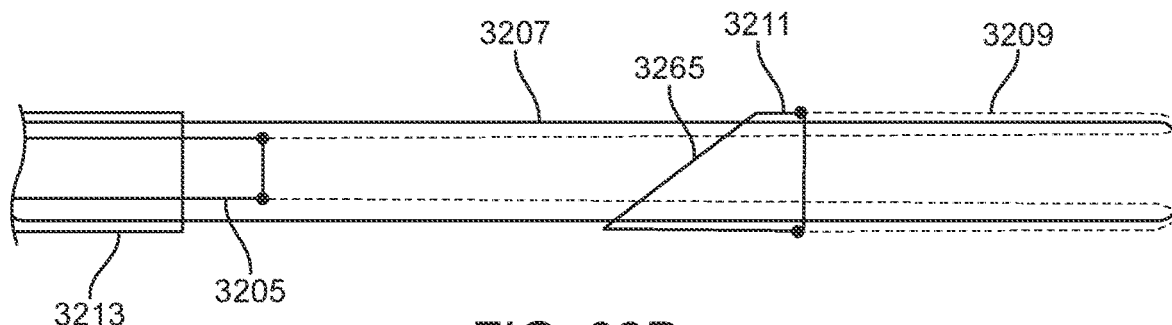
Figure 32E:
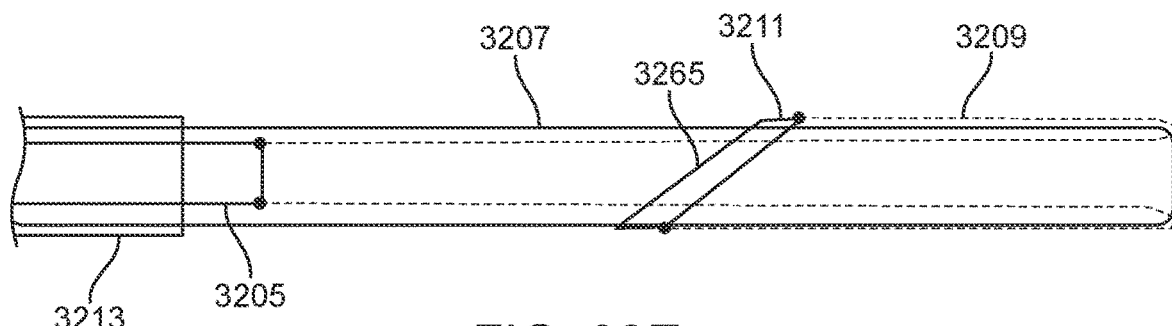

FIGS. 32D and 32E illustrate cuffs having tapered regions that are angled on the proximal-facing sides. Thus, the proximal-facing side of the cuff is angled relative to the body of the cuff and the inversion support catheter. In FIG. 32D the cuff 3211 has an angled proximal side 3265, but the distal-facing side of the cuff is flat (e.g., perpendicular to the long axis of the inversion support catheter over which it may slide. FIG. 32E shows a cuff 3211'''' that is similar to the variation shown in FIG. 32D but is also angled on the distal-facing side. The angled proximal-facing side may be tapered (and/or may include tapered cut-out regions/perforations). Cuffs having angled proximal faces may also be used with a cuff retainer. The angled proximal face may be formed by cutting the cuff at an angle. Any appropriate angle may be used, e.g., between 5 degrees and 60 degrees (e.g., between 10 degrees and 50 degrees, between 15 degrees and 45 degrees, etc.), measured as the acute angle formed between the proximal-facing side and the sidewall of the cuff.

Figure 32F:
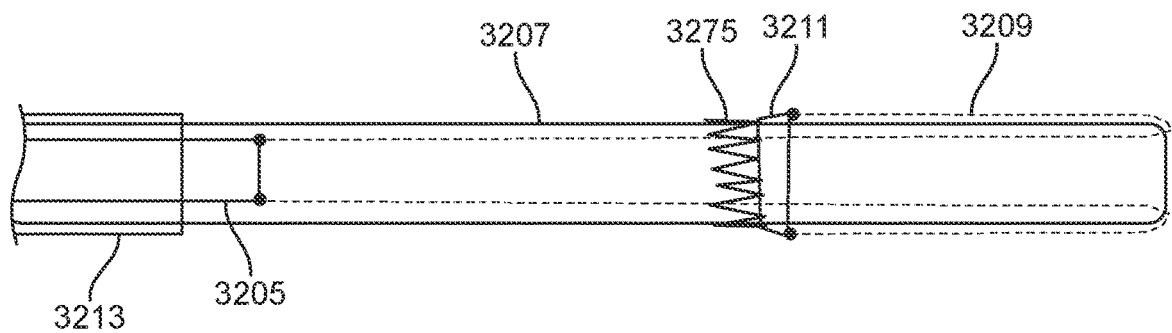

FIG. 32F illustrates a cuff 3211 having a proximal-facing stent like structure 3275 that is low-profile and may also help with re-sheathing. Any of the tapered and/or angled cuffs may also include a proximally-extending stent-like structure. The stent-like structure may include wires, filaments, ribbons, etc. extending from the proximal edge. These sent-like structures may be flattened toward the inversion support catheter 3207 outer surface. A stent-like structure may also be referred to as a low-profile scaffolding, and may extend completely or partially around the perimeter of the cuff.

Any of the apparatuses described herein may also be configured to be re-loadable. For example, FIGS. 33A-33D illustrate one example of a re-loading apparatus in which a single-use subassembly including a cuff 3311 (configured as a split cuff), a flexible tube 3309, and an inner puller 3305, is loaded onto the inversion support catheter 3307, and partially deployed out of the intermediate catheter (sheath 3313). The sub-assembly, which may be referred to as an inverting flexible tube sub-assembly is removable from the inversion support catheter, and may be removed from the inversion support catheter out of the intermediate catheter after removing all or part of a clot; the intermediate catheter (sheath) may then be left in place while the intermediate catheter and inverting flexible tube sub-assembly may be removed from the vessel proximally. Once withdrawn, the sub-assembly may be removed from the inversion support catheter and a new sub-assembly may be loaded onto the inversion support catheter and inserted back through the intermediate catheter to remove additional clot material. This is illustrated in FIGS. 33A-33E.

Figure 33A:
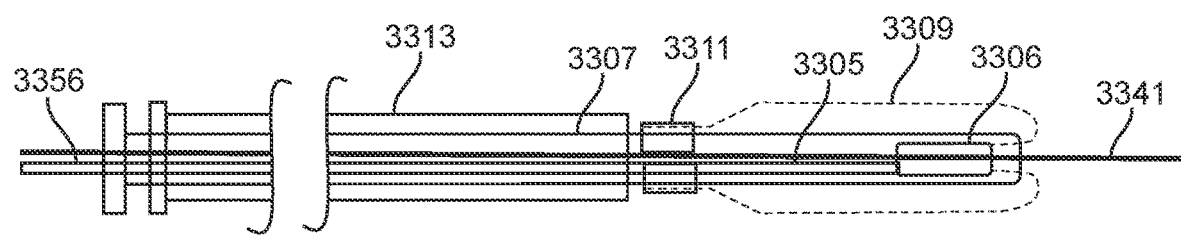
FIGS. 33A-33E illustrate one example of a re-loading mechanical thrombectomy apparatus in which a single-use sub-assembly (including the puller, cuff and flexible tube) can be withdrawn and a new sub-assembly inserted.
Figure 33B:
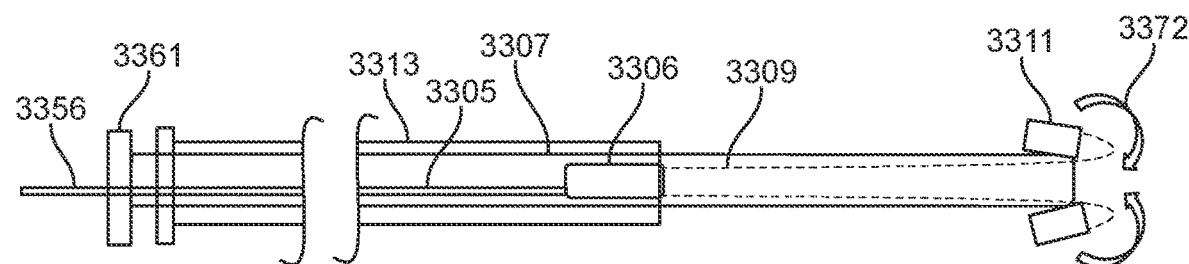
Figure 33C:
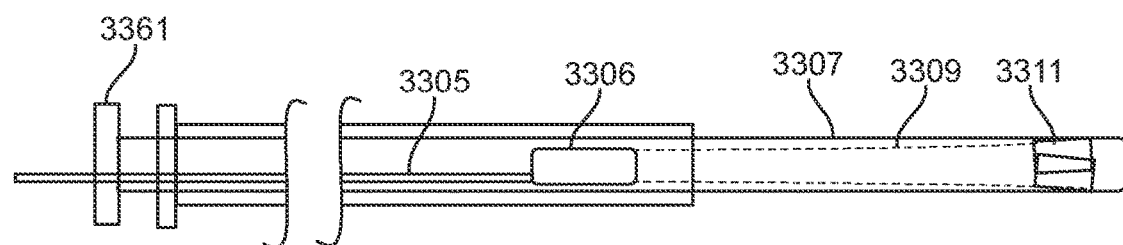

In FIG. 33A, the apparatus is shown partially deployed, with the inversion support catheter 3307 extending out of the sheath 3313, and the flexible tube 3309 connected at one end to a split cuff 3311 and at the other end to a puller (e.g., puller assembly, including a puller wire 3305 and a puller catheter segment 3306). The cuff may be slid over the inversion support catheter distally as the puller is drawn proximally (e.g., by pulling on the puller end 3356). Pulling the puller proximally causes the flexible tube to roll and invert over the distal end of the inversion support catheter. In FIG. 33A, a guidewire 3341 may be used, and passes through the catheter segment 3306 of the puller. As described in greater detail above, this may draw a clot into the inversion support catheter. Once the cuff reaches the distal end of the inversion support catheter, as shown in FIG. 33B, the cuff may split apparat and roll and invert 3372 over the distal end of the inversion support catheter as well, into the inversion support catheter. As shown in FIG. 33C, the entire sub-assembly (e.g., the puller, flexible tube 3309 and split cuff 3311 may then be housed within the inversion support catheter 3307, and withdrawn proximally out of the sheath 3313. For example, the proximal end of the inversion support catheter may include a handle or grip 3361, allowing it to be advanced and/or withdrawn from outside of the patient. The entire sub-assembly and/or inversion support catheter may be removed proximally out of the patient.

Figure 33D:
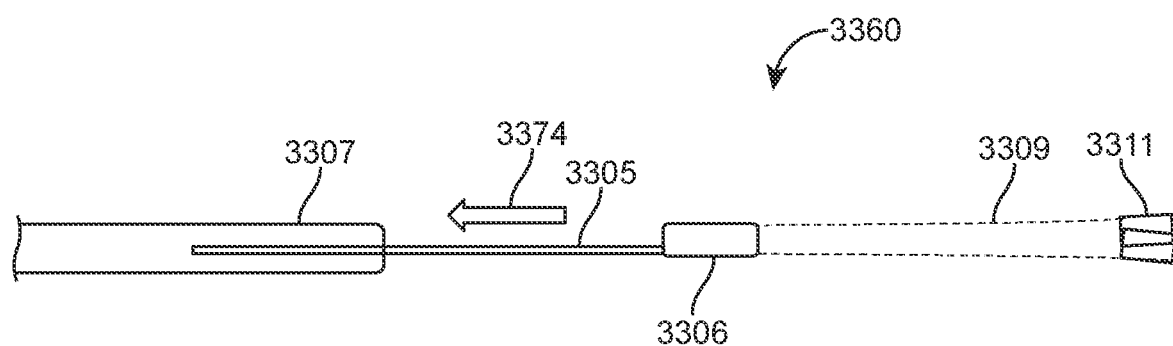
Figure 33E:
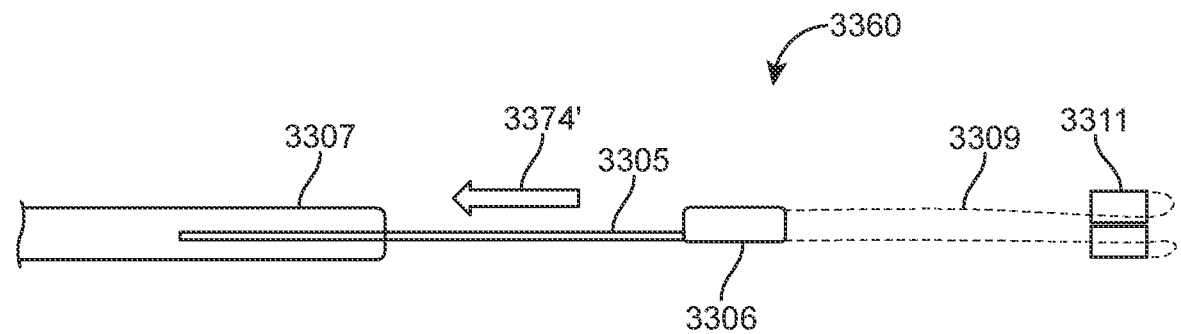

Once removed, the inverting flexible tube sub-assembly may then be removed, along with captured clot, from the inversion support catheter, and either a new inversion support-catheter pre-loaded with an inverting flexible tube sub-assembly may then be inserted into the sheath and back into the vessel to capture any additional clot material, or the same inversion support catheter may be re-loaded with a new inverting flexible tube sub-assembly, as shown in FIG. 33D and alternative variation in FIG. 33E.

In FIG. 33D, a new inverting flexible tube sub-assembly 3360, including the puller (puller assembly including pull wire 3305 and pull catheter 3306), flexible tube 3309 and cuff 3311, is loaded 3374 into the distal end of the inversion support catheter 3307. The variation shown in FIG. 33E is similar to that shown in FIG. 33D, but the cuff 3311' is un-inverted, and therefore loads on the outer surface of the inversion support catheter. As the loaded inversion support catheter is driven back through the sheath, the flexible tube 3309 and cuff may be driven proximally, so that it prepared to be withdrawn proximally by the puller to capture clot by the time it reaches the distal end region of the sheath.

In any of these variations, a guidewire may be use to insert and guide insertion of the inverting flexible tube sub-assembly and/or inversion support catheter to the clot material.

The steps of capturing clot, withdrawing the sub-assembly proximally and reloading anew sub-assembly, as illustrated in FIGS. 33A-33E, may be repeated as necessary to remove more clot material.

Alternatively, as mentioned above, any of the apparatuses described herein may be configured to reusing inverting flexible tube sub-assembly and other portions of the apparatus. For example, the apparatus may be deployed to a clot, and used to remove at least a portion of the clot, and the clot, captured by the flexible tube, may be withdrawn out of the vessel, and ejected from the flexible tube, and the flexible tube (e.g., the inverting flexible tube sub-assembly including the flexible tube) reloaded, reinserted and used to remove additional clot. An example of this is illustrated in FIGS. 34A-34C.

Figure 34A:
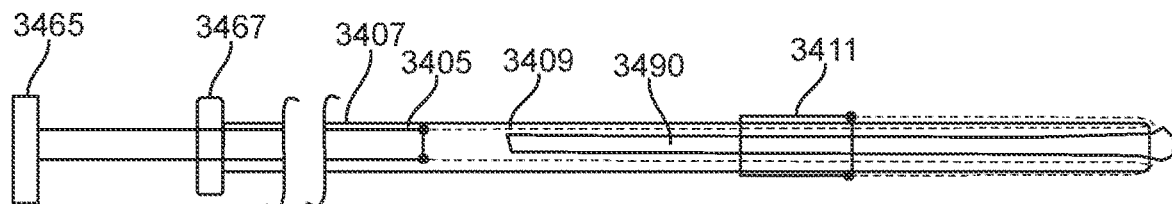
FIGS. 34A-34C illustrate operation of a re-usable/reloadable mechanical thrombectomy apparatus.
Figure 34B:
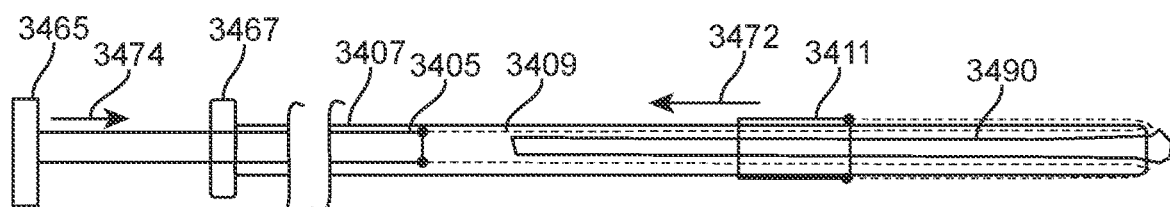
Figure 35:
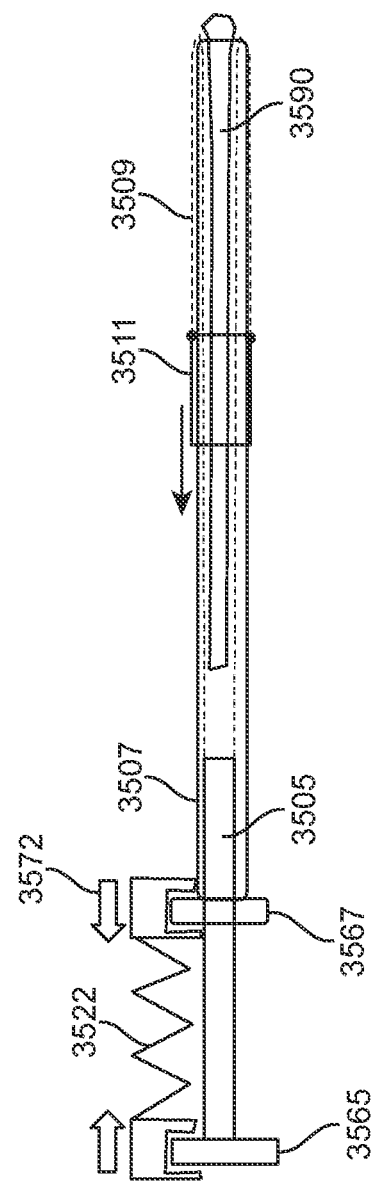
FIG. 35 schematically illustrates one example of an ejection apparatus that may be used to assist in ejecting captured clot material and/or reloading of a mechanical thrombectomy apparatus.

In FIG. 34A, a portion of clot 3490 has been captured by an apparatus. The apparatus may include an inversion support catheter 3407, a puller 3405, a flexible tube 3409 and a cuff 3411. In this example, the puller includes a proximal handle region 3465 and the inversion support catheter includes a proximal handle region 3467. The apparatus has been withdrawn from out of the patient after grabbing the clot material in FIG. 34A. The clot material may then be ejected from the apparatus, as shown in FIG. 34B. In this example, the clot material is ejected by pulling the cuff proximally 3472 and/or by pushing the puller distally 3474. In some variations, the clot may be ejected by both pushing the puller distally and by pulling the cuff proximally. For example, in some variations it may be beneficial to use an ejection apparatus 3522, as shown schematically in FIG. 35, to coordinate the relative motion of the puller 3505 (or puller assembly) and the inversion support catheter 3507, while drawing the cuff 3511 proximally. The ejection apparatus 3522 couples to both the puller proximal handle 3565 and the inversion support catheter proximal handle 3567 and moves the two handles 3565 and 3567 closer to each other 3572, as shown by the arrows. Force may also be provided (manually or automatically) to move the cuff 3511 proximally to eject the clot material 3590 from the flexible tube 3509. For example, the ejection apparatus may be a mechanical apparatus including one or more springs (e.g., extension springs) to assist in ejecting the clot material.

Figure 34C:
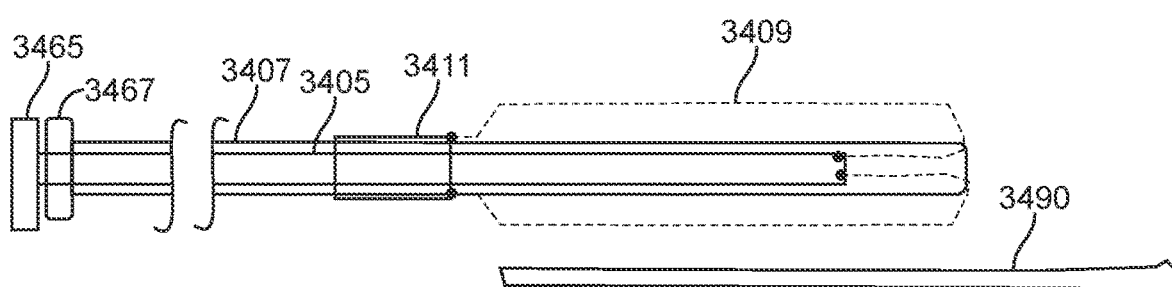

Once the clot is ejected, as shown in FIG. 34C, the apparatus is prepared for re-insertion, and may be inserted back into the patient (e.g., through an intermediate catheter with or without a guidewire) to remove additional clot material. An additional cover or sheath may be used to re-introduce the apparatus through the intermediate catheter.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points.

For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An inverting tube apparatus, comprising:
    an inversion support catheter;
    a puller at least partially disposed within a lumen of the inversion support catheter; and
    a knitted flexible tube extending over a distal end of the inversion support catheter in a compressed state, the knitted flexible tube having a plurality of interlocking loops, a first end coupled to a distal end region of the puller, and a second end disposed on an outer surface of the inversion support catheter,
    wherein the knitted flexible tube extends distally from the second end and over the outer surface of the inversion support catheter with the plurality of interlocking loops overlapping to form a knit overlap configured to hold the knitted flexible tube in the compressed state, and
    wherein the knitted flexible tube is configured to be pulled proximally into the inversion support catheter by pulling the puller proximally so that the knitted flexible tube stretches from the compressed state, and rolls and inverts over a distal end of the inversion support catheter;
    wherein the inversion support catheter comprises a plurality of slots or cut-out regions configured to enhance flexibility while maintaining column strength of the inversion support catheter such that the inversion support catheter is able to withstand at least about 500 g of compressive force without buckling.

2. The apparatus of claim 1, wherein, in the compressed state, the interlocking loops of the knitted flexible tube overlap to form the knit overlap, and wherein the knit overlap extends more than 20% of a longitudinal length of the interlocking loops.

3. The apparatus of claim 1, wherein the interlocking loops of the knitted flexible tube comprise woven links that are connected end-to-end, forming a helical winding pattern.

4. The apparatus of claim 1, wherein one or more regions of the knitted flexible tube are held against the outer surface of the inversion support catheter to thereby maintain the knitted flexible tube in the compressed state.

5. The apparatus of claim 1, further comprising a releasable stop or lock disposed on the outer surface of the inversion support catheter and engaging with one or more regions of the knitted flexible tube to thereby maintain the knitted flexible tube in the compressed state.

6. The apparatus of claim 5, wherein the releasable stop or lock comprises a plurality of finger elements that engage with respective loops of the knitted flexible tube.

7. The apparatus of claim 1, further comprising a proximal port in fluid communication with a lumen of the puller, and configured to couple with a vacuum source to apply vacuum through the puller lumen.

8. The apparatus of claim 1, further comprising an intermediate catheter having a lumen through which the inversion support catheter extends, the intermediate catheter lumen in fluid communication with a proximal port configured to couple with a vacuum source to apply vacuum between the intermediate catheter and the inversion support catheter.

9. The apparatus of claim 1, further comprising an intermediate catheter extending over the inversion support catheter, wherein the knitted flexible tube is disposed between the intermediate catheter and the inversion support catheter.

10. The apparatus of claim 1, wherein the knitted flexible tube comprises a filament knitted to form the plurality of interlocking loops, and wherein the plurality of interlocking loops have a longitudinal length that is between 0.5 mm and 10 mm.

11. The apparatus of claim 1, wherein the knitted flexible tube has an inner diameter that is no more than 20% greater than an outer diameter of the inversion support catheter.

12. The apparatus of claim 1, wherein the knitted flexible tube is shape set to a first configuration that has an outer diameter between 0.5 mm and 10 mm, and a second configuration that has an inner diameter that is at least 60% of an inner diameter of the inversion support catheter.

13. The apparatus of claim 1, wherein the puller comprises a puller catheter.

14. The apparatus of claim 1, wherein the inversion support catheter comprises a plurality of slits or openings around a perimeter and along a length, respectively, of the inversion support catheter.

15. The apparatus of claim 1, further comprising a guidewire within the puller.

16. The apparatus of claim 1, wherein puller comprises a micro-catheter or a guidewire.

17. An inverting tube apparatus, comprising:

an inversion support catheter;

a puller at least partially disposed within a lumen of the inversion support catheter; and a knitted flexible tube extending over a distal end of the inversion support catheter in a compressed state, the knitted flexible tube having a plurality of interlocking loops, a first end coupled to a distal end region of the puller, and a second end disposed on an outer surface of the inversion support catheter, wherein the knitted flexible tube extends distally from the second end and over the outer surface of the inversion support catheter with the interlocking loops overlapping to form a knit overlap configured to hold the knitted tube in the compressed state, the knit overlap extends more than 20% of a longitudinal length of the interlocking loops in the compressed state, and the knitted flexible tube is configured to be pulled proximally into the inversion support catheter by pulling the puller proximally so that the knitted flexible tube rolls and inverts over a distal end of the inversion support catheter, wherein the inversion support catheter comprises a plurality of slits or openings around a perimeter and along a length, respectively, of the inversion support catheter.

18. An inverting tube apparatus, comprising:

an inversion support catheter;

a puller at least partially disposed within a lumen of the inversion support catheter;

a knitted flexible tube extending over a distal end of the inversion support catheter in a compressed state, the knitted flexible tube having a plurality of interlocking loops, a first end coupled to a distal end region of the puller, and a second end disposed on an outer surface of the inversion support catheter, wherein the knitted flexible tube extends distally from the second end and over the outer surface of the inversion support catheter with the interlocking loops overlapping to form a knit overlap, the knit overlap extends more than 20% of a longitudinal length of the interlocking loops in the compressed state, and the knitted flexible tube is configured to be pulled proximally into the inversion support catheter by pulling the puller proximally so that the knitted flexible tube rolls and inverts over a distal end of the inversion support catheter; and a releasable stop or lock disposed on the outer surface of the inversion support catheter, the releasable stop or lock engaging with one or more regions of the knitted flexible tube to thereby maintain the knitted flexible tube in the compressed state, wherein the releasable stop or lock comprises a plurality of finger elements that engage with respective loops of the knitted flexible tube.

\* \* \* \* \*